(12) United States Patent
Alvaro et al.

(10) Patent No.: US 9,193,704 B2
(45) Date of Patent: Nov. 24, 2015

(54) HYDANTOIN DERIVATIVES AS KV3 INHIBITORS

(75) Inventors: Giuseppe Alvaro, Verona (IT); Anne Decor, Verona (IT); Dieter Hamprecht, Verona (IT); Agostino Marasco, Verona (IT)

(73) Assignee: AUTIFONY THERAPEUTICS LIMITED, London (GB)

( * ) Notice: Subject to any disclaimer, the term of this patent is extended or adjusted under 35 U.S.C. 154(b) by 0 days.

(21) Appl. No.: 14/124,516

(22) PCT Filed: Jun. 7, 2012

(86) PCT No.: PCT/GB2012/051278
§ 371 (c)(1),
(2), (4) Date: Dec. 6, 2013

(87) PCT Pub. No.: WO2012/168710
PCT Pub. Date: Dec. 13, 2012

(65) Prior Publication Data
US 2014/0107139 A1    Apr. 17, 2014

(30) Foreign Application Priority Data

Jun. 7, 2011 (GB) .................................. 1109514.8
Aug. 10, 2011 (GB) .................................. 1113761.9
Jun. 6, 2012 (GB) .................................. 1209986.7

(51) Int. Cl.
| | | |
|---|---|---|
| C07D 401/00 | (2006.01) |
| C07D 401/04 | (2006.01) |
| C07D 233/00 | (2006.01) |
| C07D 307/93 | (2006.01) |
| C07D 307/87 | (2006.01) |
| C07D 307/94 | (2006.01) |
| C07D 311/76 | (2006.01) |
| C07D 403/04 | (2006.01) |
| C07D 405/12 | (2006.01) |
| C07D 405/14 | (2006.01) |

(52) U.S. Cl.
CPC ............ *C07D 307/93* (2013.01); *C07D 307/87* (2013.01); *C07D 307/94* (2013.01); *C07D 311/76* (2013.01); *C07D 401/04* (2013.01); *C07D 403/04* (2013.01); *C07D 405/12* (2013.01); *C07D 405/14* (2013.01)

(58) Field of Classification Search
USPC .......... 546/274.1, 274.7; 548/322.5; 549/469; 514/259.5, 336, 390
See application file for complete search history.

(56) References Cited

U.S. PATENT DOCUMENTS

| | | |
|---|---|---|
| 4,350,701 A | 9/1982 | Rentzea et al. |
| 4,675,403 A | 6/1987 | Abou-Gharbia et al. |
| 4,804,671 A | 2/1989 | Costin et al. |
| 5,362,878 A | 11/1994 | Chang et al. |
| 5,656,634 A | 8/1997 | Chang et al. |
| 5,703,087 A | 12/1997 | Perregaard et al. |
| 2003/0008884 A1 | 1/2003 | Gerusz et al. |
| 2003/0149061 A1 | 8/2003 | Nishihara et al. |
| 2005/0009817 A1 | 1/2005 | Savoy et al. |
| 2005/0153968 A1 | 7/2005 | Bi et al. |
| 2007/0004753 A1 | 1/2007 | Sawyers et al. |
| 2007/0021352 A1* | 1/2007 | Anderson et al. ............ 514/18 |
| 2007/0254933 A1 | 11/2007 | Jung et al. |
| 2008/0139634 A2 | 6/2008 | Jung et al. |
| 2008/0261961 A1 | 10/2008 | Flynn et al. |
| 2009/0306225 A1* | 12/2009 | Lichter et al. ............ 514/772.1 |
| 2010/0172975 A1 | 7/2010 | Sawyers et al. |
| 2010/0210665 A1 | 8/2010 | Sawyers et al. |
| 2011/0003839 A1 | 1/2011 | Jung et al. |
| 2012/0190718 A1 | 7/2012 | Jung et al. |
| 2012/0289526 A1 | 11/2012 | Alvaro et al. |

FOREIGN PATENT DOCUMENTS

| | | |
|---|---|---|
| DE | 3836175 | 5/1990 |
| EP | 0 277 842 | 8/1988 |
| EP | 0277842 | 8/1988 |
| EP | 0277842 A1 * | 8/1988 |
| EP | 0368008 | 5/1990 |
| EP | 0726898 | 12/2000 |

(Continued)

OTHER PUBLICATIONS

National Ataxia Foundation (Published 2011).*

(Continued)

*Primary Examiner* — Paul Zarek
*Assistant Examiner* — George W Kosturko
(74) *Attorney, Agent, or Firm* — Nixon & Vanderhye P.C.

(57) ABSTRACT

The invention provides compounds of formula (I): Said compounds being inhibitors of Kv3 channels and of use in the prophylaxis or treatment of related disorders.

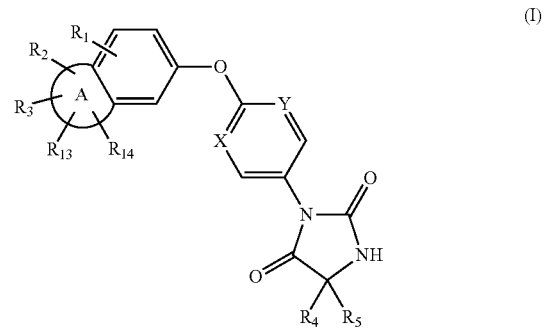

11 Claims, No Drawings

(56) References Cited

FOREIGN PATENT DOCUMENTS

| | | |
|---|---|---|
| EP | 1206935 | 5/2002 |
| GB | 2216890 | 10/1989 |
| WO | 91/04027 | 4/1991 |
| WO | 96/36229 | 11/1996 |
| WO | 96/36633 | 11/1996 |
| WO | 97/00612 | 1/1997 |
| WO | 98/05652 | 2/1998 |
| WO | 98/23155 | 6/1998 |
| WO | 98/23156 | 6/1998 |
| WO | 98/33382 | 8/1998 |
| WO | 01/76582 | 10/2001 |
| WO | 03/048134 | 6/2003 |
| WO | 03/066050 | 8/2003 |
| WO | 2004/099159 | 11/2004 |
| WO | 2005/000309 | 1/2005 |
| WO | 2005/049580 | 6/2005 |
| WO | 2006/071471 | 7/2006 |
| WO | 2006/124118 | 11/2006 |
| WO | 2007/126765 | 11/2007 |
| WO | 2007/127010 | 11/2007 |
| WO | 2010/072598 | 7/2010 |
| WO | 2011/069951 | 6/2011 |
| WO | 2011/073114 | 6/2011 |
| WO | WO 2011/069951 | 6/2011 |
| WO | WO 2011069951 A1 * | 6/2011 |
| WO | 2012/076877 | 6/2012 |
| WO | WO 2012/076877 | 6/2012 |
| WO | 2013/083994 | 6/2013 |
| WO | 2013/175211 | 11/2013 |
| WO | 2013/175215 | 11/2013 |
| WO | 2013/182850 | 12/2013 |
| WO | 2013/182851 | 12/2013 |

OTHER PUBLICATIONS

Insel et al (Nature vol. 468, pp. 187-193 published 2010).*
Autoimmune Inner Ear Disease. Medindia (published 1997).*
Rudy and McBain, Kv3 channels: voltage-gated $K^+$ channels designed for high-frequency repetitive firing, Trends in Neurosciences, 24, 517-526, 2001.
Weiser et al., Differential Expression of Shaw-related $K^+$ Channels in the Rat Central Nervous System, J.Neurosci., 14, pp. 949-972, 1994.
Chow et al., J.Neurosci., $K^+$ Channel Expression Distinguishes Subpopulations of Parvalbumin- and Somatostatin-Containing Neocortical Interneurons, 19, pp. 9332-9345, 1999.
Martina et al., Functional and Molecular Differences between Voltage-Gated $K^+$ Channels of Fast-spiking Interneurons and Pyramidal Neurons of Rat Hippocampus, J.Neurosci., 18, pp. 8111-8125, 1998.
McDonald and Mascagni, Differential Expression of Kv3.1b and Kv3.2 Potassium Channel Subunits in Interneurons of the Basolateral Amygdala, J.Neurosci., 138, pp. 537-547, 2006.
International Search Report and Written Opinion for PCT/EP2010/068946.
International Search Report and Written Opinion for PCT/GB2011/052414.
International Search Report and Written Opinion for PCT/GB2012/051278.
Chang et al., Distribution of Kv3.3 Potassium Channel Subunits in Distinct Neuronal Populations of Mouse Brain, J. Comp. Neurol., 502, pp. 953-972, 2007.
Kasten et al., Differential regulation of action potential firing in adult murine thalamocortical neurons by Kv3.2, Kv1 and SK potassium and N-type calcium channels, J.Physiol., 584, pp. 565-582, 2007.
Sacco et al., Properties and expression of Kv3 channels is cerebellar Purkinje cells, Mol. Cell. Neurosci., 33, pp. 170-179, 2006.
Li et al., Localization of Two High-Threshold Potassium Channel Subunits in the Rat Auditory System, J. Comp. Neurol., 437, pp. 196-218, 2001.
Joho et al., Increased γ- and Decreased δ-Oscillations in a Mouse Deficient for a Potassium Channel Expressed in Fast-Spiking Interneurons, J.Neurophysiol., 82, pp. 1855-1864, 1999.
Lau et al., Impaired Fast-Spiking, Suppressed Cortical Inhibition, and Increased Susceptibility to Seizures in Mice Lacking Kv3.2 $K^+$ Channel Proteins, J.Neurosci., 20, pp. 9071-9085, 2000.
McMahon et al., Allele-dependent changes of olivocerebellar circuit properties in the absence of the voltage-gated potassium channels Kv3.1 and Kv3.3, Eur. J.Neurosci., 19, pp. 3317-3327, 2004.
Espinosa et al., Alcohol Hypersensitivity, Increased Locomotion, and Spontaneous Myoclonus in Mice Lacking the Potassium Channels Kv3.1 and Kv3.3, J.Neurosci., 21, pp. 6657-6665, 2001.
Espinosa et al., Ablation of Kv3.1 and Kv3.3 Potassium Channels Disrupts Thalamocortical Oscillations In Vitro and In Vivo, J.Neurosci., 28, pp. 5570-5581, 2008.
Diochot et al., Sea Anemone Peptides with a Specific Blocking Activity against the Fast Inactivating Potassium Channel Kv3.4, J. Biol. Chem., 273, pp. 6744-6749, 1998.
Yeung et al., Modulation of Kv3 Subfamily Potassium Currents by the Sea Anemone Toxin BDS: Significance for CNS and Biophysical Studies, J.Neurosci., 25, pp. 8735-8745, 2005.
Atzori et al., $H_2$ histamine receptor-phosphorylation of Kv3.2 modulates interneuron fast spiking, Nat. Neurosci., 3, pp. 791-798, 2000.
Song et al., Acoustic environment determines phosphorylation state of the Kv3.1 potassium channel in auditory neurons, Nat Neurosci., 8, pp. 1335-1342, 2005.
Reynolds et al., Calcium Binding Protein Markers of GABA Deficits in Schizophrenia—Post Mortem Studies and Animal Models, Neurotox. Res., 6, pp. 57-61, 2004.
Benes et al., Circuitry based gene expression profiles in GABA cells of the trisynaptic pathway in schizophrenics versus bipolars, PNAS, 105, pp. 20935-20940, 2008.
Brambilla et al., GABAergic dysfunction in mood disorders, Mol. Psychiatry, 8, pp. 721-37, 2003.
Aroniadou-Anderjaska et al., Mechanisms regulating GABAergic inhibitory transmission in the basolateral amygdala: implications for epilepsy and anxiety disorders, Amino Acids, 32, pp. 305-315, 2007.
Ben-Ari, Seizures Beget Seizures: The Quest for GABA as a Key Player, Crit. Rev. Neurobiol., 18, pp. 135-144, 2006.
Markram et al., Interneurons of the Neocortical Inhibitory System, Nat.Rev.Neurosci., 5, pp. 793-807, 2004.
Fisahn, Kainate receptors and rhythmic activity in neuronal networks: hippocampal gamma oscillations as a tool, J.Physiol, 562, pp. 65-72, 2005.
Engel et al., Dynamic Predictions: Oscillations and Synchrony in Top-Down Processing, Nat.Rev.Neurosci., 2, pp. 704-716, 2001.
Spencer et al., Neural synchrony indexes disordered perception and cognition in schizophrenia, PNAS, 101, pp. 17288-17293, 2004.
Schulz and Steimer, Neurobiology of Circadian Systems, CNS Drugs, 23 Suppl 2, pp. 3-13, 2009.
Goldman and Holme, Hearing loss and tinnitus—the hidden healthcare time bomb, Drug Discovery Today, 15, pp. 253-255, 2010.
B. Shield, Evaluation of the social and economic costs of hearing impairment, A report for Hear-It AISBL: www.hear-it.org/multimedia/Hear_It_Report_October_2006.pdf, 2006.
von Hehn et al., Loss of Kv3.1 Tonotopicity and Alterations in cAMP Response Element-Binding Protein Signaling in Central Auditory Neurons of Hearing Impaired Mice, J. Neurosci., 24, pp. 1936-1940, 2004.
Jung et al., Age-related changes in the distribution of Kv1.1 and Kv3.1 in rat cochlear nuclei, Neurol. Res., 27, pp. 436-440, 2005.
Kaczmarek et al., Regulation of the timing of MNTB neurons by short-term and long-term modulation of potassium channels, Hearing Res., 206, pp. 133-145, 2005.
Strumbos et al., Specific and Rapid Effects of Acoustic Stimulation on the Tonotopic Distribution of Kv3.1b Potassium Channels in the Adult Rat, J. Neuroscience, 167, pp. 567-572, 2010.
Strumbos et al., Fragile X Mental Retardation Protein Is Required for Rapid Experience-Dependent Regulation of Potassium Channel Kv3.1b, J. Neuroscience, 167, pp. 10263-10271, 2010.
Berge et al., Pharmaceutical Salts, J. Pharm. Sci., 66, pp. 1-19, 1977.
Waters et al. Mutations in voltage-gated potassium channel KCNC3 cause degenerative and developmental central nervous system phenotypes, Nature Genetics, 28, pp. 447-451, 2006.

(56) References Cited

OTHER PUBLICATIONS

Minassian et al. Altered Kc3.3 channel gating in early-onset spinocerebellar ataxia type 13, J. Physiol., 590.7, pp. 1599-1614, 2012.

Campbell et al. D-methionine (D-met) significantly rescues noise-induced hearing loss: Timing studies, Hearing Research, 82, pp. 138-144, 2011.

International Search Report for PCT/GB2012/051278, mailed Jul. 13, 2012, Bosma, Peter.

Written Opinion of the International Searching Authority for PCT/GB2012/051278, mailed Jul. 13, 2012, Bosma, Peter.

Pilati et al., Acoustic over-exposure triggers burst firing in dorsal cochlear nucleus fusiform cells, Hearing Research, 283, pp. 98-106, 2012.

Harte et al, "Efficacy and relevance of the modulation of Ky3 channels to alleviate cognitive dysfunction in an animal model of schizaphrenia symptomatology", 4th Biennial Schizophrenia International Research Conference (Apr. 2014), Abstract.

Mabrouk et al, "A novel Kv3 positive modulator augments gamma frequency oscillations in the mammalian neocortex in vitro", $4^{th}$ Biennial Schizophrenia International Research Conference (Apr. 2014), Abstract.

Leger et al, "Two novel KV3 ion channel modulators alleviate cognitive dysfunction and social behaviour deficits of relevance to schizophrenia in an animal model", $4^{th}$ Biennial Schizophrenia International Research Conference (Apr. 2014), Abstract.

Neill et al, "A novel Kv3 ion channel modulator restores cognitive function in an animal model of cognitive impairment in schizophrenia", European College of Neuropsychopharmacology Conference (Oct. 2013), Abstract.

Sidor et al, "Potential anti-manic efficacy of a Kv3 channel modulator in a model of amphetamine-induced hyperactivity and in $CLOCK\Delta19$ mutant mice", Society for Neuroscience Annual Meeting (Oct. 2012), Abstract.

\* cited by examiner

HYDANTOIN DERIVATIVES AS KV3 INHIBITORS

This application is the U.S. national phase of International Application No. PCT/GB2012/051278, filed 7 Jun. 2012, which designated the U.S. and claims priority of GB Application No. 1109514.8, filed 7 Jun. 2011; GB Application No. 1113761.9, filed 10 Aug. 2011; and GB Application No. 1209986.7, filed 6 Jun. 2012, the entire contents of each of which are hereby incorporated by reference.

TECHNICAL FIELD

This invention relates to novel compounds, pharmaceutical compositions containing them and their use in therapy, in particular as antipsychotic agents. Other uses of the compounds include the prophylaxis or treatment of hearing and hearing related disorders, including hearing loss and tinnitus, as well as schizophrenia, bipolar disorder, epilepsy, sleep disorders, and disorders where cognitive decline is a symptom.

BACKGROUND TO THE INVENTION

The Kv3 voltage-gated potassium channel family includes four members, Kv3.1, Kv3.2, Kv3.3, and Kv3.4. Genes for each of these subtypes can generate multiple isoforms by alternative splicing, producing versions with different C-terminal domains. Thirteen isoforms have been identified in mammals to date, but the currents expressed by these variants appear similar (Rudy and McBain, 2001, Trends in Neurosciences 24, 517-526). Kv3 channels are activated by depolarisation of the plasma membrane to voltages more positive than −20 mV; furthermore, the channels deactivate rapidly upon repolarisation of the membrane. These biophysical properties ensure that the channels open towards the peak of the depolarising phase of the neuronal action potential to initiate repolarisation. Rapid termination of the action potential mediated by Kv3 channels allows the neuron to recover more quickly to reach sub-threshold membrane potentials from which further action potentials can be triggered. As a result, the presence of Kv3 channels in certain neurons contributes to their ability to fire at high frequencies (Rudy and McBain, 2001, Trends in Neurosci. 24, 517-526). Kv3.1-3 subtypes are predominant in the CNS, whereas Kv3.4 channels are found predominantly in skeletal muscle and sympathetic neurons (Weiser et al., 1994, J. Neurosci. 14, 949-972). Kv3.1-3 channel subtypes are differentially expressed by sub-classes of interneurons in cortical and hippocampal brain areas (e.g. Chow et al., 1999, J. Neurosci. 19, 9332-9345; Martina et al., 1998, J. Neurosci. 18, 8111-8125; McDonald and Mascagni, 2006, Neurosci. 138, 537-547, Chang et al., 2007, J. Comp. Neurol. 502, 953-972), in the thalamus (e.g. Kasten et al., 2007, J. Physiol. 584, 565-582), cerebellum (e.g. Sacco et al., 2006, Mol. Cell. Neurosci. 33, 170-179), and auditory brain stem nuclei (Li et al., 2001, J. Comp. Neurol. 437, 196-218).

Characterisation of mice in which one or more of the Kv3 subtypes has been deleted shows that the absence of Kv3.1 gives rise to increased locomotor activity, altered electroencephalographic activity, and a fragmented sleep pattern (Joho et al., 1999, J. Neurophysiol. 82, 1855-1864). The deletion of Kv3.2 leads to a reduction in seizure threshold and altered cortical electroencephalographic activity (Lau et al., 2000, J. Neurosci. 20, 9071-9085). Deletion of Kv3.3 is associated with mild ataxia and motor deficits (McMahon et al., 2004, Eur. J. Neurosci. 19, 3317-3327). Furthermore, reduction of function mutations of Kv3.3 channels in humans have been associated with spinocerebellar ataxia type 13 (Waters et al., 2006, Nat. Genet. 38, 447-451). Double deletion of Kv3.1 and Kv3.3 gives rise to a severe phenotype characterised by spontaneous seizures, ataxia, and an increased sensitivity to the effects of ethanol (Espinosa et al., 2001, J. Neurosci. 21, 6657-6665; Espinosa et al., 2008, J. Neurosci. 28, 5570-5581).

The known pharmacology of Kv3 channels is limited. Tetraethylammonium (TEA) has been shown to inhibit the channels at low millimolar concentrations (Rudy and McBain, 2001, Trends in Neurosci. 24, 517-526), and blood-depressing substance (BDS) toxins from the sea anemone, *Anemonia sulcata* (Diochot et al., 1998, J. Biol. Chem. 273, 6744-6749), have been shown to selectively inhibit Kv3 channels with high affinity (Yeung et al., 2005, J. Neurosci. 25, 8735-8745). In addition to compounds acting directly on Kv3 channels, agonists of receptors that activate protein kinase A (PKA) and protein kinase C (PKC) have been shown to modulate Kv3-mediated currents in specific brain areas, leading to a reduction in the ability of the neurons to fire at high frequency (Atzori et al., 2000, Nat. Neurosci. 3, 791-798; Song et al., 2005, Nat Neurosci. 8, 1335-1342); these studies suggest that PKA and PKC can specifically phosphorylate Kv3 channels in a neuron-specific manner, causing a reduction in Kv3-mediated currents.

Bipolar disorder, schizophrenia, anxiety, and epilepsy are serious disorders of the central nervous system that have been associated with reduced function of inhibitory interneurons and gamma-amino butyric acid (GABA) transmission (Reynolds et al., 2004, Neurotox. Res. 6, 57-61; Benes et al., 2008, PNAS, 105, 20935-20940; Brambilla et al., 2003, Mol. Psychiatry. 8, 721-37, 715; Aroniadou-Anderjaska et al., 2007, Amino Acids 32, 305-315; Ben-Ari, 2006, Crit. Rev. Neurobiol. 18, 135-144). Parvalbumin positive basket cells that express Kv3 channels in the cortex and hippocampus play a key role in generating feedback inhibition within local circuits (Markram et al., 2004, Nat. Rev. Neurosci. 5, 793-807). Given the relative dominance of excitatory synaptic input over inhibitory input to glutamatergic pyramidal neurons in these circuits, fast-firing of interneurons supplying inhibitory input is essential to ensure balanced inhibition. Furthermore, accurate timing of inhibitory input is necessary to sustain network synchronisation, for example, in the generation of gamma frequency field potential oscillations that have been associated with cognitive function (Fisahn et al., 2005, J. Physiol 562, 65-72; Engel et al., 2001, Nat. Rev. Neurosci. 2, 704-716). Notably, a reduction in gamma oscillations has been observed in patients with schizophrenia (Spencer et al., 2004, PNAS 101, 17288-17293). Consequently, positive modulators of Kv3 channels might be expected to enhance the firing capabilities of specific groups of fast-firing neurons in the brain. These effects may be beneficial in disorders associated with abnormal activity of these neuronal groups.

In addition, Kv3.2 channels have been shown to be expressed by neurons of the superchiasmatic nucleus (SCN) the main circadian pacemaker in the CNS (Schulz and Steimer, 2009, CNS Drugs 23 Suppl 2, 3-13).

Hearing loss represents an epidemic that affects approximately 16% of the population in Europe and the US (Goldman and Holme, 2010, Drug Discovery Today 15, 253-255), with a prevalence estimated at 250 million people worldwide (B. Shield, 2006, Evaluation of the social and economic costs of hearing impairment. A report for Hear-It AISBL: www-.hear-it.org/multimedia/Hear_It_Report_October_2006.pdf). As life expectancy continues to increase, so too will the number of people suffering from hearing disorders.

Furthermore, it is believed that modern lifestyles may exacerbate this burden as the younger generation ages. Hearing conditions, including tinnitus have a profound effect on the quality of life, causing social isolation, depression, work and relationship difficulties, low self-esteem, and prejudice. Voltage-gated ion channels of the Kv3 family are expressed at high levels in auditory brainstem nuclei (Li et al., 2001, J. Comp. Neurol. 437, 196-218) where they permit the fast firing of neurons that transmit auditory information from the cochlear to higher brain regions. Loss of Kv3.1 channel expression in central auditory neurons is observed in hearing impaired mice (von Hehn et al., 2004, J. Neurosci. 24, 1936-1940), furthermore, a decline in Kv3.1 expression may be associated with loss of hearing in aged mice (Jung et al. 2005 Neurol. Res. 27, 436-440), and loss of Kv3 channel function may also follow noise-trauma induced hearing loss (Pilati et al., Hear Res. 2012 January 283(1-2):98-106). Furthermore, pathological plasticity of auditory brainstem networks is likely to contribute to symptoms that are experienced by many people suffering from hearing loss of different types. Recent studies have shown that regulation of Kv3.1 channel function and expression has a major role in controlling auditory neuron excitability (Kaczmarek et al., 2005, Hearing Res. 206, 133-145), suggesting that this mechanism could account for some of the plastic changes that give rise to tinnitus. These data support the hypothesis that positive modulation of Kv3 channels in auditory brainstem nuclei could have a therapeutic benefit in patients suffering from hearing loss. Finally, Fragile X syndrome and autism are frequently associated with hypersensitivity to sensory input, including auditory stimuli. Recent findings suggest that the protein coded by the FMR-I gene, whose mutation or absence gives rise to Fragile X syndrome, may directly regulate the expression of Kv3.1 channels in the auditory brainstem nuclei (Strumbos et al., 2010, J. Neuroscience, in press), suggesting that mis-regulation of Kv3.1 channels could give rise to hyperacusis in patients suffering from Fragile X or autism. Consequently, we propose that small molecule modulators of Kv3 channels in auditory brainstem nuclei could have a benefit in the treatment of disorders of hearing, including tinnitus and auditory hyper-acuity associated with Fragile X syndrome and autism.

Spinocerebellar ataxia type 13 (SCA13) is a human autosomal dominant disease caused by mutations in the KCNC3 gene that encodes the Kv3.3 channel. These mutations have been shown to cause a reduction in function of the channels (Waters et al., 2006, Nat. Genet. 38, 447-451; Minassian et al., 2012, J Physiol. 590.7, 1599-1614). Coexpression of Kv3.1 and Kv3.3 in many brain areas, including the cerebellum suggests some redundancy or the ability of one subtype to compensate for the absence of the other, indeed the phenotype of the Kv3.1/Kv3.3 double knockout mice is markedly more severe than either of the two single knockouts (e.g. Espinosa et al., 2008, J. Neurosci. 28, 5570-5581). Furthermore, it is possible that Kv3.1 and Kv3.3 proteins assemble to form heteromeric channels in some neurons. The ability of Kv3.1 to compensate for a loss of function of Kv3.3 may explain why certain mutations in the latter are only associated with an onset of spinocerebellar ataxia later in adult life, rather than from birth (Minassian et al., 2012, J Physiol. 590.7, 1599-1614). Consequently, we propose that small molecule modulators of either Kv3.3 or Kv3.1 might be beneficial in the treatment of spinocerebellar ataxia, in particular SCA13.

Patent applications WO2011/069951 and PCT/GB2011/052414 (presently unpublished) disclose compounds which are modulators of Kv3.1 and Kv3.2. Further, the value of such compounds is demonstrated in animal models of seizure, hyperactivity, sleep disorders, psychosis, cognitive deficit, bipolar disorder and hearing disorders.

There remains a need for the identification of alternative modulators of Kv3.1 and Kv3.2, in particular modulators of Kv3.1 and Kv3.2 which may demonstrate certain channel selectivity profiles or desirable pharmacokinetic parameters, for example high brain availability.

SUMMARY OF THE INVENTION

The present invention provides a compound of formula (I):

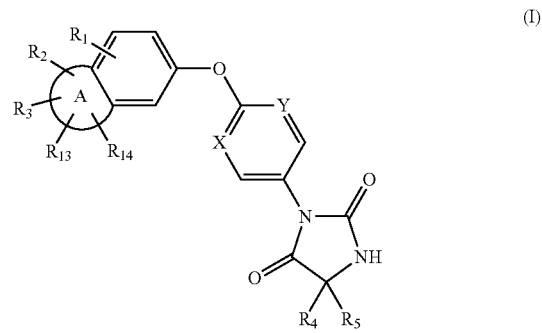

wherein:
$R_1$ is H, $C_{1-4}$alkyl, halo, halo$C_{1-4}$alkyl, CN, $C_{1-4}$alkoxy, or halo$C_{1-4}$alkoxy;
$R_2$ is H, $C_{1-5}$alkyl, $C_{3-5}$ spiro carbocyclyl, halo$C_{1-5}$alkyl or halo;
$R_3$ is H, $C_{1-4}$alkyl, halo$C_{1-4}$alkyl, halo; or $R_3$ is absent;
$R_{13}$ is H, $C_{1-4}$alkyl, halo$C_{1-4}$alkyl, halo; or $R_{13}$ is absent;
$R_{14}$ is H, $C_{1-4}$alkyl, halo$C_{1-4}$alkyl, halo; or $R_{14}$ is absent;
A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;
X is CH or N;
Y is $CR_{15}$ or N;
$R_{15}$ is H or $C_{1-4}$alkyl;
$R_4$ is $C_{1-4}$ alkyl;
$R_5$ is H, Deuterium, $C_{1-4}$ alkyl;
or $R_4$ and $R_5$ can be fused to form $C_{3-4}$ spiro carbocyclyl;
wherein $R_2$ and $R_3$ may be attached to the same or a different ring atom; wherein $R_2$ may be attached to a fused ring atom; and wherein $R_{13}$ and $R_{14}$ may be attached to the same or a different ring atom.

A compound of formula (I) may be provided in the form of a pharmaceutically acceptable salt and/or solvate thereof. In one embodiment of the invention a compound of formula (I) is provided in the form of a pharmaceutically acceptable salt.

The compounds of formula (I) may be used as medicaments, in particular for the prophylaxis or treatment of hearing disorders, including hearing loss and tinnitus, as well as schizophrenia, bipolar disorder, epilepsy, sleep disorders, cognition impairment or ataxia.

Further, there is provided a method for the prophylaxis or treatment of hearing disorders, including hearing loss and tinnitus, as well as schizophrenia, bipolar disorder, epilepsy, sleep disorders, cognition impairment or ataxia by administering to a subject a compound of formula (I).

Compounds of formula (I) may be used in the manufacture of a medicament for the prophylaxis or treatment of hearing disorders, including hearing loss and tinnitus, as well as schizophrenia, bipolar disorder, epilepsy, sleep disorders, cognition impairment or ataxia.

Also provided are pharmaceutical compositions containing a compound of formula (I) and a pharmaceutically acceptable carrier or excipient.

Additionally provided are prodrug derivatives of the compounds of formula (I).

DETAILED DESCRIPTION OF THE INVENTION

The present invention provides a compound of formula (I):

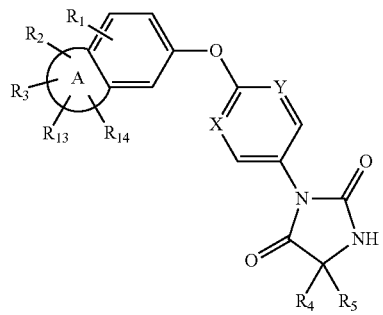

(I)

wherein:
$R_1$ is H, $C_{1-4}$alkyl, halo, halo$C_{1-4}$alkyl, CN, $C_{1-4}$alkoxy, or halo$C_{1-4}$alkoxy;
$R_2$ is H, $C_{1-5}$alkyl, $C_{3-5}$ spiro carbocyclyl, halo$C_{1-5}$alkyl or halo;
$R_3$ is H, $C_{1-4}$alkyl, halo$C_{1-4}$alkyl, halo; or $R_3$ is absent;
$R_{13}$ is H, $C_{1-4}$alkyl, halo$C_{1-4}$alkyl, halo; or $R_{13}$ is absent;
$R_{14}$ is H, $C_{1-4}$alkyl, halo$C_{1-4}$alkyl, halo; or $R_{14}$ is absent;
A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;
X is CH or N;
Y is $CR_{15}$ or N;
$R_{15}$ is H or $C_{1-4}$alkyl;
$R_4$ is $C_{1-4}$ alkyl;
$R_5$ is H, Deuterium, $C_{1-4}$ alkyl;
or $R_4$ and $R_5$ can be fused to form $C_{3-4}$ spiro carbocyclyl;
wherein $R_2$ and $R_3$ may be attached to the same or a different ring atom; wherein $R_2$ may be attached to a fused ring atom; and wherein $R_{13}$ and $R_{14}$ may be attached to the same or a different ring atom;
or a pharmaceutically acceptable salt and/or solvate thereof.

The present invention also provides a compound of formula (IA):

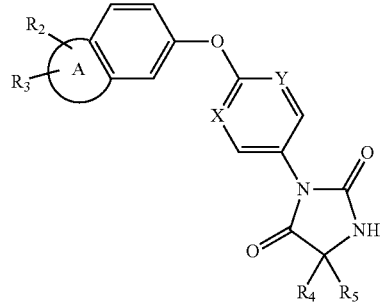

(IA)

wherein:
$R_2$ is H, $C_{1-4}$alkyl, $C_{3-5}$ spiro carbocyclyl or halo$C_{1-4}$alkyl;
$R_3$ is H, $C_{1-4}$alkyl or halo$C_{1-4}$alkyl;
A is a 5 or 6 membered saturated or unsaturated heterocycle, with at least one O atom;
X is CH or N;
Y is $CR_{15}$ or N;
$R_{15}$ is H or methyl;
$R_4$ is $C_{1-4}$ alkyl;
$R_5$ is H or $C_{1-4}$ alkyl;
wherein $R_2$ and $R_3$ may be attached to the same or a different ring atom;
or a pharmaceutically acceptable salt and/or solvate thereof.

In one embodiment of the invention $R_1$ is H, $C_{1-4}$alkyl, halo or halo$C_{1-4}$alkyl. In another embodiment of the invention $R_1$ is H or methyl. In one embodiment of the invention $R_1$ is H. In another embodiment of the invention $R_1$ is $C_{1-4}$alkyl, in particular methyl.

Suitably $R_2$ is H, $C_{1-4}$alkyl, $C_{3-4}$spiro carbocyclyl, halo$C_{1-4}$alkyl or halo. Alternatively, $R_2$ is H, $C_{1-5}$alkyl, $C_{3-5}$spiro carbocyclyl or halo$C_{1-5}$alkyl. In one embodiment of the invention $R_2$ is $C_{1-5}$alkyl, such as $C_{1-4}$alkyl, in particular methyl, ethyl, tert-butyl or cyclopropyl. In one embodiment of the invention $R_2$ is $C_{3-5}$spiro carbocyclyl, in particular $C_4$spiro carbocyclyl or $C_5$spiro carbocyclyl. In one embodiment of the invention $R_2$ is halo$C_{1-5}$alkyl, such as halo$C_{1-4}$alkyl, in particular trifluoromethyl or 2,2,2-trifluoroethyl. In one embodiment of the invention $R_2$ is H, methyl, ethyl, tert-butyl, cyclopropyl, $C_{4-5}$spiro carbocyclyl, trifluoromethyl or 2,2,2-trifluoroethyl, especially H, methyl, ethyl, tert-butyl, cyclopropyl, $C_{4-5}$spiro carbocyclyl or trifluoromethyl.

Suitably $R_3$ is H, $C_{1-4}$alkyl, halo$C_{1-4}$alkyl or halo. Alternatively, $R_3$ is H, $C_{1-4}$alkyl, or halo$C_{1-4}$alkyl. In one embodiment of the invention $R_3$ is H. In one embodiment of the invention $R_3$ is $C_{1-4}$alkyl, in particular methyl, ethyl, tert-butyl or cyclopropyl. In one embodiment of the invention, $R_3$ is halo$C_{1-4}$alkyl, in particular trifluoromethyl or 2,2,2-trifluoroethyl. The skilled person will appreciate that, depending on the size, presence of heteroatoms and the degree of unsaturation of the A ring, $R_3$ may be absent. Consequently, in another embodiment of the invention $R_3$ is absent. In one embodiment of the invention $R_3$ is H, methyl, ethyl, tert-butyl, cyclopropyl, trifluoromethyl or 2,2,2-trifluoroethyl, especially H, methyl, ethyl or trifluoromethyl and in particular H, methyl or ethyl.

In one embodiment of the invention $R_2$ may be H, $C_{1-4}$alkyl, halo$C_{1-4}$alkyl or $C_{3-5}$spiro carbocycyl and $R_3$ may be H, $C_{1-4}$alkyl, or halo$C_{1-4}$alkyl. In a particular embodiment of the invention, $R_2$ may be methyl, ethyl, tert-butyl, cyclopropyl, $C_{3-5}$spiro carbocyclyl, trifluoromethyl or 2,2,2-trifluoroethyl and $R_3$ may be H, methyl or ethyl. In one embodiment of the invention $R_2$ is $C_{1-4}$alkyl and $R_3$ is H, for example $R_2$ is methyl, ethyl, tert-butyl or cyclopropyl. In one embodiment of the invention $R_2$ is $C_{1-4}$alkyl and $R_3$ is $C_{1-4}$alkyl, for example $R_2$ is methyl and $R_3$ is methyl, $R_2$ is ethyl and $R_3$ is ethyl or $R_2$ is methyl and $R_3$ is ethyl. In another embodiment of the invention $R_2$ is trifluoromethyl and $R_3$ is H or methyl.

In one embodiment of the invention $R_2$ and $R_3$ are attached to the same ring atom. In an alternative embodiment of the invention $R_2$ and $R_3$ are attached to different ring atoms.

In one embodiment of the invention $R_{13}$ is H or methyl. In one embodiment of the invention $R_{13}$ is H. in another embodiment of the invention $R_{13}$ is $C_{1-4}$alkyl, in particular methyl. The skilled person will appreciate that, depending on the size, presence of heteroatoms and the degree of unsaturation of the A ring, $R_{13}$ may be absent. Consequently, in another embodiment of the invention $R_{13}$ is absent.

In one embodiment of the invention $R_{14}$ is H or methyl. In one embodiment of the invention $R_{14}$ is H. in another embodiment of the invention $R_{14}$ is $C_{1-4}$alkyl, in particular methyl. The skilled person will appreciate that, depending on the size, presence of heteroatoms and the degree of unsaturation of the A ring, $R_{14}$ may be absent. Consequently, in another embodiment of the invention $R_{14}$ is absent.

Suitably, A is a 5 or 6 membered saturated or unsaturated heterocycle, with at least one O atom; which heterocycle is optionally fused with a cyclopropyl group to form a tricycle when considered together with the phenyl. In one embodiment of the invention A is a 5 membered saturated or unsaturated heterocycle, with at least one O atom; which heterocycle is optionally fused with a cyclopropyl group, a cyclobutyl group or a cyclopentyl group to form a tricycle when considered together with the phenyl. In another embodiment of the invention A is a 6 membered saturated or unsaturated heterocycle, with at least one O atom; which heterocycle is optionally fused with a cyclopropyl group, a cyclobutyl group or a cyclopentyl group to form a tricycle when considered together with the phenyl.

In one embodiment of the invention A is a 5 membered saturated or unsaturated heterocycle with at least one O atom, which heterocycle is fused with a cyclopropyl group to form a tricycle when considered together with the phenyl. In another embodiment of the invention A is a 6 membered saturated or unsaturated heterocycle with at least one O atom, which heterocycle is fused with a cyclopropyl group to form a tricycle when considered together with the phenyl. In one embodiment of the invention A is a 5 membered saturated or unsaturated heterocycle with at least one O atom. In one embodiment of the invention A is a 6 membered saturated or unsaturated heterocycle with at least one O atom.

In certain embodiments of the invention the ring A contains one heteroatom. In other embodiments of the invention the ring A contains two heteroatoms (e.g. two oxygen atoms, one oxygen atom and one nitrogen atom, or one oxygen atom and one sulphur atom).

In one embodiment of the invention A is dihydrofuran. In one embodiment of the invention A is dihydropyran. In another embodiment of the invention A is dihydrofuran fused with a cyclopropyl group, a cyclobutyl group or a cyclopentyl group. In another embodiment of the invention A is dihydropyran fused with a cyclopropyl group, a cyclobutyl group or a cyclopentyl group.

In one embodiment of the invention A is fused with a cyclopropyl group. In another embodiment of the invention A is fused with a cyclobutyl group. In a further embodiment of the invention A is fused with a cyclopentyl group. In one embodiment of the invention A is not fused with a cyclopropyl group, a cyclobutyl group or a cyclopentyl group.

In one embodiment A is dihydrofuran, dihydropyran, furan, pyran, oxazole, isoxazole, oxazine, dioxine or dioxalane. In another embodiment A is dihydrofuran, dihydropyran or dioxalane.

In one embodiment of the invention A is:

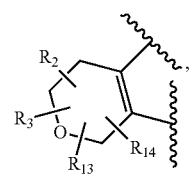

1

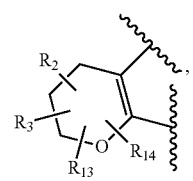

2

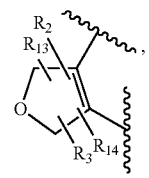

3

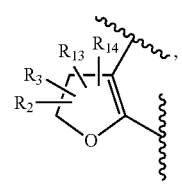

4

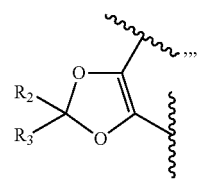

5

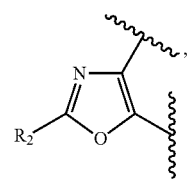

6

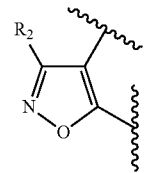

7

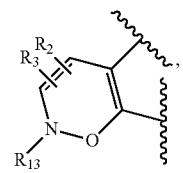

8

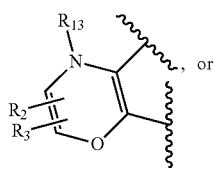, or
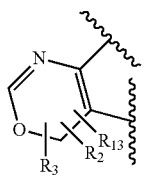
wherein
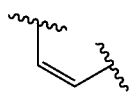
denotes a portion of the phenyl ring to which ring A is fused.
In another embodiment of the invention A is:
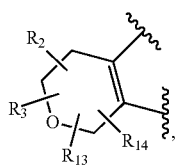
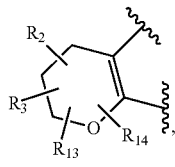
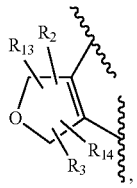
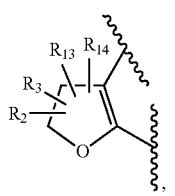
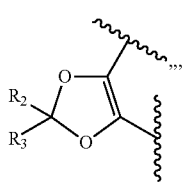
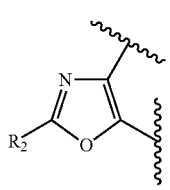
or
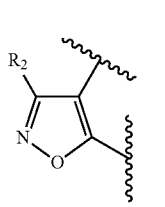
wherein
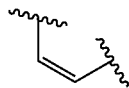
denotes a portion of the phenyl ring to which ring A is fused.
In a further embodiment of the invention A is:
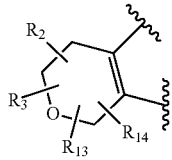
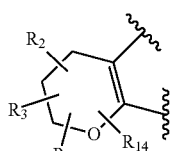
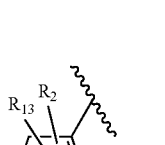
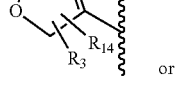
or
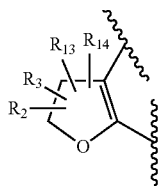

wherein

denotes a portion of the phenyl ring to which ring A is fused.

When A contains a 5 membered heterocycle containing one oxygen atom, suitably the heterocycle is dihydrofuran.

When A contains a 5 membered heterocycle containing one oxygen atom, suitably the oxygen atom is located at the benzylic position relative to the phenyl ring.

In one embodiment of the invention, A is:

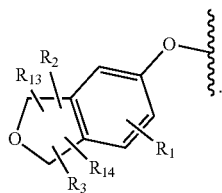

8

In another embodiment of the invention, A is:

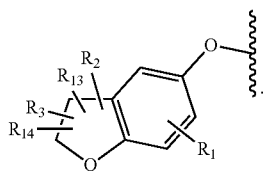

9

When A contains a 6 membered heterocycle containing one oxygen atom, suitably the heterocycle is dihydropyran.

When A contains a 6 membered heterocycle containing one oxygen atom, suitably the oxygen atom is located in the benzylic position relative to the phenyl ring.

In one embodiment of the invention, A is:

10

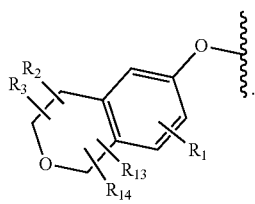

In another embodiment of the invention, A is:

10

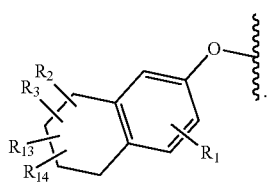

In one embodiment of the invention, A is:

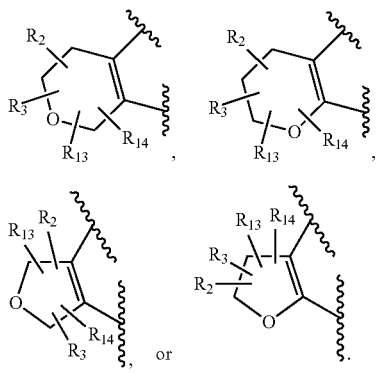

In one embodiment of the invention, A is:

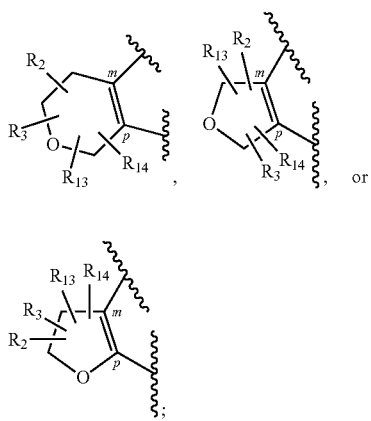

wherein m and p denote the meta and para positions, respectively, of ring A relative to the phenyl ring.

In a further embodiment of the invention, A is selected from the group consisting of:

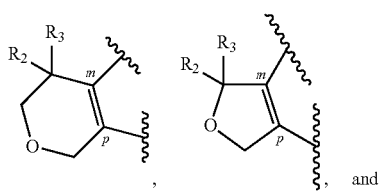, and

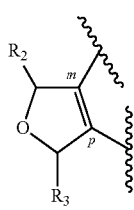

Of particular interest are compounds wherein A is:

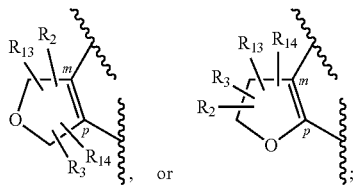

, or especially those wherein A is:

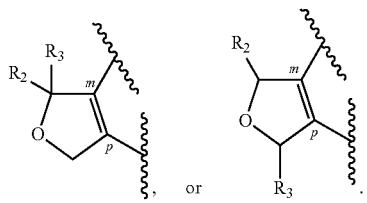

, or

In one embodiment of the invention X is CH. In another embodiment of the invention X is N.

In one embodiment of the invention Y is $CR_{15}$. In another embodiment of the invention Y is N. In a further embodiment of the invention Y is $CR_{15}$, wherein $R_{15}$ is H. In a still further embodiment of the invention Y is $CR_{15}$, wherein $R_{15}$ is $C_{1-4}$alkyl, in particular methyl.

In one embodiment of the invention X is CH and Y is $CR_{15}$, wherein $R_{15}$ is H. In another embodiment of the invention X is N and Y is $CR_{15}$, wherein $R_{15}$ is H. In a further embodiment of the invention X is N and Y is $CR_{15}$, wherein $R_{15}$ is methyl. In a further embodiment of the invention X is CH and Y is $CR_{15}$, wherein $R_{15}$ is methyl. In a still further embodiment of the invention X is N and Y is N.

Suitably, $R_4$ is methyl, ethyl, isopropyl or t-butyl. In one embodiment of the invention $R_4$ is methyl. In another embodiment of the invention $R_4$ is ethyl. In a further embodiment of the invention $R_4$ is propyl, such is isopropyl. In a yet further embodiment of the invention $R_4$ is butyl, such as t-butyl.

Suitably, $R_5$ is H or methyl. In one embodiment of the invention $R_5$ is H. In a second embodiment of the invention $R_5$ is $C_{1-4}$alkyl, in particular $R_5$ is methyl.

In one embodiment of the invention $R_4$ and $R_5$ together form a $C_3$ spiro carbocycle. In a second embodiment of the invention $R_4$ and $R_5$ together form a $C_4$ spiro carbocycle. In a further embodiment of the invention $R_4$ is methyl and $R_5$ is methyl. In an embodiment of particular interest, $R_4$ is ethyl and $R_5$ is methyl. In another embodiment, $R_4$ is ethyl and $R_5$ is ethyl. In an additional embodiment, $R_4$ is ethyl and $R_5$ is H.

Suitably, $R_4$ and $R_5$ have the stereochemical arrangement:

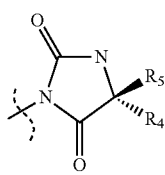

In a further aspect, the present invention provides a compound of formula (IB);

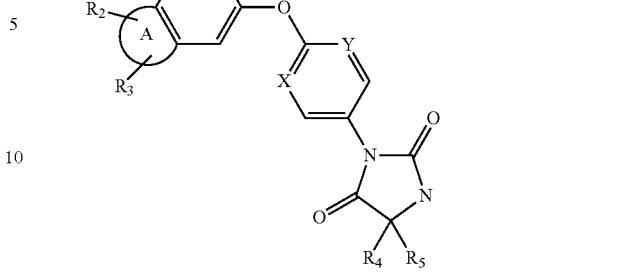

(IB)

wherein:
$R_1$ is H, or $C_{1-4}$alkyl, halo, halo$C_{1-4}$alkyl, CN, $C_{1-4}$alkoxy, halo$C_{1-4}$alkoxy;
A is a 5 or 6 membered saturated or unsaturated heterocycle, with at least one O atom; which heterocycle is optionally fused with a cyclopropyl group to form a tricycle when considered together with the phenyl;
$R_2$ is H, $C_{1-4}$alkyl, $C_{3-4}$ spiro carbocycly, halo$C_{1-4}$alkyl or halo;
$R_3$ is H, $C_{1-4}$alkyl, halo$C_{1-4}$alkyl, halo;
X is C or N;
Y is C or N;
$R_4$ is $C_{1-4}$ alkyl;
$R_5$ is H, Deuterium, $C_{1-4}$ alkyl;
or $R_4$ and $R_5$ can be fused to form $C_{3-4}$ spiro carbocyclyl;
wherein $R_2$ and $R_3$ may be attached to the same or a different ring atom;
and wherein $R_2$ may be attached to a fused ring atom;
or a pharmaceutically acceptable salt thereof.

In one embodiment of the invention $R_1$ is H.
In one embodiment of the invention $R_1$ is $C_{1-4}$alkyl. In another embodiment of the invention $R_1$ is methyl.
In one embodiment of the invention $R_2$ is H.
In one embodiment of the invention $R_2$ is $C_{1-4}$alkyl. In another embodiment $R_2$ is methyl. In a further embodiment $R_2$ is ethyl. In a yet further embodiment $R_2$ is propyl.
In one embodiment of the invention $R_2$ is a $C_3$ spiro group.
In one embodiment of the invention $R_3$ is H.
In one embodiment of the invention $R_3$ is $C_{1-4}$ alkyl. In another embodiment of the invention $R_3$ is methyl.
In one embodiment of the invention A is tetrahydrofuran, isoxazole or tetrahydropyran.
In one embodiment of the invention A is tetrahydrofuran, isoxazole or tetrahydropyran, fused with a cyclopropyl group.
In one embodiment of the invention X is C and Y is C.
In one embodiment of the invention X is N and Y is C.
In one embodiment of the invention X is N and Y is N.
In one embodiment of the invention $R_4$ is methyl. In another embodiment of the invention $R_4$ is ethyl. In a further embodiment of the invention $R_4$ is propyl. In a yet further embodiment of the invention $R_4$ is butyl.
In one embodiment of the invention $R_5$ is H.
In one embodiment of the invention $R_5$ is $C_{1-4}$alkyl. In another embodiment of the invention $R_5$ is methyl.
In one embodiment of the invention $R_4$ and $R_5$ together form a $C_3$ spiro carbocycle.
In one embodiment of the invention $R_4$ and $R_5$ together form a $C_4$ spiro carbocycle.
In one embodiment of the invention, $R_5$ is H and the $R_4$ substituent is in the S configuration.

In one embodiment of the invention R₄ is methyl and R₅ is methyl.

In one embodiment of the invention R₄ is methyl, R₅ is methyl, X is N and Y is C.

In one embodiment of the invention R₄ is methyl, R₅ is methyl, X is N, Y is C and A is tetrahydrofuran.

In one embodiment of the invention R₄ is methyl, R₅ is methyl, X is N, Y is C, A is tetrahydrofuran and R₁ is H.

In one embodiment of the invention R₄ is methyl, R₅ is methyl, X is N, Y is C, A is tetrahydrofuran, R₁ is H and R₂ is a C₃ spiro group.

In one embodiment of the invention the compound of formula (I) is (5R)-3-[4-(1,3-dihydro-2-benzofuran-5-yloxy)phenyl]-5-methyl-2,4-imidazolidinedione, or a pharmaceutically acceptable salt thereof.

References to "formula (I)" should also be construed as referring to formula (IA) and formula (IB) as appropriate to the circumstances.

In one embodiment of the invention the compound is selected from the group consisting of:
3-[2-[(3,3-dimethyl-1H-isobenzofuran-5-yl)oxy]pyrimidin-5-yl]-5,5-dimethyl-imidazolidine-2,4-dione;
3-[2-[(3,3-diethyl-1H-isobenzofuran-5-yl)oxy]pyrimidin-5-yl]-5,5-dimethyl-imidazolidine-2,4-dione;
3-[2-[(3-tert-butyl-1,3-dihydroisobenzofuran-5-yl)oxy]pyrimidin-5-yl]-5,5-dimethyl-imidazolidine-2,4-dione (enantiomer 1);
3-[2-[(3-tert-butyl-1,3-dihydroisobenzofuran-5-yl)oxy]pyrimidin-5-yl]-5,5-dimethyl-imidazolidine-2,4-dione (enantiomer 2);
5,5-dimethyl-3-[2-[[3-methyl-3-(trifluoromethyl)-1H-isobenzofuran-5-yl]oxy]pyrimidin-5-yl]imidazolidine-2,4-dione (enantiomer 1);
5,5-dimethyl-3-[2-[[3-methyl-3-(trifluoromethyl)-1H-isobenzofuran-5-yl]oxy]pyrimidin-5-yl]imidazolidine-2,4-dione (enantiomer 2);
3-[2-[(3-ethyl-1,3-dihydroisobenzofuran-5-yl)oxy]pyrimidin-5-yl]-5,5-dimethyl-imidazolidine-2,4-dione (enantiomer 1);
3-[2-[(3-ethyl-1,3-dihydroisobenzofuran-5-yl)oxy]pyrimidin-5-yl]-5,5-dimethyl-imidazolidine-2,4-dione (enantiomer 2);
3-[2-[(3-cyclopropyl-1,3-dihydroisobenzofuran-5-yl)oxy]pyrimidin-5-yl]-5,5-dimethyl-imidazolidine-2,4-dione (enantiomer 1);
3-[2-[(3-cyclopropyl-1,3-dihydroisobenzofuran-5-yl)oxy]pyrimidin-5-yl]-5,5-dimethyl-imidazolidine-2,4-dione (enantiomer 2);
5,5-dimethyl-3-(2-spiro[1H-isobenzofuran-3,1'-cyclobutane]-5-yloxypyrimidin-5-yl)imidazolidine-2,4-dione;
5,5-dimethyl-3-(2-spiro[1H-isobenzofuran-3,1'-cyclopentane]-5-yloxypyrimidin-5-yl)imidazolidine-2,4-dione;
5,5-dimethyl-3-[2-[[3-(trifluoromethyl)-1,3-dihydroisobenzofuran-5-yl]oxy]pyrimidin-5-yl]imidazolidine-2,4-dione (enantiomer 1);
5,5-dimethyl-3-[2-[[3-(trifluoromethyl)-1,3-dihydroisobenzofuran-5-yl]oxy]pyrimidin-5-yl]imidazolidine-2,4-dione (enantiomer 2);
3-[2-[(3,3-dimethyl-2H-benzofuran-5-yl)oxy]pyrimidin-5-yl]-5,5-dimethyl-imidazolidine-2,4-dione;
3-[2-(4,4-dimethylisochroman-6-yl)oxypyrimidin-5-yl]-5,5-dimethyl-imidazolidine-2,4-dione;
(5R)-3-[2-[(3,3-dimethyl-1H-isobenzofuran-5-yl)oxy]pyrimidin-5-yl]-5-ethyl-5-methyl-imidazolidine-2,4-dione;
(5R)-3-[2-[(3,3-diethyl-1H-isobenzofuran-5-yl)oxy]pyrimidin-5-yl]-5-ethyl-5-methyl-imidazolidine-2,4-dione;
(5R)-3-[2-[(3-tert-butyl-1,3-dihydroisobenzofuran-5-yl)oxy]pyrimidin-5-yl]-5-ethyl-5-methyl-imidazolidine-2,4-dione (diastereoisomer 1);
(5R)-3-[2-[(3-tert-butyl-1,3-dihydroisobenzofuran-5-yl)oxy]pyrimidin-5-yl]-5-ethyl-5-methyl-imidazolidine-2,4-dione (diastereoisomer 2);
(5R)-5-ethyl-5-methyl-3-[2-[[3-methyl-3-(trifluoromethyl)-1H-isobenzofuran-5-yl]oxy]pyrimidin-5-yl]imidazolidine-2,4-dione (diastereoisomer 1);
(5R)-5-ethyl-5-methyl-3-[2-[[3-methyl-3-(trifluoromethyl)-1H-isobenzofuran-5-yl]oxy]pyrimidin-5-yl]imidazolidine-2,4-dione (diastereoisomer 2);
(5R)-5-ethyl-3-[2-[(3-ethyl-1,3-dihydroisobenzofuran-5-yl)oxy]pyrimidin-5-yl]-5-methyl-imidazolidine-2,4-dione (diastereoisomer 1);
(5R)-5-ethyl-3-[2-[(3-ethyl-1,3-dihydroisobenzofuran-5-yl)oxy]pyrimidin-5-yl]-5-methyl-imidazolidine-2,4-dione (diastereoisomer 2);
(5R)-3-[2-[(3-cyclopropyl-1,3-dihydroisobenzofuran-5-yl)oxy]pyrimidin-5-yl]-5-ethyl-5-methyl-imidazolidine-2,4-dione (diastereoisomer 1);
(5R)-3-[2-[(3-cyclopropyl-1,3-dihydroisobenzofuran-5-yl)oxy]pyrimidin-5-yl]-5-ethyl-5-methyl-imidazolidine-2,4-dione (diastereoisomer 2);
(5R)-5-ethyl-5-methyl-3-(2-spiro[1H-isobenzofuran-3,1'-cyclobutane]-5-yloxypyrimidin-5-yl)imidazolidine-2,4-dione;
(5R)-5-ethyl-5-methyl-3-(2-spiro[1H-isobenzofuran-3,1'-cyclopentane]-5-yloxypyrimidin-5-yl)imidazolidine-2,4-dione;
(5R)-5-ethyl-5-methyl-3-[2-[[3-(trifluoromethyl)-1,3-dihydroisobenzofuran-5-yl]oxy]pyrimidin-5-yl]imidazolidine-2,4-dione (diastereoisomer 1);
(5R)-5-ethyl-5-methyl-3-[2-[[3-(trifluoromethyl)-1,3-dihydroisobenzofuran-5-yl]oxy]pyrimidin-5-yl]imidazolidine-2,4-dione (diastereoisomer 2);
(5R)-3-[2-[(3,3-dimethyl-2H-benzofuran-5-yl)oxy]pyrimidin-5-yl]-5-ethyl-5-methyl-imidazolidine-2,4-dione;
(5R)-3-[2-(4,4-dimethylisochroman-6-yl)oxypyrimidin-5-yl]-5-ethyl-5-methyl-imidazolidine-2,4-dione;
(5R)-3-[6-[(3,3-dimethyl-1H-isobenzofuran-5-yl)oxy]-3-pyridyl]-5-ethyl-5-methyl-imidazolidine-2,4-dione;
(5R)-3-[6-[(3,3-diethyl-1H-isobenzofuran-5-yl)oxy]-3-pyridyl]-5-ethyl-5-methyl-imidazolidine-2,4-dione;
(5R)-3-[6-[(3-tert-butyl-1,3-dihydroisobenzofuran-5-yl)oxy]-3-pyridyl]-5-ethyl-5-methyl-imidazolidine-2,4-dione (diastereoisomer 1);
(5R)-3-[6-[(3-tert-butyl-1,3-dihydroisobenzofuran-5-yl)oxy]-3-pyridyl]-5-ethyl-5-methyl-imidazolidine-2,4-dione (diastereoisomer 2);
(5R)-5-ethyl-5-methyl-3-[6-[[3-methyl-3-(trifluoromethyl)-1H-isobenzofuran-5-yl]oxy]-3-pyridyl]imidazolidine-2,4-dione (diastereoisomer 1);
(5R)-5-ethyl-5-methyl-3-[6-[[3-methyl-3-(trifluoromethyl)-1H-isobenzofuran-5-yl]oxy]-3-pyridyl]imidazolidine-2,4-dione (diastereoisomer 2);
(5R)-5-ethyl-3-[6-[(3-ethyl-1,3-dihydroisobenzofuran-5-yl)oxy]-3-pyridyl]-5-methyl-imidazolidine-2,4-dione (diastereoisomer 1);
(5R)-5-ethyl-3-[6-[(3-ethyl-1,3-dihydroisobenzofuran-5-yl)oxy]-3-pyridyl]-5-methyl-imidazolidine-2,4-dione (diastereoisomer 2);
(5R)-3-[6-[(3-cyclopropyl-1,3-dihydroisobenzofuran-5-yl)oxy]-3-pyridyl]-5-ethyl-5-methyl-imidazolidine-2,4-dione (diastereoisomer 1);

(5R)-3-[6-[(3-cyclopropyl-1,3-dihydroisobenzofuran-5-yl)oxy]-3-pyridyl]-5-ethyl-5-methyl-imidazolidine-2,4-dione (diastereoisomer 2);
(5R)-5-ethyl-5-methyl-3-(6-spiro[1H-isobenzofuran-3,1'-cyclobutane]-5-yloxy-3-pyridyl)imidazolidine-2,4-dione;
(5R)-5-ethyl-5-methyl-3-(6-spiro[1H-isobenzofuran-3,1'-cyclopentane]-5-yloxy-3-pyridyl)imidazolidine-2,4-dione;
(5R)-5-ethyl-5-methyl-3-[6-[[3-(trifluoromethyl)-1,3-dihydroisobenzofuran-5-yl]oxy]-3-pyridyl]imidazolidine-2,4-dione (diastereoisomer 1);
(5R)-5-ethyl-5-methyl-3-[6-[[3-(trifluoromethyl)-1,3-dihydroisobenzofuran-5-yl]oxy]-3-pyridyl]imidazolidine-2,4-dione (diastereoisomer 2);
(5R)-3-[6-[(3,3-dimethyl-2H-benzofuran-5-yl)oxy]-3-pyridyl]-5-ethyl-5-methyl-imidazolidine-2,4-dione;
(5R)-3-[6-(4,4-dimethylisochroman-6-yl)oxy-3-pyridyl]-5-ethyl-5-methyl-imidazolidine-2,4-dione;
3-[6-[(3,3-diethyl-1H-isobenzofuran-5-yl)oxy]-3-pyridyl]-5,5-dimethyl-imidazolidine-2,4-dione;
3-[6-[(3-tert-butyl-1,3-dihydroisobenzofuran-5-yl)oxy]-3-pyridyl]-5,5-dimethyl-imidazolidine-2,4-dione (enantiomer 1);
3-[6-[(3-tert-butyl-1,3-dihydroisobenzofuran-5-yl)oxy]-3-pyridyl]-5,5-dimethyl-imidazolidine-2,4-dione (enantiomer 2);
5,5-dimethyl-3-[6-[[3-methyl-3-(trifluoromethyl)-1H-isobenzofuran-5-yl]oxy]-3-pyridyl]imidazolidine-2,4-dione (enantiomer 1);
5,5-dimethyl-3-[6-[[3-methyl-3-(trifluoromethyl)-1H-isobenzofuran-5-yl]oxy]-3-pyridyl]imidazolidine-2,4-dione (enantiomer 2);
3-[6-[(3-ethyl-1,3-dihydroisobenzofuran-5-yl)oxy]-3-pyridyl]-5,5-dimethyl-imidazolidine-2,4-dione (enantiomer 1);
3-[6-[(3-ethyl-1,3-dihydroisobenzofuran-5-yl)oxy]-3-pyridyl]-5,5-dimethyl-imidazolidine-2,4-dione (enantiomer 2);
3-[6-[(3-cyclopropyl-1,3-dihydroisobenzofuran-5-yl)oxy]-3-pyridyl]-5,5-dimethyl-imidazolidine-2,4-dione (enantiomer 1);
3-[6-[(3-cyclopropyl-1,3-dihydroisobenzofuran-5-yl)oxy]-3-pyridyl]-5,5-dimethyl-imidazolidine-2,4-dione (enantiomer 2);
5,5-dimethyl-3-(6-spiro[1H-isobenzofuran-3,1'-cyclobutane]-5-yloxy-3-pyridyl)imidazolidine-2,4-dione;
5,5-dimethyl-3-(6-spiro[1H-isobenzofuran-3,1'-cyclopentane]-5-yloxy-3-pyridyl)imidazolidine-2,4-dione;
5,5-dimethyl-3-[6-[[3-(trifluoromethyl)-1,3-dihydroisobenzofuran-5-yl]oxy]-3-pyridyl]imidazolidine-2,4-dione (enantiomer 1);
5,5-dimethyl-3-[6-[[3-(trifluoromethyl)-1,3-dihydroisobenzofuran-5-yl]oxy]-3-pyridyl]imidazolidine-2,4-dione (enantiomer 2);
3-[6-[(3,3-dimethyl-2H-benzofuran-5-yl)oxy]-3-pyridyl]-5,5-dimethyl-imidazolidine-2,4-dione;
3-[6-(4,4-dimethylisochroman-6-yl)oxy-3-pyridyl]-5,5-dimethyl-imidazolidine-2,4-dione;
(5R)-3-[6-[(3,3-dimethyl-1H-isobenzofuran-5-yl)oxy]-5-methyl-3-pyridyl]-5-ethyl-5-methyl-imidazolidine-2,4-dione;
(5R)-5-ethyl-5-methyl-3-[5-methyl-6-[[3-methyl-3-(trifluoromethyl)-1H-isobenzofuran-5-yl]oxy]-3-pyridyl]imidazolidine-2,4-dione (diastereoisomer 1);
(5R)-5-ethyl-5-methyl-3-[5-methyl-6-[[3-methyl-3-(trifluoromethyl)-1H-isobenzofuran-5-yl]oxy]-3-pyridyl]imidazolidine-2,4-dione (diastereoisomer 2);
(5R)-5-ethyl-5-methyl-3-(5-methyl-6-spiro[1H-isobenzofuran-3,1'-cyclobutane]-5-yloxy-3-pyridyl)imidazolidine-2,4-dione;
(5R)-5-ethyl-5-methyl-3-[5-methyl-6-[[3-(trifluoromethyl)-1,3-dihydroisobenzofuran-5-yl]oxy]-3-pyridyl]imidazolidine-2,4-dione (diastereoisomer 1);
(5R)-5-ethyl-5-methyl-3-[5-methyl-6-[[3-(trifluoromethyl)-1,3-dihydroisobenzofuran-5-yl]oxy]-3-pyridyl]imidazolidine-2,4-dione (diastereoisomer 2);
5,5-dimethyl-3-(5-methyl-6-{[3-(trifluoromethyl)-1,3-dihydro-2-benzofuran-5-yl]oxy}pyridin-3-yl)imidazolidine-2,4-dione (enantiomer 1);
5,5-dimethyl-3-(5-methyl-6-{[3-(trifluoromethyl)-1,3-dihydro-2-benzofuran-5-yl]oxy}pyridin-3-yl)imidazolidine-2,4-dione (enantiomer 2);
(5R)-3-[6-[(3,3-dimethyl-1H-isobenzofuran-5-yl)oxy]-3-pyridyl]-5-ethyl-imidazolidine-2,4-dione;
(5R)-5-ethyl-3-[6-[[3-methyl-3-(trifluoromethyl)-1H-isobenzofuran-5-yl]oxy]-3-pyridyl]imidazolidine-2,4-dione (diastereoisomer 1);
(5R)-5-ethyl-3-[6-[[3-methyl-3-(trifluoromethyl)-1H-isobenzofuran-5-yl]oxy]-3-pyridyl]imidazolidine-2,4-dione (diastereoisomer 2);
(5R)-5-ethyl-3-(6-spiro[1H-isobenzofuran-3,1'-cyclobutane]-5-yloxy-3-pyridyl)imidazolidine-2,4-dione;
(5R)-3-[6-[(3,3-dimethyl-2H-benzofuran-5-yl)oxy]-3-pyridyl]-5-ethyl-imidazolidine-2,4-dione;
(5R)-5-ethyl-3-[2-[[3-methyl-3-(trifluoromethyl)-1H-isobenzofuran-5-yl]oxy]pyrimidin-5-yl]imidazolidine-2,4-dione (diastereoisomer 1);
(5R)-5-ethyl-3-[2-[[3-methyl-3-(trifluoromethyl)-1H-isobenzofuran-5-yl]oxy]pyrimidin-5-yl]imidazolidine-2,4-dione (diastereoisomer 2);
(5R)-5-ethyl-3-(2-spiro[1H-isobenzofuran-3,1'-cyclobutane]-5-yloxypyrimidin-5-yl)imidazolidine-2,4-dione;
(5R)-3-{4-[(3,3-dimethyl-1,3-dihydro-2-benzofuran-5-yl)oxy]phenyl}-5-ethyl-5-methyl-2,4-imidazolidinedione; and
(5R)-3-[4-(1,3-dihydro-2-benzofuran-5-yloxy)phenyl]-5-methyl-2,4-imidazolidinedione.

For the avoidance of doubt, the embodiments of any one feature of the compounds of the invention may be combined with any embodiment of another feature of compounds of the invention to create a further embodiment.

The term 'halo' or 'halogen' as used herein, refers to a fluorine, chlorine, bromine or iodine atom. Particular examples of halo are fluorine and chlorine, especially fluorine.

When the compound contains a $C_{1-4}$alkyl group, whether alone or forming part of a larger group, e.g. $C_{1-4}$alkoxy, the alkyl group may be straight chain, branched, cyclic, or a combination thereof. Examples of $C_{1-4}$alkyl are methyl, ethyl, n-propyl, isopropyl, n-butyl, isobutyl, sec-butyl, tert-butyl, cyclopropyl and cyclobutyl. A particular group of exemplary $C_{1-4}$alkyl groups are methyl, ethyl, n-propyl, isopropyl, n-butyl, isobutyl, sec-butyl, tert-butyl. An example of $C_{1-4}$alkoxy is methoxy. $C_{1-5}$alkyl extends the definition of $C_{1-4}$alkyl to include alkyl groups having five carbon atoms, such as pentyl.

The term 'halo$C_{1-4}$alkyl' as used herein, includes straight chain, branched chain or cyclic alkyl groups containing 1 to 4 carbon atoms substituted by one or more halo atoms, for example fluoromethyl, difluoromethyl and trifluoromethyl. A particular group of exemplary halo$C_{1-4}$ alkyl include methyl and ethyl groups substituted with one to three halo atoms, in particular one to three fluoro atoms, such as trifluoromethyl or 2,2,2-trifluoroethyl. HaloC$_{1-5}$alkyl extends the definition of haloC$_{1-4}$alkyl to include haloalkyl groups having five carbon atoms.

The term 'haloC$_{1-4}$alkoxy' as used herein, includes straight chain, branched chain or cyclic alkoxy groups containing 1 to 4 carbon atoms substituted by one or more halo atoms, for example fluoromethoxy, difluoromethoxy and trifluoromethoxy. A particular group of exemplary haloC$_{1-4}$oxyalkyl include methoxy and ethoxy groups substituted with one to three halo atoms, in particular one to three fluoro atoms.

The term '5 or 6 membered saturated or unsaturated heterocycle, with at least one O atom' includes for example furan, oxazole, isoxzole, oxadiazole, terahydrofuran, pyran, tetrahydropyran, dioxolane, dioxan, morpholine, and oxazoline.

It will be appreciated that for use in medicine the salts of the compounds of formula (I) should be pharmaceutically acceptable. Suitable pharmaceutically acceptable salts will be apparent to those skilled in the art. Pharmaceutically acceptable salts include those described by Berge, Bighley and Monkhouse J. Pharm. Sci. (1977) 66, pp 1-19. Such pharmaceutically acceptable salts include acid addition salts formed with inorganic acids e.g. hydrochloric, hydrobromic, sulphuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates, may be used, for example in the isolation of compounds of formula (I) and are included within the scope of this invention.

Certain of the compounds of formula (I) may form acid addition salts with one or more equivalents of the acid. The present invention includes within its scope all possible stoichiometric and non-stoichiometric forms.

The compounds of formula (I) may be prepared in crystalline or non-crystalline form and, if crystalline, may optionally be solvated, e.g. as the hydrate. This invention includes within its scope stoichiometric solvates (e.g. hydrates) as well as compounds containing variable amounts of solvent (e.g. water).

It will be understood that the invention includes pharmaceutically acceptable derivatives of compounds of formula (I) and that these are included within the scope of the invention.

As used herein "pharmaceutically acceptable derivative" includes any pharmaceutically acceptable prodrug such as an ester or salt of such ester of a compound of formula (I) which, upon administration to the recipient is capable of providing (directly or indirectly) a compound of formula (I) or an active metabolite or residue thereof.

Suitably, a pharmaceutically acceptable prodrug is formed by functionalising the secondary nitrogen of the hydantoin, for example with a group "L" as illustrated below:

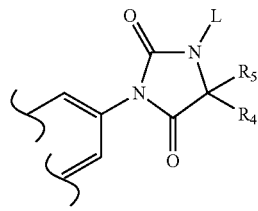

In one embodiment of the invention, a compound of formula (I) is functionalised via the secondary nitrogen of the hydantoin with a group L, wherein L is selected from:

a) —PO(OH)O$^-$.M$^+$, wherein M$^+$ is a pharmaceutically acceptable monovalent counterion,
b) —PO(O$^-$)$_2$.2M$^+$,
c) —PO(O$^-$)$_2$.D$^{2+}$, wherein D$^{2+}$ is a pharmaceutically acceptable divalent counterion,
d) —CH(R$^X$)—PO(OH)O$^-$.M$^+$, wherein R$^X$ is hydrogen or C$_{1-3}$ alkyl,
e) —CH(R$^X$)—PO(O$^-$)$_2$.2M$^+$,
f) —CH(R$^X$)—PO(O$^-$)$_2$.D$^{2+}$
g) —SO$_3^-$.M$^+$,
h) —CH(R$^X$)—SO$_3^-$.M$^+$, and
i) —CO—CH$_2$CH$_2$—CO$_2$.M$^+$.

It is to be understood that the present invention encompasses all isomers of formula (I) and their pharmaceutically acceptable derivatives, including all geometric, tautomeric and optical forms, and mixtures thereof (e.g. racemic mixtures). Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

The subject invention also includes isotopically-labelled compounds which are identical to those recited in formula (I) but for the fact that one or more atoms are replaced by an atom having an atomic mass or mass number different from the atomic mass or mass number most commonly found in nature. The skilled person will appreciate that in many circumstances the proportion of an atom having an atomic mass or mass number found less commonly in nature can also be been increased (referred to as "isotopic enrichment"). Examples of isotopes that can be incorporated into compounds of the invention include isotopes of hydrogen, carbon, nitrogen, oxygen, fluorine, iodine and chlorine such as $^3$H, $^{11}$C, $^{14}$C, $^{18}$F, $^{123}$I or $^{125}$I. Another isotope of interest is $^{13}$C. Another isotope of interest is $^2$H (deuterium).

Compounds of the present invention and pharmaceutically acceptable salts of said compounds that contain the aforementioned isotopes and/or other isotopes of other atoms are within the scope of the present invention. Isotopically labelled compounds of the present invention, for example those into which radioactive isotopes such as $^3$H or $^{14}$C have been incorporated, are useful in drug and/or substrate tissue distribution assays. Tritiated, i.e. $^3$H, and carbon-14, i.e. $^{14}$C, isotopes are particularly preferred for their ease of preparation and detectability. $^{11}$C and $^{18}$F isotopes are particularly useful in PET (positron emission tomography).

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

According to a further aspect of the present invention there is provided a process for the preparation of compounds of formula (I) and derivatives thereof. The following schemes detail synthetic routes to compounds of the invention. In the following schemes reactive groups can be protected with protecting groups and deprotected according to well established techniques.

In general, the compounds of formula (I) may be made according to the organic synthesis techniques known to those skilled in this field, as well as by the representative methods set forth below, those in the Examples, and modifications thereof.

Compounds of formula (I), and salts and solvates thereof, may be prepared by the general methods outlined hereinafter. In the following description, the groups A, $R_1$, $R_2$, X, Y, $R_3$, $R_4$, $R_5$, $R_{13}$, $R_{14}$ and $R_{15}$ have the meanings as previously defined for compounds of formula (I) unless otherwise stated.

Scheme 1

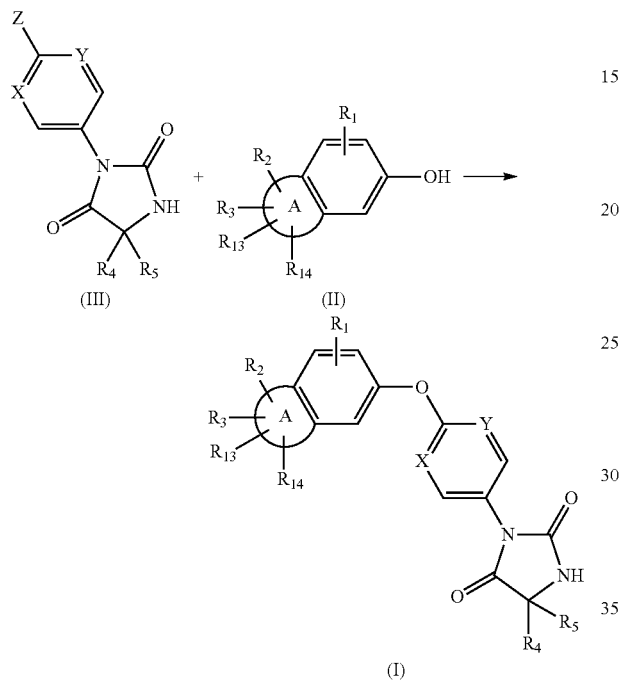

Compounds of formula (I) wherein X=N and Y=$CR_{15}$ or N can be prepared by nucleophilic aromatic substitution. In this reaction are used a pyridine or pyrimidine derivative of formula (III) wherein Z=F or Cl and a phenol of formula (II) in presence of a base such as potassium carbonate in a solvent e.g. in N,N-dimethylformamide or acetonitrile or N-methylpyrrolidone with regular heating or microwave heating at temperature ranging from 60° C. to reflux.

Scheme 2

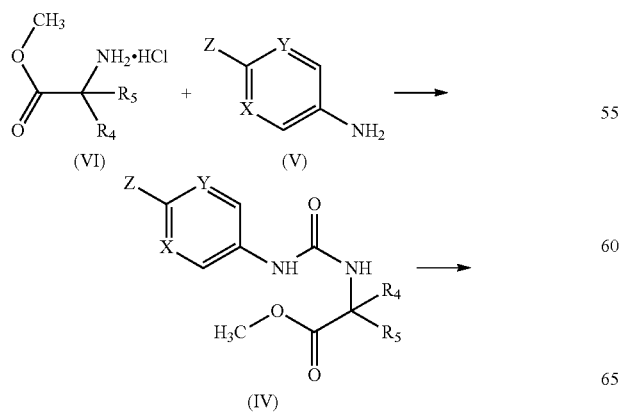

-continued

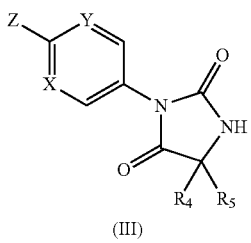

Step (ii):

Compounds of formula (III) can be prepared by reaction of ureas of formula (IV) and a base such as sodium methoxide in a solvent such as methanol at temperature ranging from 0° C. to 60° C.

step (i):

Ureas of formula (IV) can be prepared by reaction of commercially available anilines of formula (v), wherein Z is F or Cl, and amino esters (hydrochloride salt) of formula (VI) in a solvent e.g. dichloromethane or ethyl acetate with a carbonylating agent e.g. triphosgene preferentially prediluted in the same solvent in presence of a base e.g. triethylamine or diisopropylethylamine at temperature ranging from 0° C. to 60° C., optionally adding a catalytic or stoichiometric amount of DMAP.

Scheme 3

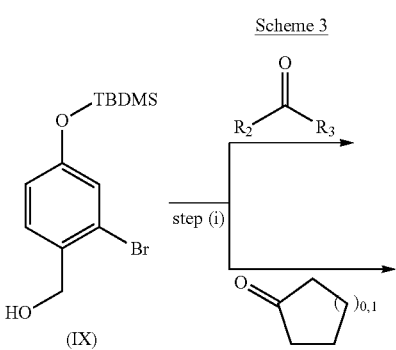

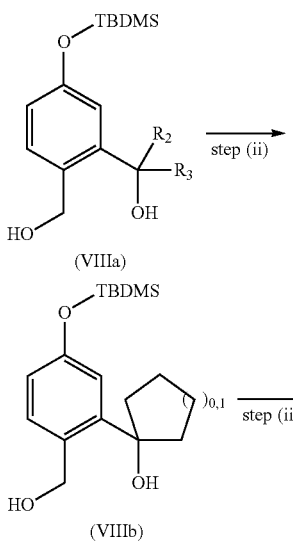

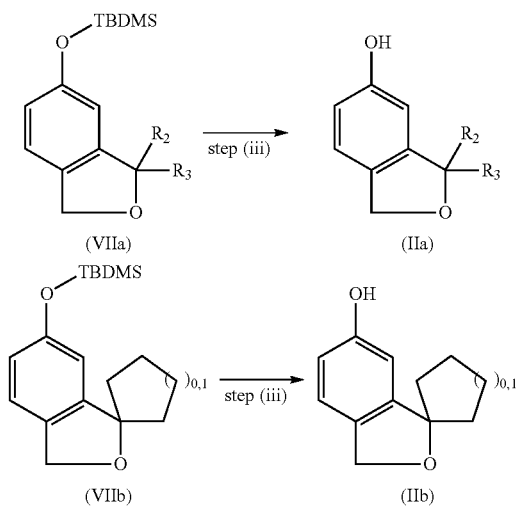

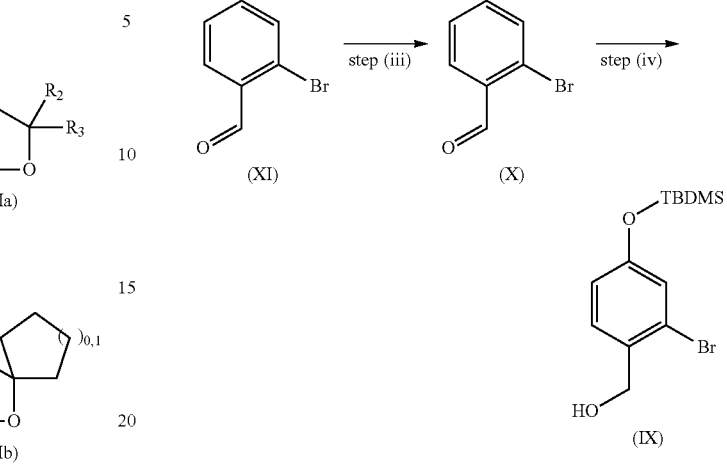

Step (iii):

Phenol of formula (IIa) and (IIb) can be prepared from TBDMS protected compounds of formula (VII) removing the protective group in presence of a fluoride source such as tetrabutylammonium fluoride in a suitable solvent such as THF at temperature ranging from 0° C. to room temperature.

step (ii):

Compounds of formula (VII) can be prepared by cyclisation of compounds of formula (VIII) using a base such as nBuLi in a solvent such as THF e.g. at 0° C., adding in a second time 4-methylbenzenesulfonyl chloride e.g. at 0° C., then a second equivalent of a base such as nBuLi e.g. from 0° C. to room temperature.

Optionally the two steps (ii) and (iii) can be carried out in a one pot fashion.

Step (i):

compounds of formula (VIII) be prepared from compounds of formula (IX) by metal-halogen exchange using 2 equivalents of butyllithium in a suitable solvent such as hexane or THF, or a mixture of them, at temperature ranging from −78° C. to room temperature and adding in a second stage a suitable carbonylic compound (aldehyde or ketone) at temperature ranging from −78° C. to room temperature.

Step (iv):

Alcohols of formula (IX) can be prepared from aldehyde of formula (X) using a reductive reagent such as lithium aluminium hydride in a suitable solvent such as THF at 0° C. or sodium borohydride in a suitable solvent such as methanol at 0° C.

Step (iii):

Compound of formula (X) can be prepared from compound of formula (XI) by silylation, using for example chloro(1,1-dimethylethyl)dimethylsilane, 1H imidazole in a solvent such as dichloromethane at room temperature.

Step (ii):

Aldehyde of formula (XI) can be prepared from cyano derivative of formula (XII) using a reductive reagent such as diisobutyl aluminumhydride in a suitable solvent such as THF, dichloromethane or toluene, or a mixture of them, at 0° C.

Step (i):

Phenol of formula (XII) can be prepared by nucleophilic aromatic substitution. In this reaction are used a fluoro derivative of formula (XIII) and potassium trimethylsilanolate in a solvent e.g. in N,N-dimethylformamide or in acetonitrile with regular heating or microwave one at temperature ranging from room temperature to reflux.

Scheme 4

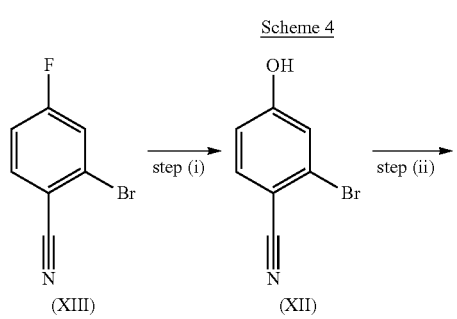

Scheme 5

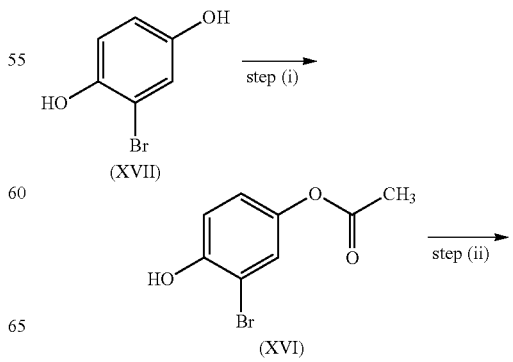

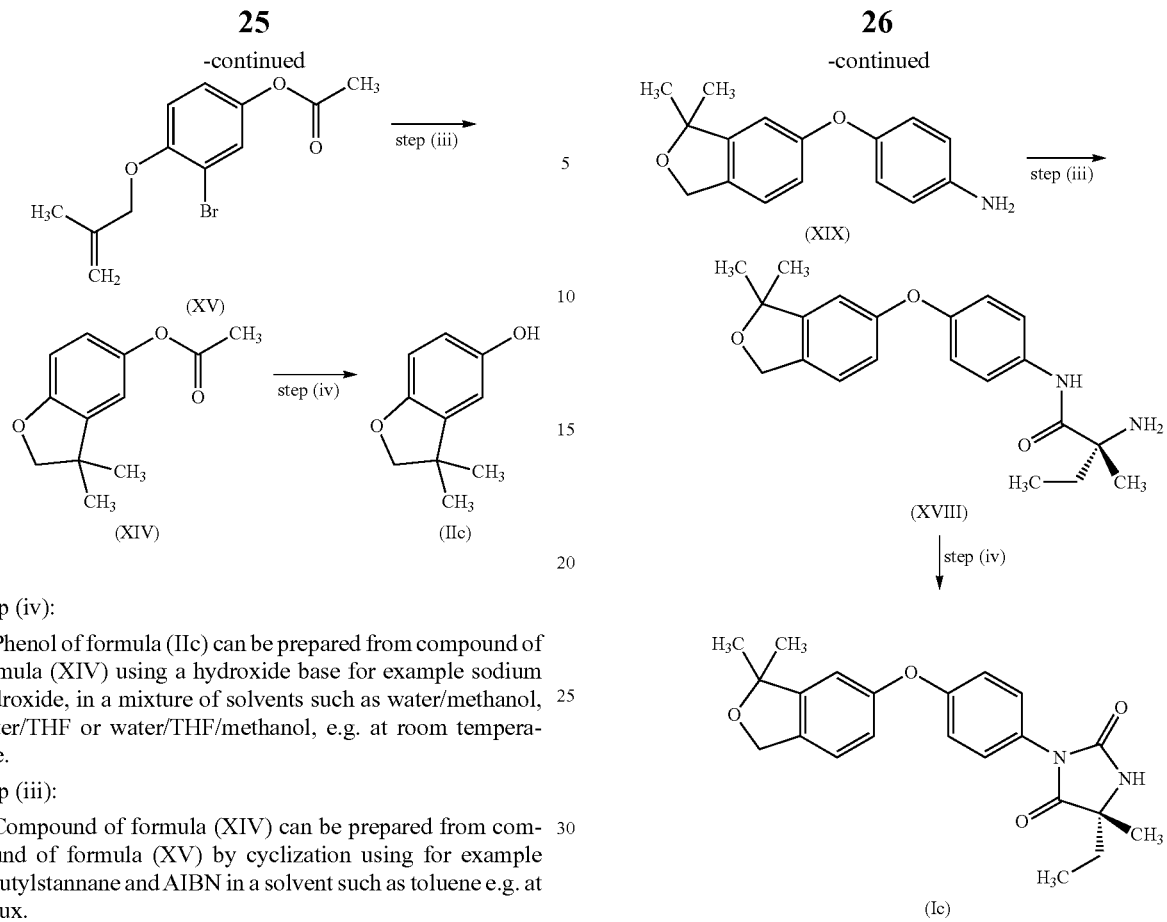

Step (iv):

Phenol of formula (IIc) can be prepared from compound of formula (XIV) using a hydroxide base for example sodium hydroxide, in a mixture of solvents such as water/methanol, water/THF or water/THF/methanol, e.g. at room temperature.

Step (iii):

Compound of formula (XIV) can be prepared from compound of formula (XV) by cyclization using for example tributylstannane and AIBN in a solvent such as toluene e.g. at reflux.

Step (ii):

Compound of formula (XV) can be prepared from compound of formula (XVI) using a base such as potassium carbonate and an electrophile such as 3-bromo-2-methyl-1-propene, in a solvent such as acetonitrile e.g. at temperature ranging from room temperature to reflux.

Step (i):

Compound of formula (XVI) can be prepared from compound of formula (XVII) by acetylation using for example acetic anhydride and a base e.g. triethylamine in a solvent e.g. dichloromethane e.g. at room temperature.

Scheme 6

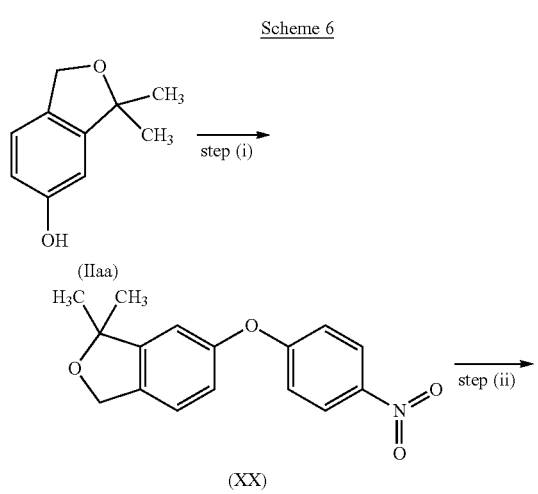

Step (iv):

compound of formula (Ic) corresponding to compound of formula (I) wherein X=CH, Y=CH and $R_1$ is H can be prepared from compound of formula (XVIII) by using carbonyl diimidazole in a suitable solvent such as ethyl acetate at room temperature.

Step (iii):

Compound of formula (XVIII) can be prepared by reaction of aniline of formula (XIX) with methyl-D-isovalinic acid hydrochloride in presence of a coupling agent such as T3P in a suitable solvent such as acetonitrile or ethyl acetate or a mixture of them at temperature ranging from room temperature to reflux.

Step (ii):

Aniline of formula (XIX) can be prepared by reduction of nitro derivative of formula (XX) using:

Pd/C in hydrogen atmosphere in a suitable solvent such as methanol or ethanol at pressure ranging from 1 atm to 5 atm at room temperature;

Iron in presence of hydrogen chloride in a mixture of solvent such as ethanol/water or THF/water.

Step (i):

Nitro derivative of formula (XX) can be prepared by aromatic nucleophilic substitution using phenol of formula (IIaa) wherein $R_2$ and $R_3$ are methyl and commercially available 4-fluoro nitrobenzene in presence of a base such as potassium carbonate in a solvent such as acetonitrile or DMF at temperature ranging from room temperature to reflux.

Scheme 7

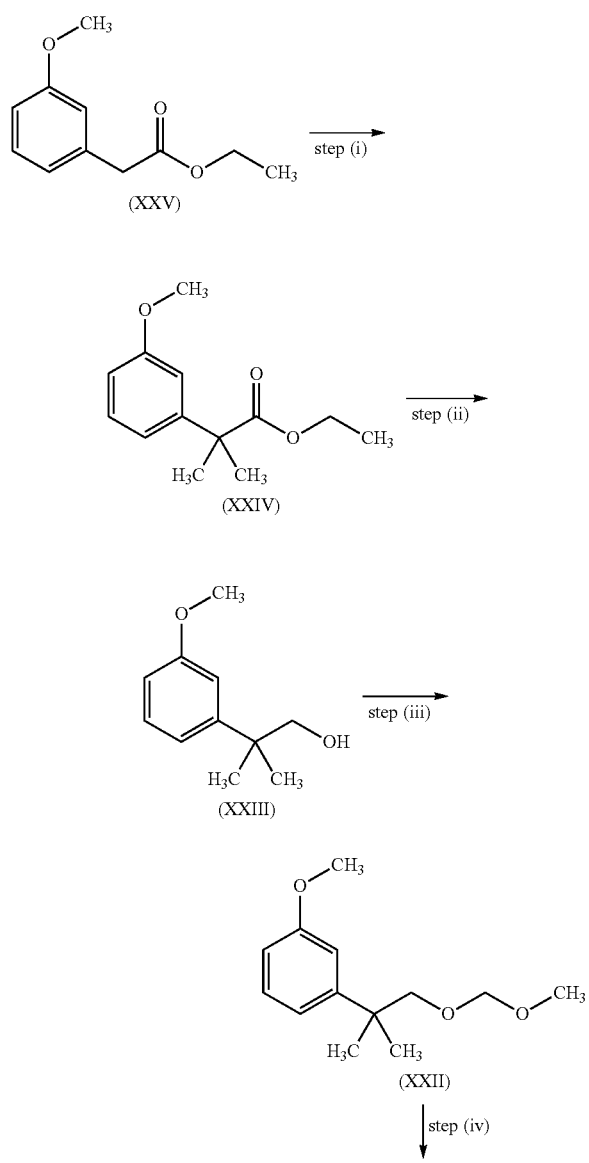

Step (v):

Phenol of formula (IId) can be prepared from compound of formula (XXI) by reaction with tribromoborane in a suitable solvent such as dichloromethane at temperature ranging from 0° C. to room temperature.

Step (iv):

compound of formula (XXI) can be prepared by cyclization of compound of formula (XXII) using titanium tetrachloride in a suitable solvent such as dichloromethane at temperature ranging from −78° C. to room temperature.

Step (iii):

compound of formula (XXII) can be prepared from alcohol of formula (XXIII) using a base such as sodium hydride in a suitable solvent such as THF and chloro(methoxy)methane at temperature ranging from room temperature to reflux.

Step (ii):

alcohol of formula (XXIII) can be prepared from ester of formula (XXIV) using a reductive reagent such as lithium aluminium hydride in a suitable solvent such as THF at 0° C.

Step (i):

ester of formula (XXIV) can be prepared from commercially available ethyl 2-(3-methoxyphenyl)acetate of formula (XXV) using a base such as sodium hydride in a suitable solvent such as THF and adding in a second time a methylating agent such as iodomethane at temperature ranging from 0° C. to room temperature.

Scheme 8

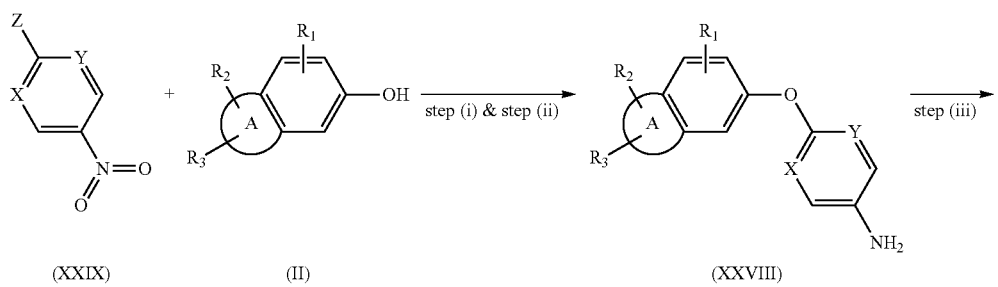

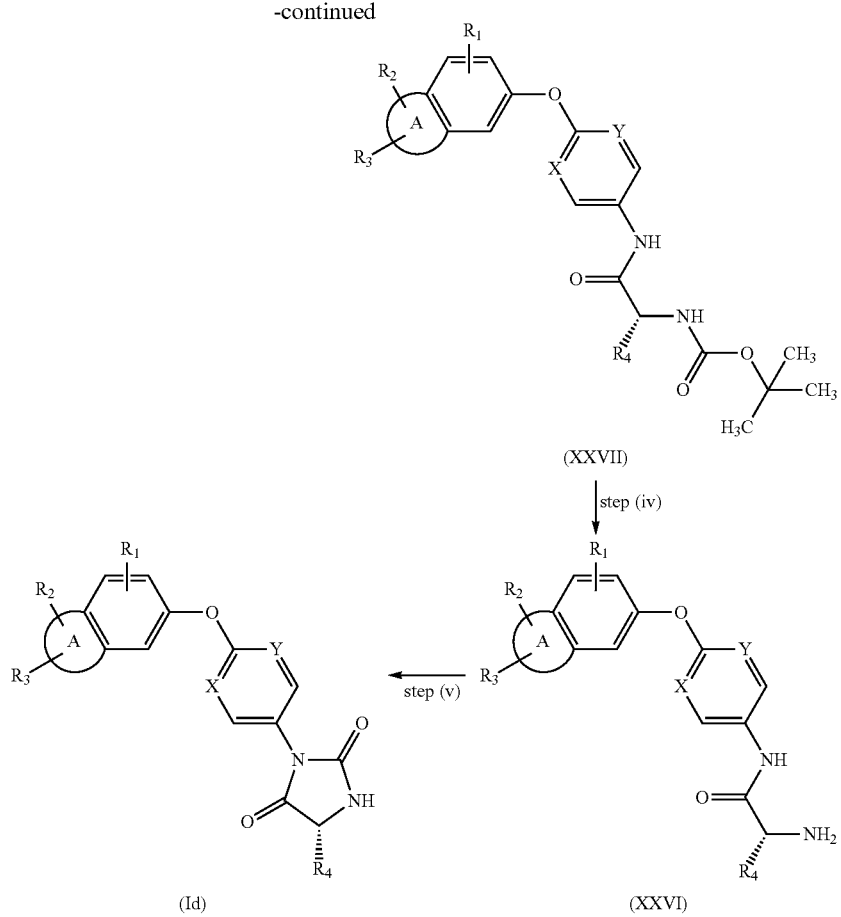

(XXVII)

(Id)  (XXVI)

Step (v):

Compounds of formula (Id) corresponding to compound of formula (I) wherein R₄ is methyl or ethyl and R₅ is H can be prepared from amino amide of formula (XXVI) by cyclisation using a carbonilating agent such as triphosgene in presence of a base such as triethylamine in a suitable solvent such as dichloromethane or ethyl acetate at temperature ranging from 0° C. to room temperature.

Step (iv):

amino amides of formula (XXVI) can be prepared from boc-protected compound of formula (XXVII) by reaction with trifluoroacetic acid in a suitable solvent such as dichloromethane at temperature ranging from 0° C. to room temperature.

Step (iii):

compounds of formula (XXVII) can be prepared from anilines of formula (XXVIII) and (2R)-2-[(tert-butoxycarbonyl)amino]butanoic acid (R₄=ethyl) or (2R)-2-[(tert-butoxycarbonyl)amino]propanoic acid (R₄=methyl) in presence of a base such as diisopropylethylamine and a coupling agent such as HATU or TBTU in a suitable solvent such as DMF at temperature ranging from room temperature to reflux.

Step (i) and Step (ii):

Anilines of formula (XXVIII) can be prepared by:
aromatic nucleophilic substitution using phenol of formula (II) and a nitro derivative of formula (XXIX) in presence of a base such as potassium carbonate in a solvent such as acetonitrile or DMF at temperature ranging from room temperature to reflux followed by reduction of the obtained nitro derivative using:

Pd/C in hydrogen atmosphere in a suitable solvent such as methanol or ethanol at pressure ranging from 1 atm to 5 atm at room temperature;

Iron in presence of hydrogen chloride in a mixture of solvent such as ethanol/water or THF/water.

Scheme 9

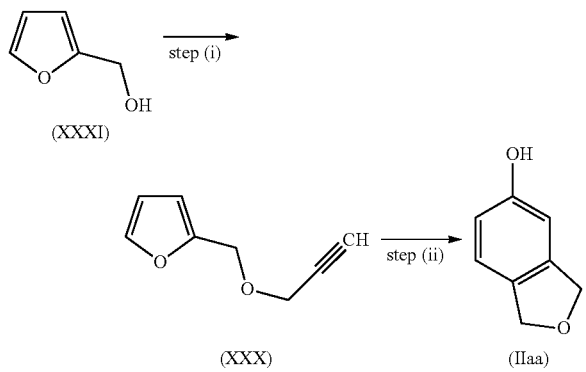

Step (ii):

Phenols of formula (IIaa) corresponding to phenol of formula (IIa) wherein R₂=R₃=H can be prepared by an intramolecular reaction from compounds of formula (XXX) in presence of a catalytic amount of AuCl₃ in acetonitrile at r.t.

or a catalytic amount of PtCl$_2$ in acetone with heating (as described in the Journal of the American Chemical Society 2003, 125, 5757-5766)

Step (i):

Compound of formula (XXX) can be prepared from compound of formula (XXXI) by nucleophilic substitution in presence of a base such as sodium hydride in a solvent such as DMF followed by the addition of the electrophile 3-bromo-1-propyne.

The present invention provides compounds of formula (I) or a pharmaceutically acceptable salt thereof for use in therapy.

The compounds of formula (I) or their pharmaceutically acceptable salts and/or solvates may be of use for the treatment or prophylaxis of a disease or disorder where a modulator of the Kv3.1 or Kv3.2 or Kv3.1 and Kv3.2 channels is required. As used herein, a modulator of Kv3.1 or Kv3.2 or Kv3.1 and Kv3.2 is a compound which alters the properties of these channels, either positively or negatively. Compounds of the invention may be tested in the assay of Biological Example 1 to determine their modulatory properties.

In certain disorders it may be of benefit to utilise a modulator of Kv3.1 or Kv3.2 which demonstrates a particular selectivity profile between the two channels. For example a compound may be selective for modulation of Kv3.1 channels over modulation of Kv3.2 channels demonstrating, for example, at least a 2 fold, 5 fold or 10 fold activity for Kv3.1 channels than for Kv3.2 channels. Alternatively, a compound may be selective for modulation of Kv3.2 channels over modulation of Kv3.1 channels demonstrating, for example, at least a 2 fold, 5 fold or 10 fold activity for Kv3.2 channels than for Kv3.1 channels. In other cases a compound may demonstrate comparable activity between modulation of Kv3.1 and Kv3.2 channels, for example the activity for each channel is less than 2 fold that for the other channel, such as less than 1.5 fold or less than 1.2 fold. The activity of a compound is suitably quantified by its potency as indicated by an EC$_{50}$ value.

Diseases or conditions that may be mediated by modulation of Kv3.1 and/or Kv3.2 channels may be selected from the list below. The numbers in brackets after the listed diseases below refer to the classification code in Diagnostic and Statistical Manual of Mental Disorders, 4th Edition, published by the American Psychiatric Association (DSM-IV) and/or the International Classification of Diseases, 10th Edition (ICD-10).

The compounds of formula (I) or their pharmaceutically acceptable salts and/or solvates may be of use for the treatment or prophylaxis of depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90);

Seasonal Affective Disorder.

The compounds of formula (I) or their pharmaceutically acceptable salts and/or solvates may be of use for the treatment or prophylaxis of schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

The compounds of formula (I) or their pharmaceutically acceptable salts and/or solvates may be of use for the treatment or prophylaxis of anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Post-traumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00).

The compounds of formula (I) or their pharmaceutically acceptable salts and/or solvates may be of use for the treatment or prophylaxis of substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

The compounds of formula (I) or their pharmaceutically acceptable salts and/or solvates may be of use for the enhancement of cognition including the treatment of cognition impairment in other diseases such as schizophrenia, bipolar disorder, depression, other psychiatric disorders and psychotic conditions associated with cognitive impairment, e.g. Alzheimer's disease. Alternatively, the compounds of formula (I) or their pharmaceutically acceptable salts and/or solvates may be of use for the prophylaxis of cognition impairment, such as may be associated with diseases such as schizophrenia, bipolar disorder, depression, other psychiatric disorders and psychotic conditions associated with cognitive impairment, e.g. Alzheimer's disease.

The compounds of formula (I) or their pharmaceutically acceptable salts and/or solvates may be of use for the treatment or prophylaxis of sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome.

The compounds of formula (I) or their pharmaceutically acceptable salts and/or solvates may be of use for the treatment or prophylaxis of eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; Binge Eating Disorder; and Eating Disorder Not Otherwise Specified (307.50).

The compounds of formula (I) or their pharmaceutically acceptable salts and/or solvates may be of use for the treatment or prophylaxis of Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism).

The compounds of formula (I) or their pharmaceutically acceptable salts and/or solvates may be of use for the treatment or prophylaxis of Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23).

The compounds of formula (I) or their pharmaceutically acceptable salts and/or solvates may be of use for the treatment or prophylaxis of Personality Disorders including the subtypes Paranoid Personality Disorder (301.0), Schizoid Personality Disorder (301.20), Schizotypal Personality Disorder (301.22), Antisocial Personality Disorder (301.7), Borderline Personality Disorder (301.83), Histrionic Personality Disorder (301.50), Narcissistic Personality Disorder (301.81), Avoidant Personality Disorder (301.82), Dependent Personality Disorder (301.6), Obsessive-Compulsive Personality Disorder (301.4) and Personality Disorder Not Otherwise Specified (301.9).

The compounds of formula (I) or their pharmaceutically acceptable salts and/or solvates may be of use for the treatment or prophylaxis of Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

The compounds of formula (I) or their pharmaceutically acceptable salts and/or solvates may be of use for the treatment or prophylaxis of Impulse control disorder including: Intermittent Explosive Disorder (312.34), Kleptomania (312.32), Pathological Gambling (312.31), Pyromania (312.33), Trichotillomania (312.39), Impulse-Control Disorders Not Otherwise Specified (312.3), Binge Eating, Compulsive Buying, Compulsive Sexual Behaviour and Compulsive Hoarding.

The compounds of formula (I) or their pharmaceutically acceptable salts and/or solvates may be of use for the treatment or prophylaxis of hearing disorders including auditory neuropathy, auditory processing disorder, hearing loss, which includes sudden hearing loss, noise induced hearing loss, substance-induced hearing loss, and hearing loss in adults over 60 (presbycusis), and tinnitus.

The compounds of formula (I) or their pharmaceutically acceptable salts and/or solvates may be of use for the treatment or prophylaxis of Ménière's disease, disorders of balance, and disorders of the inner ear.

The compounds of formula (I) or their pharmaceutically acceptable salts and/or solvates may be of use for the treatment or prophylaxis of hyperacusis and disturbances of loudness perception, including Fragile-X syndrome and autism.

The compounds of formula (I) or their pharmaceutically acceptable salts and/or solvates may be of use for the treatment or prophylaxis of Epilepsy, (including, but not limited to, localization-related epilepsies, generalized epilepsies, epilepsies with both generalized and local seizures, and the like), seizures associated with Lennox-Gastaut syndrome, seizures as a complication of a disease or condition (such as seizures associated with encephalopathy, phenylketonuria, juvenile Gaucher's disease, Lundborg's progressive myoclonic epilepsy, stroke, head trauma, stress, hormonal changes, drug use or withdrawal, alcohol use or withdrawal, sleep deprivation, fever, infection, and the like), essential tremor, restless limb syndrome, partial and generalised seizures (including tonic, clonic, tonic-clonic, atonic, myoclonic, absence seizures), secondarily generalized seizures, temporal lobe epilepsy, absence epilepsies (including childhood, juvenile, myoclonic, photo- and pattern-induced), severe epileptic encephalopathies (including hypoxia-related and Rasmussen's syndrome), febrile convulsions, epilepsy partialis continua, progressive myoclonus epilepsies (including Unverricht-Lundborg disease and Lafora's disease), post-traumatic seizures/epilepsy including those related to head injury, simple reflex epilepsies (including photosensitive, somatosensory and proprioceptive, audiogenic and vestibular), metabolic disorders commonly associated with epilepsy such as pyridoxine-dependent epilepsy, Menkes' kinky hair disease, Krabbe's disease, epilepsy due to alcohol and drug abuse (e.g. cocaine), cortical malformations associated with epilepsy (e.g. double cortex syndrome or subcortical band heterotopia), chromosomal anomalies associated with seizures or epilepsy such as Partial monosomy (15Q)/Angelman syndrome).

In one embodiment of the invention, there is provided a compound of formula (I) or a pharmaceutically acceptable salt and/or solvate thereof for the treatment or prophylaxis of depression and mood disorders, hearing disorders, schizophrenia, substance abuse disorders, sleep disorders or epilepsy.

In one embodiment of the invention, there is provided a compound of formula (I) or a pharmaceutically acceptable salt and/or solvate thereof for the treatment or prophylaxis of bipolar disorder or mania.

In one embodiment of the invention, there is provided a compound of formula (I) or a pharmaceutically acceptable salt and/or solvate thereof for the treatment or prophylaxis of ataxia, such as spinocerebellar ataxia.

In one embodiment of the invention, there is provided a compound of formula (I) or a pharmaceutically acceptable salt and/or solvate thereof for the treatment or prophylaxis of cognition impairment.

The term "treatment" or "treating" as used herein includes the control, mitigation, reduction, or modulation of the disease state or its symptoms.

The term "prophylaxis" is used herein to mean preventing symptoms of a disease or disorder in a subject or preventing recurrence of symptoms of a disease or disorder in an afflicted subject and is not limited to complete prevention of an affliction.

The invention also provides a method of treating or preventing a disease or disorder where a modulator of Kv3 is required, for example those diseases and disorders mentioned hereinabove, which comprises administering to a subject in need thereof an effective amount of a compound of formula (I) or a pharmaceutically acceptable salt and/or solvate thereof.

The invention also provides a compound of formula (I), or a pharmaceutically acceptable salt and/or solvate thereof, for use in the treatment or prophylaxis of a disease or disorder where a modulator of Kv3 is required, for example those diseases and disorders mentioned hereinabove.

The invention also provides the use of a compound of formula (I), or a pharmaceutically acceptable salt and/or solvate thereof, in the manufacture of a medicament for the treatment or prophylaxis of a disease or disorder where a modulator of Kv3 is required, for example those diseases and disorders mentioned hereinabove.

The invention also provides a method of treating depression and mood disorders, schizophrenia, substance abuse disorders, sleep disorders or epilepsy, for example for those indications mentioned hereinabove, which comprises administering to a subject in need thereof an effective amount of a Kv3 modulator or a pharmaceutically acceptable salt and/or solvate thereof.

For use in therapy the compounds of the invention are usually administered as a pharmaceutical composition. The invention also provides a pharmaceutical composition comprising a compound of formula (I), or a pharmaceutically acceptable salt and/or solvate thereof, and a pharmaceutically acceptable carrier.

The compounds of formula (I) or their pharmaceutically acceptable salts and/or solvates thereof may be administered by any convenient method, e.g. by oral, parenteral, buccal, sublingual, nasal, rectal or transdermal administration, and the pharmaceutical compositions adapted accordingly. Other possible routes of administration include intratympanic and intracochlear.

The compounds of formula (I) or their pharmaceutically acceptable salts and/or solvates thereof which are active when given orally can be formulated as liquids or solids, e.g. as syrups, suspensions, emulsions, tablets, capsules or lozenges.

A liquid formulation will generally consist of a suspension or solution of the active ingredient in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluorochlorohydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment the composition is in unit dose form such as a tablet, capsule or ampoule.

The composition may contain from 0.1% to 100% by weight, for example from 10 to 60% by weight, of the active material, depending on the method of administration. The composition may contain from 0% to 99% by weight, for example 40% to 90% by weight, of the carrier, depending on the method of administration. The composition may contain from 0.05 mg to 1000 mg, for example from 1.0 mg to 500 mg, of the active material, depending on the method of administration. The composition may contain from 50 mg to 1000 mg, for example from 100 mg to 400 mg of the carrier, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 500 mg, and such unit doses may be administered more than once a day, for example two or three a day. Such therapy may extend for a number of weeks or months.

The invention provides, in a further aspect, a combination comprising a compound of formula (I) or a pharmaceutically acceptable salt, solvate and/or derivative thereof together with a further therapeutic agent or agents.

The invention provides a compound of formula (I), for use in combination with a further therapeutic agent or agents.

When the compounds are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations. The individual components of combinations may also be administered separately, through the same or different routes.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

The present invention also provides Kv3 modulators, or their pharmaceutically acceptable salts and/or solvates thereof, for use in the treatment or prophylaxis of depression and mood disorders, hearing disorders, schizophrenia, substance abuse disorders, sleep disorders or epilepsy.

In particular Kv3 modulators or their pharmaceutically acceptable salts and/or solvates may be particularly useful in the treatment or prophylaxis of depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90), Seasonal affective disorder.

The invention also provides a method of treating depression and mood disorders, hearing disorders, schizophrenia, substance abuse disorders, sleep disorders or epilepsy, including for example those disorders mentioned hereinabove, which comprises administering to a subject in need thereof an effective amount of Kv3 modulator or a pharmaceutically acceptable salt and/or solvate thereof.

The invention also provides a Kv3 modulator, or a pharmaceutically acceptable salt and/or solvate thereof, for use in the treatment or prophylaxis of depression and mood disorders, hearing disorders, schizophrenia, substance abuse disorders, sleep disorders or epilepsy, including for example those disorders mentioned hereinabove.

The invention also provides the use of a Kv3 modulator, or a pharmaceutically acceptable salt and/or solvate thereof, in the manufacture of a medicament for the treatment or prophylaxis of depression and mood disorders, hearing disorders, schizophrenia, substance abuse disorders, sleep disorders or epilepsy, including for example those disorders mentioned hereinabove.

For use in therapy the Kv3 modulators are usually administered as a pharmaceutical composition for example a composition comprising a Kv3 modulator or a pharmaceutically acceptable salt and/or solvate thereof, and a pharmaceutically acceptable carrier. Examples of such compositions, and methods of administration thereof, which compositions comprise a compound of formula (I) or a pharmaceutically acceptable salt thereof, are described hereinabove. Such compositions and methods of administration may also be used for other Kv3 modulators or pharmaceutically acceptable salts and/or solvates thereof, in the treatment of depression and mood disorders, hearing disorders, schizophrenia, substance abuse disorders, sleep disorders or epilepsy, including for example those disorders mentioned hereinabove.

Furthermore, the invention relates to a method for manufacturing compounds of formula (I), to novel intermediates of use in the manufacture of compounds of formula (I) and to the manufacture of such intermediates.

Particular intermediates of interest include:

3,3-dimethyl-1H-isobenzofuran-5-ol;

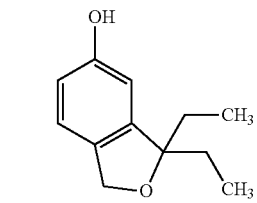

3,3-diethyl-1,3-dihydro-2-benzofuran-5-ol;

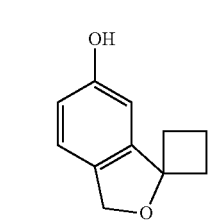 [SMILES: Oc1ccc2c(c1)C1(CCC1)OC2]

3H-spiro[2-benzofuran-1,1'-cyclobutan]-6-ol;

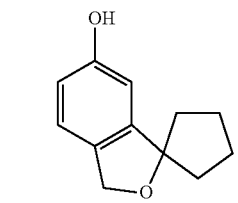 [SMILES: Oc1ccc2c(c1)C1(CCCC1)OC2]

3H-spiro[2-benzofuran-1,1'-cyclopentan]-6-ol;

3-(trifluoromethyl)-1,3-dihydroisobenzofuran-5-ol (enantiomer 1 and enantiomer 2);

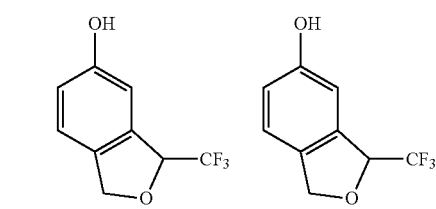 [SMILES: Oc1ccc2c(c1)C(C(F)(F)F)OC2 ; Oc1ccc2c(c1)C(C(F)(F)F)OC2]

3-tert-butyl-1,3-dihydro-2-benzofuran-5-ol (enantiomer 1 and enantiomer 2);

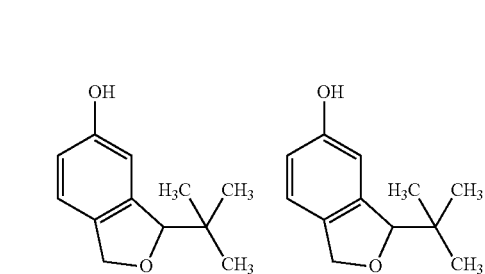

3-methyl-3-(trifluoromethyl)-1,3-dihydro-2-benzofuran-5-ol (enantiomer 1 and enantiomer 2);

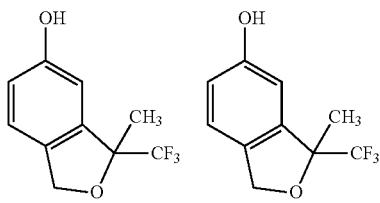

3-ethyl-1,3-dihydro-2-benzofuran-5-ol (enantiomer 1 and enantiomer 2);

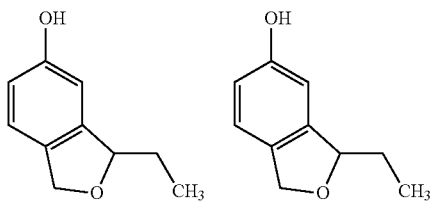

3-cyclopropyl-1,3-dihydro-2-benzofuran-5-ol (enantiomer 1 and enantiomer 2);

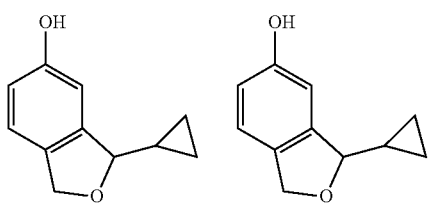

4,4-dimethyl-3,4-dihydro-1H-isochromen-6-ol;

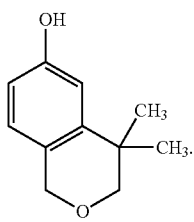

Especially of interest are the anilines:

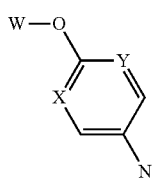

wherein:
W is the group:

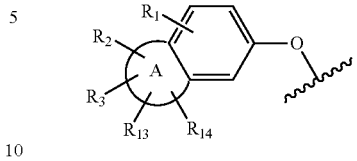

A, X, Y, $R_1$, $R_2$, $R_3$, $R_{13}$ and $R_{14}$ are as defined previously for compounds of formula (I) and the specifically mentioned embodiments of such groups as described above should be taken to apply equally to anilines.

EXPERIMENTAL

The invention is illustrated by the compounds described below. The following examples describe the laboratory synthesis of specific compounds of the invention and are not meant to limit the scope of the invention in any way with respect to compounds or processes. It is understood that, although specific reagents, solvents, temperatures and time periods are used, there are many possible equivalent alternatives that can be used to produce similar results. This invention is meant to include such equivalents.

Analytical Equipment

Starting materials, reagents and solvents were obtained from commercial suppliers and used without further purification unless otherwise stated. Unless otherwise stated, all compounds with chiral centres are racemic. Where reactions are described as having been carried out in a similar manner to earlier, more completely described reactions, the general reaction conditions used were essentially the same. Work up conditions used were of the types standard in the art, but may have been adapted from one reaction to another. The starting material may not necessarily have been prepared from the batch referred to. Compounds synthesised may have various purities ranging from for example 85% to 98%. Calculations of number of moles and yield are in some cases adjusted for this.

Proton Magnetic Resonance (indicated by "$^1$H-NMR") spectra) or Carbon Nuclear Magnetic Resonance (indicated by "$^{13}$C-NMR") were recorded either on Varian instruments at 200, 300, 400, 500 or 600 MHz, or on Bruker instruments at 400 MHz. Chemical shifts are reported in ppm (δ) using the residual solvent line as internal standard. Splitting patterns are designed as s (singlet), br.s (broad singlet), d (doublet), t (triplet), q (quartet), dd (doublet of doublets), dt (doublet of triplets) and m (multiplet). The NMR spectra were recorded at temperatures ranging from 25 to 60° C.

HPLC-Mass spectra (HPLC-MS) were taken on an Agilent 1100 Series LC/MSD Mass Spectrometer coupled with HPLC instrument Agilent 1100 Series, operating in positive electrospray ionization mode and in acidic gradient conditions.

Quality Control (8 Minutes Method):

LC/MS-ES+ under acidic conditions was performed on a Phenomenex Luna C18 column (3 μm 2×50 mm). Mobile phase: A: (H2O+0.05% TFA by vol.)/B: (CH$_3$CN+0.05% TFA by vol). Gradient: t=0 min 0% (B). From 0 to 95% (B) in 8 min. 95% (B) for 0.5 min. From 95 to 100% (B) in 0.5 min. 100% (B) for 0.5 min. From 100% to 0% (B) in 0.1 min. Stop time 11 min. Column T=40° C. Flow rate: 1.0 ml/min. Mass range ES+: (100-1000 amu, F=60). UV detection wavelengths: DAD 1A=220.8, DAD 1B=254.8. The use of this methodology is indicated by "LC/MS: QC_8_MIN" in the analytic characterization of the described compounds.

Quality Control (3 Minutes Method):

LC/MS-ES+ under acidic conditions was performed on a Zorbax SB C18 column (1.8 μm 3×50 mm). Mobile phase: A: ($H_2O$+0.05% TFA by vol.)/B: ($CH_3CN$+0.05% TFA by vol). Gradient: t=0 min 0% (B), from 0 to 95% (B) in 2.5 min, 95% (B) for 0.2 min, from 95 to 100% (B) in 0.2 min, 100% (B) for 0.4 min, from 100% to 0% (B) in 0.1 min. Stop time 4 min. Column T=60° C. Flow rate: 1.5 ml/min. Mass range ES+: (100-1000 amu, F=60). UV detection wavelengths: DAD 1A=220.8, DAD 1B=254.8. The use of this methodology is indicated by "LC/MS: QC_3_MIN" in the analytic characterization of the described compounds.

Ultra Performance Liquid Chromatography with an Acidic Gradient:

Total ion current (TIC) and DAD UV chromatographic traces together with MS and UV spectra associated with the peaks were taken on a UPLC/MS Acquity™ system equipped with 2996 PDA detector and coupled to a Waters Micromass ZQ™ mass spectrometer operating in positive or negative electrospray ionisation mode [LC/MS-ES (+ or −): analyses were performed using an Acquity™ UPLC BEH C18 column (50×2.1 mm, 1.7 μm particle size). General Method: Mobile phase: A: (water+0.1% $HCO_2H$)/B: ($CH_3CN$+0.06% $HCO_2H$). Gradient: t=0 min 3% (B), t=0.05 min 6% (B), t=0.57 min 70% (B), t=1.06 min 99% (B) lasting for 0.389 min, t=1.45 min 3% (B), stop time 1.5 min. Column T=40° C. Flow rate=1.0 mL/min. Mass range: ES (+): 100-1000 amu. ES (−): 100-800 amu. UV detection range: 210-350 nm. The use of this methodology is indicated by "UPLC_A" in the analytic characterization of the described compounds.

Ultra Performance Liquid Chromatography with a Basic Gradient:

Total ion current (TIC) and DAD UV chromatographic traces together with MS and UV spectra associated with the peaks were taken on a UPLC/MS Acquity™ system equipped with PDA detector and coupled to a Waters SQD mass spectrometer operating in positive and negative alternate electrospray ionisation mode [LC/MS-ES+/−: analyses were performed using an Acquity™ UPLC BEH C18 column (50×2.1 mm, 1.7 μm particle size). Mobile phase: A: (10 mM aqueous solution of $NH_4HCO_3$ (adjusted to pH 10 with ammonia))/B: $CH_3CN$. Gradient: t=0 min 3% (B), t=1.06 min 99% (B) lasting for 0.39 min, t=1.46 min 3% (B), stop time 1.5 min. Column T=40° C. Flow rate=1.0 mL/min. Mass range: ES (+): 100-1000 amu. ES (−): 100-1000 amu. UV detection range: 220-350 nm. The use of this methodology is indicated by "UPLC_B" in the analytic characterization of the described compounds.

In a number of preparations, purification was performed using manual flash chromatography, semi automatic flash chromatography (Biotage Flash Master Personal) or automatic flash chromatography (Biotage SP1 and SP4) apparatus.

Flash chromatographies on silica gel were carried out on pre-packed Biotage silica cartridges (e.g. Biotage SNAP cartridge KP-Sil). Reverse phase C18 flash chromatographies were carried out using VARIAN MEGA BE-C18 cartridges, or pre-packed Biotage C18 cartridges (e.g. Biotage SNAP cartridge KP-C18-HS).

SPE-SCX cartridges are ion exchange solid phase extraction columns supplied by Varian. The eluent used with SPE-SCX cartridges is DCM and MeOH or only MeOH followed by ammonia solution in MeOH. The collected fractions are those eluted with the ammonia solution in MeOH.

ABBREVIATIONS

AIBN azobisisobutyronitrile
Boc t-butyloxycarbonyl
BuLi butyllithium
$CDCl_3$ deutrated chloroform
CDI 1,1'-Carbonyldiimidazole
$(CH_2O)_n$ paraformaldehyde
cHex cyclohexane
CV column volume
DCM dichloromethane
DIPEA N,N-diisopropylethylamine
DMAP 4-dimethylaminopyridine
DMF N,N-dimethylformamide
DMSO dimethylsulfoxide
DMSO-$d_6$ deutrated dimethylsulfoxide
$Et_2O$ diethyl ether
EtOAc ethyl acetate
h hours
$H_2$ gaseous hydrogen
HATU (O-7-azabenzotriazol-1-yl)-N,N,N',N'-tetramethyluroniumhexafluoro phosphate)
$HCO_2H$ formic acid
HCl hydrogen chloride
$H_2SO_4$ sulfuric acid
$K_2CO_3$ potassium carbonate
KHDMS potassium hexamethyldisilazide
KOH potassium hydroxide
MeCN/$CH_3CN$ acetonitrile
MeOH methanol
MeOD deutrated methanol
MOM methoxymethyl
$N_2$ gaseous nitrogen
$NaHCO_3$ sodium hydrogencarbonate
$Na_2CO_3$ sodium carbonate
NaOH sodium hydroxide
NaOMe sodium methoxide
NMR Nuclear Magnetic Resonance
Pd/C palladium on charcoal
PE petroleum ether
r.t. room temperature
T3P propylphosphonic anhydride tBuOK potassium tert-butoxide
TBDMS (1,1-dimethylethyl)dimethylsilyl
TBTU o-Benzotriazol-1-yl-n,n,n',n'-tetramethyluronium tetrafluoroborate
TEA triethylamine
TFA trifluoroacetic acid
THF tetrahydrofuran TsOH*H₂O 4-methyl benzenesulfonic acid hydrate/p-toluenesulfonic acid hydrate Intermediate 1

3-(2-chloropyrimidin-5-yl)-5,5-dimethyl-imidazolidine-2,4-dione

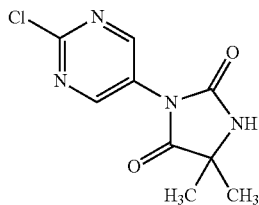 [SMILES: CC1(C)NC(=O)N(c2cnc(Cl)nc2)C1=O]

To a solution of triphosgene (1.38 g, 4.65 mmol) in ethyl acetate (20 ml) at 0° C. a solution of 2-chloro-5-aminopyrimidine (1 g, 7.75 mmol)/DIPEA (8 ml, 4.65 mmol) in ethyl acetate (40 ml) was slowly added (20 minutes) and the reaction mixture was stirred for 15 minutes at the same temperature. Maintaining the reaction mixture at 0° C., vacuum was applied (10 minutes) for removing the excess of phosgene. A solution of DMAP (0.945 g, 7.75 mmol) in ethyl acetate/dichloromethane 1:1 (8 ml) was added and the reaction mixture was stirred for 5 minutes at the same temperature. 2,2-Dimethylglycine methyl ester hydrochloride (2.37 g, 15.5 mmol) in ethyl acetate (30 ml) was slowly added (15 minutes) at 0° C. and the reaction mixture was stirred for 30 minutes at the same temperature. The reaction was quenched with aqueous buffer (pH3) while the pH was allowed to reach ~5-6 and two phases were separated. The organic layer was washed with aqueous buffer (pH3) (2×20 ml) and then brine (20 ml), dried (Na₂SO₄), filtered and evaporated affording the urea intermediate as orange foam.

The urea was dissolved in MeOH (20 ml), NaOMe (0.41 g, 7.75 mmol) was added and the reaction mixture was stirred for 15 minutes at r.t. The mixture was quenched with an aqueous saturated solution of ammonium chloride (25 ml) and diluted with ethyl acetate (50 ml). Two phases were separated and the organic layer was washed with brine (2×20 ml), dried (Na₂SO₄), filtered and evaporated. The residue was triturated with Et₂O (10 ml) and the solid collected affording the title compound (1.08 g) as an orange solid.

LC/MS: QC_3_MIN: Rt=1.062 min; m/z 241 [M+H]+.

The following compounds were prepared using the foregoing methodology, replacing 2-chloro-5-aminopyrimidine with the appropriate halo-aniline and 2,2-dimethylglycine methyl ester hydrochloride with the appropriate amino ester hydrochloride. Final products were purified by flash-chromatography (Silica cartridge; Cyclohexane/EtOAc or other appropriate solvent system) or triturated in an appropriate solvent or crystallised from an appropriate solvent.

| Int. | Structure | Name | Aniline | Amino ester hydrochloride | LCMS |
|---|---|---|---|---|---|
| 2 | 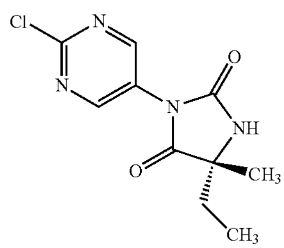 [SMILES: CC[C@@]1(C)NC(=O)N(c2cnc(Cl)nc2)C1=O] | (5R)-3-(2-chloropyrimidin-5-yl)-5-ethyl-5-methyl-imidazolidine-2,4-dione | 2-chloro-5-amino-pyrimidine | methyl (2R)-2-amino-2-methylbutanoate hydrochloride | LC/MS: QC_3_MIN: Rt = 1.341 min; m/z 255 [M + H]+. |
| 3 | 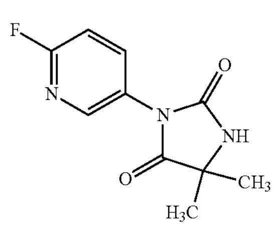 [SMILES: CC1(C)NC(=O)N(c2ccc(F)nc2)C1=O] | 3-(6-fluoropyridin-3-yl)-5,5-dimethyl-imidazolidine-2,4-dione | 2-fluoro-5-amino-pyridine | 2,2-Dimethylglycine methyl ester hydrochloride | LC/MS: QC_3_MIN: Rt = 1.704 min; m/z 224 [M + H]+. |
| 4 | 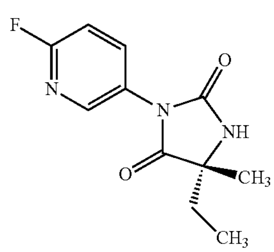 [SMILES: CC[C@@]1(C)NC(=O)N(c2ccc(F)nc2)C1=O] | (5R)-5-ethyl-3-(6-fluoropyridin-3-yl)-5-methyl-imidazolidine-2,4-dione | 2-fluoro-5-amino-pyridine | methyl (2R)-2-amino-2-methylbutanoate hydrochloride | LC/MS: QC_3_MIN: Rt = 1.105 min; m/z 238 [M + H]+. |

-continued

| Int. | Structure | Name | Aniline | Amino ester hydrochloride | LCMS |
|---|---|---|---|---|---|
| 5 | (structure) | (5R)-5-ethyl-3-(6-fluoro-5-methylpyridin-3-yl)-5-methyl-imidazolidine-2,4-dione | 6-fluoro-5-methyl-pyridin-3-amine | methyl (2R)-2-amino-2-methylbutanoate hydrochloride | LC/MS: QC_3_MIN: Rt = 1.370 min; m/z 252 [M + H]+. |
| 6 | (structure) | 3-(6-fluoro-5-methylpyridin-3-yl)-5,5-dimethyl-imidazolidine-2,4-dione | 6-fluoro-5-methyl-pyridin-3-amine | 2,2-Dimethylglycine methyl ester hydrochloride | LC/MS: QC_3_MIN: Rt = 1.057 min; m/z 238 [M + H]+. |

Intermediate 7

2-bromo-4-hydroxybenzonitrile

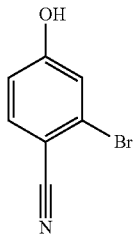

To a solution of 2-bromo-4-fluoro-benzonitrile (2000 mg, 9.9995 mmol) in DMF (20 mL), potassium trimethylsilanolate (2565.7 mg, 19.999 mmol) was added portionwise and the reaction mixture stirred at room temperature for 1 h. The mixture was diluted with ethyl acetate (100 ml), washed with an aqueous saturated solution of ammonium chloride (100 ml) and brine (3×100 ml), dried over sodium sulphate and concentrated under vacuum to give the title compound (2000 mg) which was used in the next step without purification.

LC/MS: QC_3_MIN: Rt=1.197 min; m/z 198-200 (Bromine pattern) [M+H]+.

Intermediate 8

2-bromo-4-hydroxybenzaldehyde

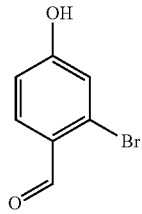

To a solution of 2-bromo-4-hydroxy-benzonitrile (Intermediate 7, 2000 mg, 10.1 mmol) in DCM (50 mL) and THF (10 mL), at 0° C., diisobutylaluminum hydride 1M in toluene (20.2 ml, 20.2 mmol) was slowly added (10 min) and the reaction mixture was stirred at the same temperature for 1 hour. Then 40 ml of HCl 2M were added and the reaction mixture was warmed at 40° C. for 30 minutes. After cooling ethyl acetate (100 ml) was added and two phases were separated. The organic layer was washed with brine (3×100 ml) dried over sodium sulphate and concentrated under vacuum to give the title compound (1950 mg) which was used in the next step without further purification.

LC/MS: QC_3_MIN: Rt=1.181 min; m/z 201-203 (Bromine pattern) [M+H]+.

Intermediate 9

[2-bromo-4-[tert-butyl(dimethyl)silyl]oxy-phenyl]methanol

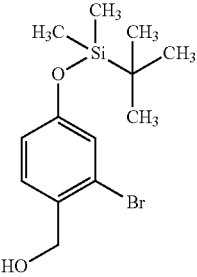

To a solution of 2-bromo-4-hydroxy-benzaldehyde (Intermediate 8, 1950 mg, 9.7005 mmol) in DCM (50 mL) at room temperature imidazole (1320.8 mg, 19.401 mmol) and tert-butyl-chloro-dimethyl-silane (1608.3 mg, 10.671 mmol) were added and the reaction mixture was stirred at the same temperature for 30 minutes. Then, 100 ml of ethyl acetate and 100 ml of ammonium chloride were added and the organic phase separated and washed with brine (3×100 ml), dried over sodium sulphate and concentrated under vacuum.

The residue was dissolved in THF (50 mL) and cooled to 0° C., lithium aluminium hydride 2M in THF (4.85 ml, 9.70 mmol) was slowly added and the reaction mixture was stirred at the same temperature for 30 minutes. Then, the reaction was quenched in a cooled saturated solution of ammonium chloride and extracted with ethyl acetate (100 ml). The organic layer was washed with brine, dried over sodium sulphate and concentrated under vacuum. The residue was purified by flash chromatography on silica gel (Biotage system) using a SNAP 100 g as column and cyclohexane/ethyl acetate from 100:0 to 80:20 in 10 column volumes to give the title compound (1400 mg).

LC/MS: QC_3_MIN: Rt=2.270 min; m/z 299-301 (Bromine pattern) [(M−H$_2$O)+H]+.

Intermediate 10

2-[5-[tert-butyl(dimethyl)silyl]oxy-2-(hydroxymethyl)phenyl]propan-2-ol

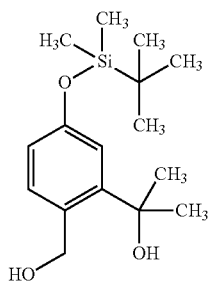 [SMILES: CC(C)(O)c1cc(O[Si](C)(C)C(C)(C)C)ccc1CO]

To a solution of [2-bromo-4-[tert-butyl(dimethyl)silyl]oxy-phenyl]methanol (Intermediate 9, 500 mg, 1.5758 mmol) in dry hexane (8 mL) and THF (2 mL) at −15° C. butyllithium 1.6M in hexane (2.17 ml, 3.467 mmol) was slowly added (10 min) and the reaction mixture was stirred at the same temperature for 2 hours. Then a solution of acetone (118.98 mg, 2.0486 mmol) in dry hexane (1 ml) was added at −15° C. and the reaction mixture stirred at the same temperature for additional 1 hour. The reaction was quenched with an aqueous saturated solution of ammonium chloride and extracted with ethyl acetate (100 ml). The organic layer was washed with brine, dried over sodium sulphate and concentrated under vacuum. The residue was purified by flash chromatography on silica gel (Biotage system) using a SNAP 50 g as column and cyclohexane/ethyl acetate from 100:0 to 60:40 as eluent in 12 column volumes, to give the title compound (240 mg) as a colourless oil.

LC/MS: QC_3_MIN: Rt=2.108 min; m/z 261 [(M−2H$_2$O)+H]+.

The following compounds were prepared using the foregoing methodology, replacing acetone with the appropriate carbonylic compound (aldehydes or ketones). Final products were purified by flash-chromatography (Silica cartridge; Cyclohexane/EtOAc or other appropriate solvent system).

| Int. | Structure | Name | Carbonylic compound | LCMS |
|---|---|---|---|---|
| 11 | 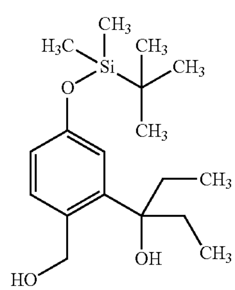 | 3-[5-[tert-butyl(dimethyl)silyl]oxy-2-(hydroxymethyl)phenyl]pentan-3-ol | 3-pentanone | LC/MS: QC_8_MIN: Rt = 6.428 min; m/z 289 [(M − 2H$_2$O) + H]+. |
| 12 | 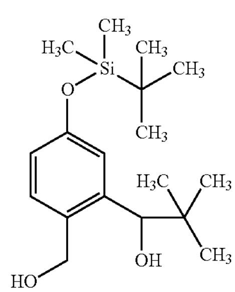 | 1-[5-[tert-butyl(dimethyl)silyl]oxy-2-(hydroxymethyl)phenyl]-2,2-dimethyl-propan-1-ol | 2,2-dimethyl propanal | LC/MS: QC_3_MIN: Rt = 2.174 min; m/z 289 [(M − 2H$_2$O) + H]+. |

-continued

| Int. | Structure | Name | Carbonylic compound | LCMS |
|---|---|---|---|---|
| 13 | 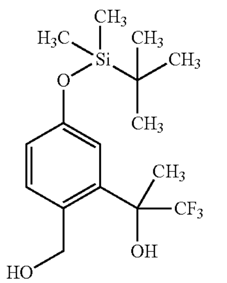 [SMILES: CC(O)(c1cc(O[Si](C)(C)C(C)(C)C)ccc1CO)C(F)(F)F] | 2-[5-[tert-butyl(dimethyl)silyl]oxy-2-(hydroxymethyl)phenyl]-1,1,1-trifluoro-propan-2-ol | 1,1,1-trifluoroacetone | LC/MS: QC_8_MIN: Rt = 6.310 min; m/z 333 [(M − H$_2$O) + H]+. |
| 14 | 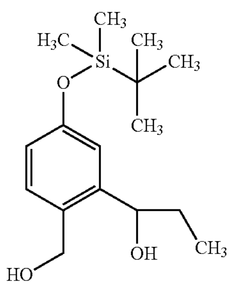 [SMILES: CCC(O)c1cc(O[Si](C)(C)C(C)(C)C)ccc1CO] | 1-[5-[tert-butyl(dimethyl)silyl]oxy-2-(hydroxymethyl)phenyl]propan-1-ol | propanal | LC/MS: QC_8_MIN: Rt = 5.860 min; m/z 279 [(M − H$_2$O) + H]+. |
| 15 | 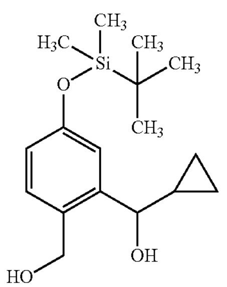 [SMILES: CC(C)(C)[Si](C)(C)Oc1ccc(CO)c(C(O)C2CC2)c1] | [5-[tert-butyl(dimethyl)silyl]oxy-2-(hydroxymethyl)phenyl]-cyclopropyl-methanol | cyclopropane-carbaldehyde | LC/MS: QC_8_MIN: Rt = 5.997 min; m/z 291 [(M − H$_2$O) + H]+. |
| 16 | 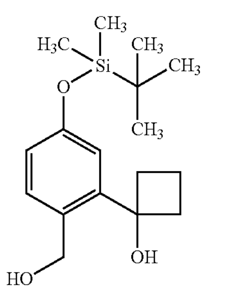 | 1-[5-[tert-butyl(dimethyl)silyl]oxy-2-(hydroxymethyl)phenyl]cyclo-butanol | cyclobutanone | LC/MS: QC_3_MIN: Rt = 2.215 min; m/z 273 [(M − 2H$_2$O) + H]+. |
| 17 | 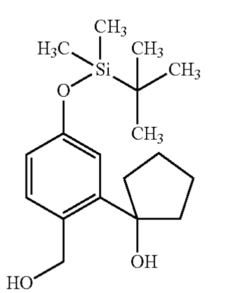 | 1-[5-[tert-butyl(dimethyl)silyl]oxy-2-(hydroxymethyl)phenyl]cyclo-pentanol | cyclopentanone | LC/MS: QC_3_MIN: Rt = 2.243 min; m/z 287 [(M − 2H$_2$O) + H]+. |

Intermediate 18

3,3-dimethyl-1H-isobenzofuran-5-ol

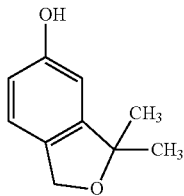

To a solution of 2-[5-[tert-butyl(dimethyl)silyl]oxy-2-(hydroxymethyl)phenyl]propan-2-ol (Intermediate 10, 1.344 g, 4.533 mmol) in THF (5 mL) at 0° C. butyllithium 1.6M in hexane (3.116 ml, 4.98 mmol) was added and the reaction mixture was stirred for 5 minutes at the same temperature. 4-methylbenzenesulfonyl chloride (1.04 g, 5.44 mmol) dissolved in 1 ml of THF was added followed by the addition of butyllithium 1.6M in hexane (3.116 ml, 4.98 mmol). After 10 minutes at the same temperature tetrabutylammonium fluoride (9.066 ml, 9.066 mmol) was added and the reaction mixture stirred for additional 10 min. Then, it was quenched with ammonium chloride (50 ml) and extracted with ethyl acetate (100 ml). The organic phase was washed with brine (2×100 ml), dried with Na2SO4 and concentrated under vacuum. The residue was purified by flash chromatography on silica gel (Biotage system) using a SNAP 50 g as column and cyclohexane/ethyl acetate from 100:0 to 70:30 to afford the title compound (500 mg) as white solid LC/MS: QC_3_MIN: Rt=1.772 min; m/z 147 [(M−H$_2$O)+H]+.

The following compounds were prepared using the foregoing methodology, replacing 2-[5-[tert-butyl(dimethyl)silyl]oxy-2-(hydroxymethyl)phenyl]propan-2-ol (Intermediate 10) with the appropriate dihydroxy compound. Final products were purified by flash-chromatography (Silica cartridge; Cyclohexane/EtOAc or other appropriate solvent system).

| Int. | Structure | Name | Dihydroxy compound | LCMS |
|---|---|---|---|---|
| 19 | (structure) | 3,3-diethyl-1,3-dihydro-2-benzofuran-5-ol | 3-[5-[tert-butyl(dimethyl)silyl]oxy-2-(hydroxymethyl)phenyl]pentan-3-ol (Intermediate 11) | LC/MS: QC_8_MIN: Rt = 4.338 min; m/z 175 [(M − H$_2$O) + H]+. |
| 20 | (structure) | 3-tert-butyl-1,3-dihydro-2-benzofuran-5-ol | 1-[5-[tert-butyl(dimethyl)silyl]oxy-2-(hydroxymethyl)phenyl]-2,2-dimethyl-propan-1-ol (Intermediate 12) | LC/MS: QC_3_MIN: Rt = 1.592 min; m/z 175 [(M − H$_2$O) + H]+. |
| 21 | (structure) | 3-methyl-3-(trifluoromethyl)-1,3-dihydro-2-benzofuran-5-ol | 2-[5-[tert-butyl(dimethyl)silyl]oxy-2-(hydroxymethyl)phenyl]-1,1,1-trifluoro-propan-2-ol (Intermediate 13) | LC/MS: QC_8_MIN: Rt = 4.462 min; m/z 219 [M + H]+. |
| 22 | (structure) | 3-ethyl-1,3-dihydro-2-benzofuran-5-ol | 1-[5-[tert-butyl(dimethyl)silyl]oxy-2-(hydroxymethyl)phenyl]propan-1-ol (Intermediate 14) | LC/MS: QC_8_MIN: Rt = 3.948 min; m/z 147 [(M − H$_2$O) + H]+. |
| 23 | (structure) | 3-cyclopropyl-1,3-dihydro-2-benzofuran-5-ol | [5-[tert-butyl(dimethyl)silyl]oxy-2-(hydroxymethyl)phenyl]-cyclopropyl-methanol (Intermediate 15) | LC/MS: QC_8_MIN: Rt = 4.097 min; m/z 177 [M + H]+. |

| Int. | Structure | Name | Dihydroxy compound | LCMS |
|---|---|---|---|---|
| 24 | ![structure] | 3H-spiro[2-benzofuran-1,1'-cyclobutan]-6-ol | 1-[5-[tert-butyl(dimethyl)silyl]oxy-2-(hydroxymethyl)phenyl]cyclobutanol (Intermediate 16) | LC/MS: QC_3_MIN: Rt = 1.826 min; m/z 159 [(M − H$_2$O) + H]+. |
| 25 | ![structure] | 3H-spiro[2-benzofuran-1,1'-cyclopentan]-6-ol | 1-[5-[tert-butyl(dimethyl)silyl]oxy-2-(hydroxymethyl)phenyl]cyclopentanol (Intermediate 17) | LC/MS: QC_3_MIN: Rt = 1.483 min; m/z 173 [(M − H$_2$O) + H]+. |

Intermediate 26

6-[tert-butyl(dimethyl)silyl]oxy-1-(trifluoromethyl)-3H-isobenzofuran-1-ol

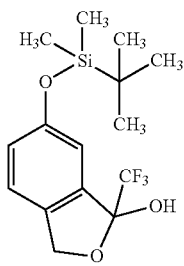

To a solution of [2-bromo-4-[tert-butyl(dimethyl)silyl]oxy-phenyl]methanol (Intermediate 9, 2.0 g, 6.3 mmol) in dry hexane (16 mL)/THF (4 mL) at −15° C. butyllithium 1.6M in Hexane (8.67 ml, 13.87 mmol) was slowly added (20 minutes) and the reaction mixture was stirred for 30 minutes at the same temperature. A solution of trifluoroacetic anhydride (1.98 g, 9.45 mmol) in dry hexane (4 ml) was added and the reaction mixture was stirred for 30 minutes at the same temperature. The reaction was quenched with an aqueous saturated solution of NH$_4$Cl (10 ml), diluted with water (20 ml) and extracted with ethyl acetate (2×50 ml). The organic layer was dried (Na$_2$SO$_4$), filtered and evaporated and the residue was purified by flash chromatography (Biotage system) on silica gel using a SNAP 50 g as column and cyclohexane/ethyl acetate from 100:0 to 70:30 as eluent affording the title compound (1.24 g) as white solid.

LC/MS: QC_3_MIN: Rt=2.818 min; m/z 317 [(M−H2O)+H]+.

Intermediate 27

3-(trifluoromethyl)-1,3-dihydroisobenzofuran-5-ol

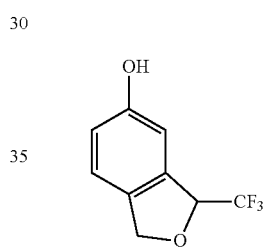

To a solution of 6-[tert-butyl(dimethyl)silyl]oxy-1-(trifluoromethyl)-3H-isobenzofuran-1-ol (Intermediate 26, 1.2 g, 3.59 mmol) in DCM (20 mL) 2,2,2-trifluoroacetic acid (5.5 ml, 71.77 mmol) and then triethylsilane (2.86 ml, 17.94 mmol) were added and the reaction mixture was stirred for 1 hour at room temperature. The reaction was diluted with DCM (50 ml) and water (30 ml) and two phases were separated. The organic layer was washed with brine (2×20 ml), dried (Na$_2$SO$_4$), filtered and evaporated. The residue was dissolved in THF (20 mL) and tetrabutylammonium fluoride 1M in THF (3.6 ml, 3.6 mmol) was added. The reaction mixture was stirred for 1 hour at room temperature. The reaction was diluted with an aqueous saturated solution of NH$_4$Cl (30 ml) and extracted with ethyl acetate (2×30 ml). The organic layer was dried (Na$_2$SO$_4$), filtered and evaporated and the residue was purified by flash chromatography (Biotage system) on silica gel using a SNAP 25 g as column and cyclohexane/ethyl acetate from 100:0 to 70:30 as eluent affording the title compound (550 mg) as colourless oil.

LC/MS: QC_3_MIN: Rt=1.988 min; m/z 205 [M+H]+.

Intermediate 28 (Enantiomer 1) and Intermediate 29 (Enantiomer 2)

3-(trifluoromethyl)-1,3-dihydroisobenzofuran-5-ol

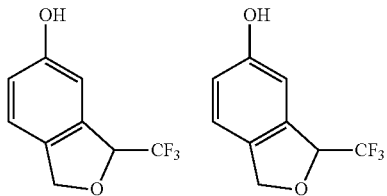 [SMILES: Oc1ccc2c(c1)C(C(F)(F)F)OC2 ; Oc1ccc2c(c1)C(C(F)(F)F)OC2]

Two enantiomers were obtained by chiral separation of racemic mixture (Intermediate 27, 550 mg):

Preparative Method:

| Column | Chiralcel OJ-H (25 × 3.0 cm), 5μ |
|---|---|
| Mobile phase | n-Hexane/2-Propanol 95/5% v/v |
| Flow rate (ml/min) | 40 ml/min |
| DAD detection | 220 nm |
| Loop | 1000 μL |
| Solubilisation | 300 mg in 10 ml EtOH/n-Hexane 3/2 = 30 mg/ml |
| Injection | 30 mg (each injection) |

Analytical Characterization:

| Column | Chiralcel OJ-H (25 × 0.46 cm), 5μ |
|---|---|
| Mobile phase | n-Hexane/2-Propanol 95/5% v/v |
| Flow rate (ml/min) | 1 ml/min |
| DAD detection | 220 nm |
| Loop | 5 μL |

Intermediate 28 (Enantiomer 1)

250 mg; Rt=19.7 minutes.

Intermediate 29 (Enantiomer 2)

248 mg; Rt=24.3 minutes.

Intermediate 30 (Enantiomer 1) and Intermediate 31 (Enantiomer 2)

3-tert-butyl-1,3-dihydro-2-benzofuran-5-ol

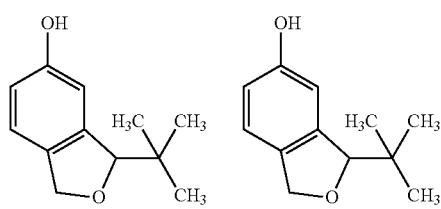

Two enantiomers were obtained by chiral separation of racemic mixture (Intermediate 20, 300 mg):

Preparative Method:

| Column | Chiralpak AD-H (25 × 2.0 cm), 5μ |
|---|---|
| Mobile phase | n-Hexane/2-Propanol 90/10% v/v |
| Flow rate (ml/min) | 17 ml/min |
| DAD detection | 220 nm |
| Loop | 1000 μL |
| Solubilisation | 300 mg in 20 ml EtOH/n-Hexane 3/1 = 15 mg/ml |
| Injection | 15 mg (each injection) |

Analytical Characterization:

| Column | Chiralpak AD-H (25 × 0.46 cm), 5μ |
|---|---|
| Mobile phase | n-Hexane/2-Propanol 90/10% v/v |
| Flow rate (ml/min) | 1 ml/min |
| DAD detection | 220 nm |
| Loop | 20 μL |

Intermediate 30 (Enantiomer 1)

130 mg; Rt=7.2 minutes.

Intermediate 31 (Enantiomer 2)

130 mg; Rt=9.3 minutes.

Intermediate 32 (Enantiomer 1) and Intermediate 33 (Enantiomer 2)

3-methyl-3-(trifluoromethyl)-1,3-dihydro-2-benzofuran-5-ol

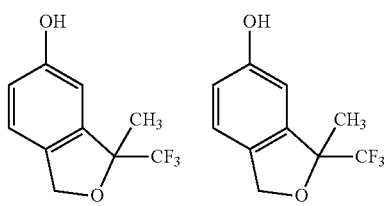

Two enantiomers were obtained by chiral separation of racemic mixture (Intermediate 21, 600 mg):

Preparative Method:

| Column | Chiralcel OJ-H (25 × 3.0 cm), 5μ |
|---|---|
| Mobile phase | n-Hexane/2-Propanol 88/12% v/v |
| Flow rate (ml/min) | 40 ml/min |
| DAD detection | 220 nm |
| Loop | 1000 μL |
| Solubilisation | 300 mg in 10 ml EtOH/n-Hexane 3/2 = 30 mg/ml |
| Injection | 30 mg (each injection) |

Analytical Characterization:

| Column | Chiralcel OJ-H (25 × 0.46 cm), 5μ |
|---|---|
| Mobile phase | n-Hexane/2-Propanol 88/12% v/v |
| Flow rate (ml/min) | 1 ml/min |
| DAD detection | 220 nm |
| Loop | 10 μL |

Intermediate 32 (Enantiomer 1)

280 mg; Rt=8.4 minutes.

Intermediate 33 (Enantiomer 2)

280 mg; Rt=11.6 minutes.

Intermediate 34 (Enantiomer 1) and Intermediate 35 (Enantiomer 2)

3-ethyl-1,3-dihydro-2-benzofuran-5-ol

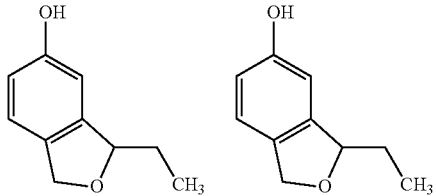

Two enantiomers were obtained by chiral separation of racemic mixture (Intermediate 22, 300 mg):
Preparative Method:

| Column | Chiralcel OJ-H (25 × 3.0 cm), 5µ |
|---|---|
| Mobile phase | n-Hexane/2-Propanol 90/10% v/v |
| Flow rate (ml/min) | 40 ml/min |
| DAD detection | 220 nm |
| Loop | 1000 µL |
| Solubilisation | 300 mg in 10 ml EtOH/n-Hexane 4/1 = 30 mg/ml |
| Injection | 30 mg (each injection) |

Analytical Characterization:

| Column | Chiralcel OJ-H (25 × 0.46 cm), 5µ |
|---|---|
| Mobile phase | n-Hexane/2-Propanol 90/10% v/v |
| Flow rate (ml/min) | 1 ml/min |
| DAD detection | 220 nm |
| Loop | 20 µL |

Intermediate 34 (Enantiomer 1)

130 mg; Rt=9.7 minutes.

Intermediate 35 (Enantiomer 2)

130 mg; Rt=12.4 minutes.

Intermediate 36 (Enantiomer 1) and Intermediate 37 (Enantiomer 2)

3-cyclopropyl-1,3-dihydro-2-benzofuran-5-ol

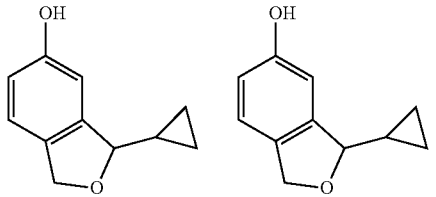

Two enantiomers were obtained by chiral separation of racemic mixture (Intermediate 23, 300 mg):
Preparative Method:

| Column | Chiralpak AD-H (25 × 3.0 cm), 5µ |
|---|---|
| Mobile phase | n-Hexane/2-Propanol 90/10% v/v |
| Flow rate (ml/min) | 40 ml/min |
| DAD detection | 220 nm |
| Loop | 1000 µL |
| Solubilisation | 300 mg in 10 ml EtOH/n-Hexane 4/1 = 30 mg/ml |
| Injection | 30 mg (each injection) |

Analytical Characterization:

| Column | Chiralpak AD-H (25 × 0.46 cm), 5µ |
|---|---|
| Mobile phase | n-Hexane/2-Propanol 90/10% v/v |
| Flow rate (ml/min) | 1 ml/min |
| DAD detection | 220 nm |
| Loop | 20 µL |

Intermediate 36 (Enantiomer 1)

130 mg; Rt=10.5 minutes.

Intermediate 37 (Enantiomer 2)

130 mg; Rt=13.5 minutes.

Intermediate 38 ethyl 2-(3-methoxyphenyl)-2-methyl-propanoate

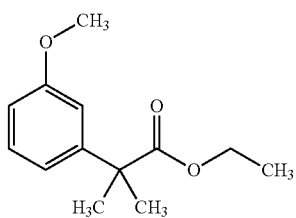 [SMILES: CCOC(=O)C(C)(C)c1cccc(OC)c1]

To a suspension in THF (30 ml) of sodium hydride 60% dispersion in mineral oil (2.41 g, 60.24 mmol) at 0° C. a solution of ethyl 2-(3-methoxyphenyl)acetate (5.32 g, 27.4 mmol) in THF (20 ml) was added dropwise over 15 minutes. The resulting mixture was stirred at 0° C. for 30 minutes. Iodomethane (8.55 g, 60.24 mmol) was added dropwise and the reaction mixture was stirred for 2 hours while the temperature was allowed to reach room temperature. The reaction was quenched with a slow addition of a 2N aqueous solution of HCl (20 ml) at 0° C. The resulting solution was extracted with EtOAc (40 ml) and the organics washed with an aqueous saturated solution of $NaHCO_3$ (30 ml) and $H_2O$ (30 ml). The organics were dried over $Na_2SO_4$ and concentrated in vacuo to afford the title compound (4.492 g) as a dark yellow oil that was used in the next step without further purification.

LC/MS: QC_3_MIN: Rt=1.972 min; m/z 223 [M+H]+.

Intermediate 39

2-(3-methoxyphenyl)-2-methyl-propan-1-ol

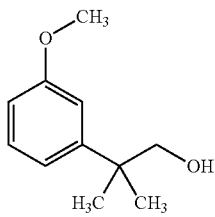

To a solution of ethyl 2-(3-methoxyphenyl)-2-methyl-propanoate (Intermediate 38, 2 g, 9.0 mmol) in THF (20 mL) at 0° C., lithium aluminium hydride 2M in THF (9.0 ml, 18.0 mmol) was added and the resulting mixture was stirred for 20 minutes at the same temperature. The reaction was quenched with water (10 ml) (slow dropwise addition), and extracted with EtOAc (15 ml). The organic layer was washed with an aqueous 1N solution of HCl (10 ml), dried over $Na_2SO_4$ and concentrated in vacuo to afford the title compound (1.439 g) that was used in the next step without further purification.

LC/MS: QC_3_MIN: Rt=1.553 min; m/z 181 [M+H]+.

Intermediate 40

1-methoxy-3-[2-(methoxymethoxy)-1,1-dimethyl-ethyl]benzene

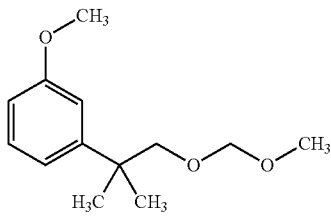 [SMILES: COCOCC(C)(C)c1cccc(OC)c1]

To a solution of 2-(3-methoxyphenyl)-2-methyl-propan-1-ol (Intermediate 39, 900 mg, 4.99 mmol) in THF (15 mL) sodium hydride 60% dispersion in mineral oil (300 mg, 7.49 mmol) was added and the reaction mixture was stirred for 15 minutes at room temperature. Chloro(methoxy)methane (603.02 mg, 7.49 mmol) was added and the reaction mixture was heated to 55° C. and stirred overnight. The reaction was cooled to 0° C. and quenched with water (10 mL) (added dropwise) and extracted with EtOAc (30 mL). Organics were dried over $Na_2SO_4$, filtered and evaporated in vacuo to afford the title compound (525 mg) that was used in the next step without further purification.

LC/MS: QC_3_MIN: Rt=1.913 min.

Intermediate 41

6-methoxy-4,4-dimethyl-3,4-dihydro-1H-isochromene

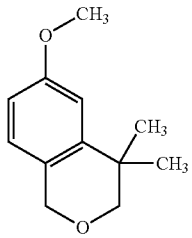

1-methoxy-3-[2-(methoxymethoxy)-1,1-dimethyl-ethyl]benzene (Intermediate 40, 300 mg, 1.3375 mmol) was dissolved in DCM (8 mL), the solution was cooled to −78° C. and titanium tetrachloride (37.928 mg, 0.2000 mmol) was added dropwise. The resulting mixture was stirred at room temperature for 2 hours. water (15 mL) was added and the mixture extracted with EtOAc (25 mL). Organics were dried over $Na_2SO_4$, filtered and evaporated to afford a crude that was purified by flash chromatography (Biotage system) on silica gel using a SNAP 25 g as column and cyclohexane/ethyl acetate from 100:0 to 90:10 as eluent affording the title compound (350 mg).

LC/MS: QC_3_MIN: Rt=1.784 min.

Intermediate 42

4,4-dimethyl-3,4-dihydro-1H-isochromen-6-ol

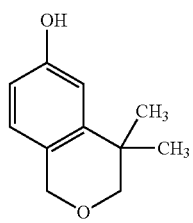

6-methoxy-4,4-dimethyl-3,4-dihydro-1H-isochromene (Intermediate 41, 350 mg, 1.8205 mmol) was dissolved in DCM (10 mL) and the solution was cooled to 0° C. Tribromoborane (228.04 mg, 0.9102 mmol) was added and the resulting mixture was stirred at 0° C. for 2 hours. Water (10 mL) was added and the two phases were separated. Organics were dried over $Na_2SO_4$, filtered and dried in vacuo. The crude was purified by flash chromatography (Biotage system) on silica gel using a SNAP 25 g as column and cyclohexane/ethyl acetate from 100:0 to 70:30 as eluent affording the title compound (42 mg).

LC/MS: QC_3_MIN: Rt=1.291 min; m/z 179 [M+H]+.

Intermediate 43

[3-bromo-4-(2-methylallyloxy)phenyl]acetate

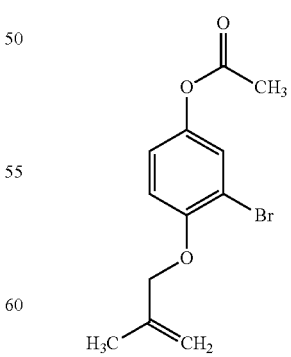

To a solution of 2-bromobenzene-1,4-diol (500 mg, 2.65 mmol) and N,N-diethylethanamine (0.55 ml, 3.97 mmol) in DCM (30 mL) acetic anhydride (0.27 g, 2.65 mmol) was slowly added and the reaction mixture was stirred for 8 hours at room temperature. The reaction was quenched with water (10 ml) diluted with an aqueous 2N solution of HCl (20 ml) and two phases were separated. The organic layer was washed with an aqueous 2N solution of HCl (2×10 ml), dried (Na2SO4), filtered and evaporated. The residue was dissolved in acetonitrile (15 mL), dipotassium carbonate (549 mg, 3.97 mmol) and then 3-bromo-2-methyl-prop-1-ene (428 mg, 3.17 mmol) were added and the reaction mixture was stirred for 5 hours at 50° C. After cooling the mixture was diluted with water (30 ml) and extracted with ethyl acetate (2×30 ml). The organic layer was dried (Na2SO4), filtered and evaporated and The residue was purified by flash chromatography (Biotage system) on silica gel using a SNAP 25 g as column and cyclohexane/ethyl acetate from 100:0 to 70:30 as eluent affording the title compound (190 mg) as colorless oil.

LC/MS: QC_3_MIN: Rt=2.586 min; m/z 285-287 (Bromine pattern) [M+H]+.

Intermediate 44

3,3-dimethyl-2H-benzofuran-5-ol

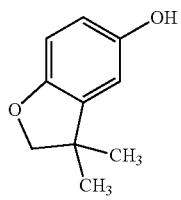

To a solution of [3-bromo-4-(2-methylallyloxy)phenyl]acetate (Intermediate 43, 190 mg, 0.67 mmol) in toluene (5 mL) azobisisobutyronitrile (0.13 g, 0.80 mmol) and tributylstannane (0.39 g, 1.33 mmol) were added and the reaction mixture was stirred for 2 hours at 90° C. Methanol (5 mL), water (3 mL) and sodium hydroxide 2M solution in water (0.67 ml, 1.33 mmol) were added and the reaction mixture was stirred for 1 hour at room temperature. A 2N aqueous solution of HCl was added while the pH was allowed to reach ~3-4 and ethyl acetate (30 ml) was added. Two phases were separated and a 10% w/w solution of KF was added to the organic phase and the mixture was stirred for 1 hour at room temperature. The solid was filtered off and the solution was dried (Na2SO4), and evaporated. The residue was purified by flash chromatography (Biotage system) on silica gel using a SNAP 25 g as column and cyclohexane/ethyl acetate from 100:0 to 70:30 as eluent affording the title compound (95 mg) as white solid.

LC/MS: QC_3_MIN: Rt=1.978 min; m/z 165 [M+H]+.

Intermediate 45

6-[(3,3-dimethyl-1,3-dihydro-2-benzofuran-5-yl)oxy]pyridin-3-amine

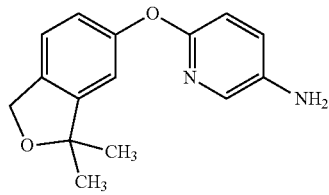

To a solution of 3,3-dimethyl-1H-isobenzofuran-5-ol (Intermediate 18, 30 mg, 0.18 mmol) and 2-chloro-5-nitro-pyridine (27.5 mg, 0.1736 mmol) in DMF (1 mL) dipotassium carbonate (37.8 mg, 0.2741 mmol) was added and the reaction mixture was stirred for 1.5 hours at 80° C. After cooling the reaction was quenched with water (1 ml), diluted with brine (5 ml) and extracted with ethyl acetate (2×10 ml). The organic layer was dried (Na$_2$SO$_4$), filtered and evaporated and the residue was dissolved in ethanol (3 mL)/water (1 mL). Iron (61.2 mg, 1.1 mmol) and an aqueous 6M solution of hydrogen chloride (0.03 ml, 0.18 mmol) were added and the reaction mixture was stirred for 4 hours at 50° C. The catalyst was filtered off and the resulting solution was diluted with a saturated solution of NaHCO$_3$ (15 ml) and extracted with ethyl acetate (2×20 ml). The organic layer was dried (Na$_2$SO$_4$), filtered and evaporated and the residue was purified by flash chromatography (Biotage system) on silica gel using a SNAP 10 g as column and cyclohexane/ethyl acetate from 80:20 to 30:70 as eluent affording the title compound (20 mg) as colourless oil.

LC/MS: QC_3_MIN: Rt=1.754 min; m/z 257 [M+H]+.

The following compounds were prepared using the foregoing methodology, replacing 3,3-dimethyl-1H-isobenzofuran-5-ol (Intermediate 18) with the appropriate phenol. Final products were purified by flash-chromatography (Silica cartridge; Cyclohexane/EtOAc or other appropriate solvent system).

| Int. | Structure | Name | Phenol | LCMS |
|---|---|---|---|---|
| 46 | 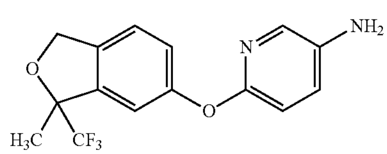 | 6-{[3-methyl-3-(trifluoromethyl)-1,3-dihydro-2-benzofuran-5-yl]oxy}pyridin-3-amine (enantiomer 1) | 3-methyl-3-(trifluoromethyl)-1,3-dihydro-2-benzofuarn-5-ol (Intermediate 32 enantiomer 1) | LC/MS: QC_3_MIN: Rt = 2.123 min; m/z 311 [M + H]+. |
| 47 | 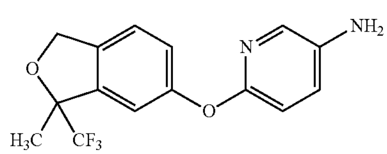 [SMILES: CC1(C(F)(F)F)OCc2ccc(Oc3ccc(N)cn3)cc21] | 6-{[3-methyl-3-(trifluoromethyl)-1,3-dihydro-2-benzofuran-5-yl]oxy}pyridin-3-amine (enantiomer 2) | 3-methyl-3-(trifluoromethyl)-1,3-dihydro-2-benzofuarn-5-ol (Intermediate 33 enantiomer 2) | LC/MS: QC_3_MIN: Rt = 1.989 min; m/z 311 [M + H]+. |

| Int. | Structure | Name | Phenol | LCMS |
|---|---|---|---|---|
| 48 | 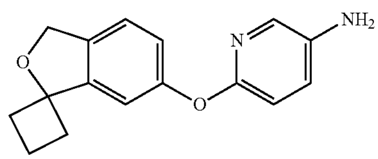 [SMILES: Nc1ccc(Oc2ccc3c(c2)C2(CCC2)OC3)nc1] | 6-(3H-spiro[2-benzofuran-1,1'-cyclobutan]-6-yloxy)pyridin-3-amine | 3H-spiro[2-benzofuran-1,1'-cyclobutan]-6-ol (Intermediate 24) | LC/MS: QC_3_MIN: Rt = 1.888 min; m/z 269 [M + H]+. |
| 49 | 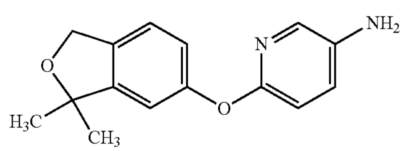 [SMILES: CC1(C)OCc2ccc(Oc3ccc(N)cn3)cc21] | 6-[(3,3-dimethyl-2,3-dihydro-1-benzofuran-5-yl)oxy]pyridin-3-amine | 3,3-dimethyl-2H-benzofuran-5-ol (Intermediate 44) | LC/MS: QC_3_MIN: Rt = 1.944 min; m/z 257 [M + H]+. |

Intermediate 50

2-(3H-spiro[2-benzofuran-1,1'-cyclobutan]-6-yloxy)pyrimidin-5-amine

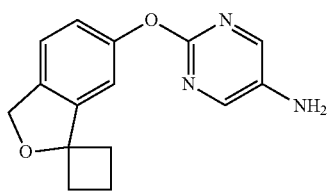 [SMILES: Nc1cnc(Oc2ccc3c(c2)C2(CCC2)OC3)nc1]

To a solution of spiro[1H-isobenzofuran-3,1'-cyclobutane]-5-ol (Intermediate 24, 50 mg, 0.28 mmol) in dry acetonitrile (4 mL) dipotassium carbonate (58.8 mg, 0.43 mmol) and then 2-chloro-5-nitro-pyrimidine (43.0 mg, 0.27 mmol) were added and the reaction mixture was stirred for 4 hours at room temperature. The reaction was diluted with ethyl acetate (20 ml) and washed with an aqueous saturated solution of ammonium chloride (2×10 ml). The organic layer was dried (Na$_2$SO$_4$), filtered and evaporated. The residue was dissolved in ethanol (5 mL)/water (1 mL). Iron (95.0 mg, 1.7 mmol) and an aqueous 6M solution of hydrogen chloride (0.05 ml, 0.3 mmol) were added and the reaction mixture was stirred at 50° C. for 3 hours. The catalyst was filtered off and the solution was diluted with an aqueous saturated solution of NaHCO$_3$ (10 ml) and extracted with ethyl acetate (2×15 ml). The organic layer was dried (Na$_2$SO$_4$), filtered and evaporated and the residue was purified by flash chromatography (Biotage system) on silica gel using a SNAP 10 g as column and cyclohexane/ethyl acetate from 60:40 to 0:100 as eluent affording the title compound (24 mg) as a light yellow solid. LC/MS: QC_3_MIN: Rt=1.875 min; m/z 270 [M+H]+.

The following compounds were prepared using the foregoing methodology, replacing 3H-spiro[2-benzofuran-1,1'-cyclobutan]-6-ol (Intermediate 24) with the appropriate phenol. Final products were purified by flash-chromatography (Silica cartridge; Cyclohexane/EtOAc or other appropriate solvent system).

| Int. | Structure | Name | Phenol | LCMS |
|---|---|---|---|---|
| 51 | 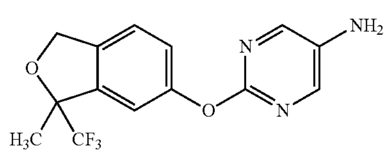 [SMILES: CC1(C(F)(F)F)OCc2ccc(Oc3ncc(N)cn3)cc21] | 2-{[3-methyl-3-(trifluoromethyl)-1,3-dihydro-2-benzofuran-5-yl]oxy}pyrimidin-5-amine (enantiomer 1) | 3-methyl-3-(trifluoromethyl)-1,3-dihydro-2-benzofuran-5-ol (Intermediate 32 enantiomer 1) | LC/MS: QC_3_MIN: Rt = 2.045 min; m/z 312 [M + H]+. |
| 52 | 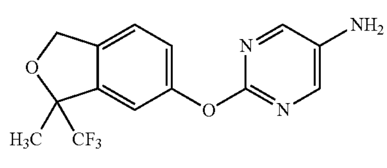 | 2-{[3-methyl-3-(trifluoromethyl)-1,3-dihydro-2-benzofuran-5-yl]oxy}pyrimidin-5-amine (enantiomer 2) | 3-methyl-3-(trifluoromethyl)-1,3-dihydro-2-benzofuran-5-ol (Intermediate 33 enantiomer 2) | LC/MS: QC_3_MIN: Rt = 2.002 min; m/z 312 [M + H]+. |

Intermediate 53 tert-butyl N-[(1R)-1-[[6-[(3,3-dimethyl-1H-isobenzofuran-5-yl)oxy]-3-pyridyl]carbamoyl]propyl]carbamate

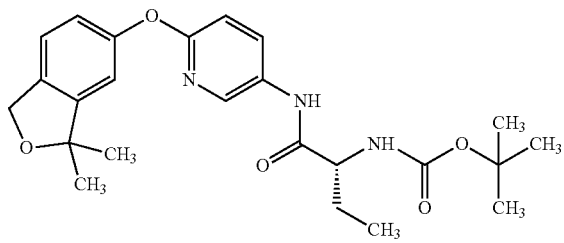 [SMILES: CC[C@@H](NC(=O)OC(C)(C)C)C(=O)Nc1ccc(Oc2ccc3c(c2)C(C)(C)OC3)nc1]

To a solution of (2R)-2-(tert-butoxycarbonylamino)butanoic acid (19.8 mg, 0.097 mmol) in dry DMF (1 mL) N-ethyl-N-isopropyl-propan-2-amine (0.27 ml, 0.16 mmol) and then [dimethylamino(triazolo[4,5-b]pyridin-3-yloxy)methylene]-dimethyl-ammonium hexafluorophosphate (35.60 mg, 0.094 mmol) were added and the reaction mixture was stirred for 15 minutes at room temperature. A solution of 6-[(3,3-dimethyl-1H-isobenzofuran-5-yl)oxy]pyridin-3-amine (Intermediate 45, 20 mg, 0.0780 mmol) in DMF (0.5000 mL) was added and the reaction mixture was stirred overnight at the same temperature. The reaction was quenched with brine (5 ml) and extracted with ethyl acetate (2×10 ml). The organic layer was dried (Na$_2$SO$_4$), filtered and evaporated and the residue was purified by flash chromatography (Biotage system) on silica gel using a SNAP 10 g as column and cyclohexane/ethyl acetate from 100:0 to 50:50 as eluent affording the title compound (25 mg) as white solid.

LC/MS: QC_3_MIN: Rt=2.439 min; m/z 442 [M+H]+.

The following compounds were prepared using the foregoing methodology, replacing 6-[(3,3-dimethyl-1H-isobenzofuran-5-yl)oxy]pyridin-3-amine (Intermediate 45) with the appropriate aniline. Final products were purified by flash-chromatography (Silica cartridge; Cyclohexane/EtOAc or other appropriate solvent system).

| Int. | Structure | Name | Aniline | LCMS |
|---|---|---|---|---|
| 54 | 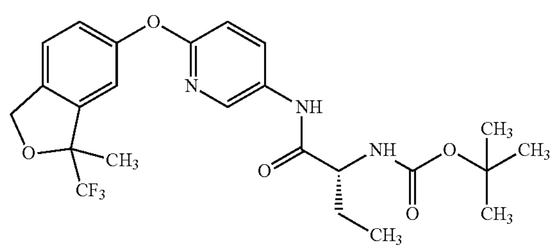 | tert-butyl N-[(1R)-1-[[6-[[3-methyl-3-(trifluoromethyl)-1H-isobenzofuran-5-yl]oxy]-3-pyridyl]carbamoyl]propyl]carbamate (diastereoisomer 1) | 6-{[3-methyl-3-(trifluoromethyl)-1,3-dihydro-2-benzofuran-5-yl]oxy}pyridin-3-amine (Intermediate 46, enantiomer 1) | LC/MS: QC_3_MIN: Rt = 2.520 min; m/z 496 [M + H]+. |
| 55 | 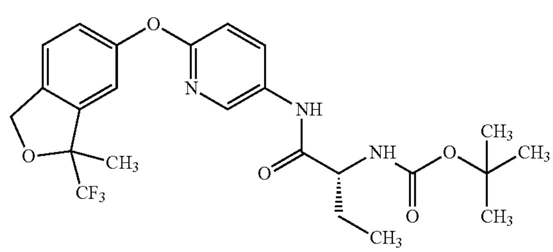 | tert-butyl N-[(1R)-1-[[6-[[3-methyl-3-(trifluoromethyl)-1H-isobenzofuran-5-yl]oxy]-3-pyridyl]carbamoyl]propyl]carbamate (diastereoisomer 2) | 6-{[3-methyl-3-(trifluoromethyl)-1,3-dihydro-2-benzofuran-5-yl]oxy}pyridin-3-amine (Intermediate 47, enantiomer 2) | LC/MS: QC_3_MIN: Rt = 2.520 min; m/z 496 [M + H]+. |
| 56 | 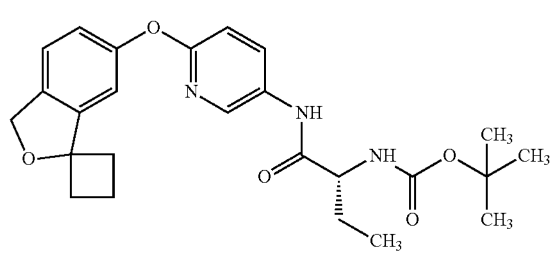 [SMILES: CC[C@@H](NC(=O)OC(C)(C)C)C(=O)Nc1ccc(Oc2ccc3c(c2)C2(CCC2)OC3)nc1] | tert-butyl N-[(1R)-1-[(6-spiro[1H-isobenzofuran-3,1'-cyclobutane]-5-yloxy-3-pyridyl)carbamoyl]propyl]carbamate | 6-(3H-spiro[2-benzofuran-1,1'-cyclobutan]-6-yloxy)pyridin-3-amine (Intermediate 48) | LC/MS: QC_3_MIN: Rt = 2.478 min; m/z 454 [M + H]+. |
| 57 | 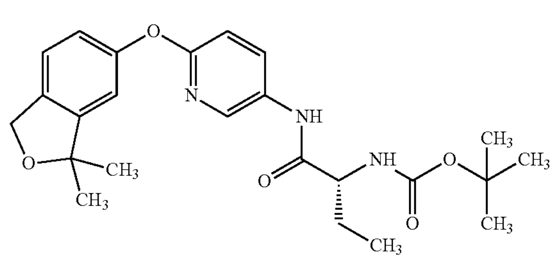 | tert-butyl N-[(1R)-1-[[6-[(3,3-dimethyl-1H-isobenzofuran-5-yl)oxy]-3-pyrimidin-5-yl]carbamoyl]propyl]carbamate | 6-[(3,3-dimethyl-2,3-dihydro-1-benzofuran-5-yl)oxy]pyridin-3-amine (Intermediate 49) | LC/MS: QC_3_MIN: Rt = 2.459 min; m/z 442 [M + H]+. |

| Int. | Structure | Name | Aniline | LCMS |
|---|---|---|---|---|
| 58 | 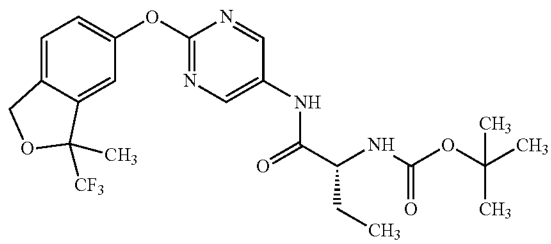 | tert-butyl N-[(1R)-1-[[2-[[3-methyl-3-(trifluoromethyl)-1H-isobenzofuran-5-yl]oxy]pyrimidin-5-yl]carbamoyl]propyl]carbamate (diastereoisomer 1) | 2-{[3-methyl-3-(trifluoromethyl)-1,3-dihydro-2-benzofuran-5-yl]oxy}pyrimidin-5-amine (Intermediate 51, enantiomer 1) | LC/MS: QC_3_MIN: Rt = 2.423 min; m/z 497 [M + H]+. |
| 59 | 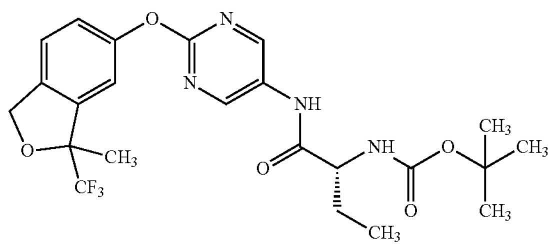 [SMILES: CC[C@@H](NC(=O)OC(C)(C)C)C(=O)Nc1cnc(Oc2ccc3c(c2)C(C)(C(F)(F)F)OC3)nc1] | tert-butyl N-[(1R)-1-[[2-[[3-methyl-3-(trifluoromethyl)-1H-isobenzofuran-5-yl]oxy]pyrimidin-5-yl]carbamoyl]propyl]carbamate (diastereoisomer 2) | 2-{[3-methyl-3-(trifluoromethyl)-1,3-dihydro-2-benzofuran-5-yl]oxy}pyrimidin-5-amine (Intermediate 52, enantiomer 2) | LC/MS: QC_3_MIN: Rt = 2.414 min; m/z 497 [M + H]+. |
| 60 | 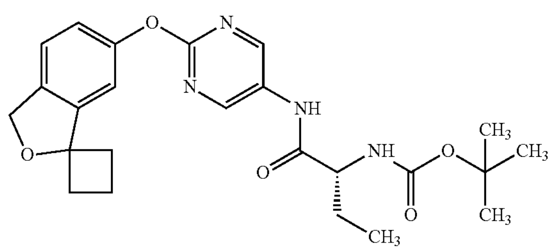 [SMILES: CC[C@@H](NC(=O)OC(C)(C)C)C(=O)Nc1cnc(Oc2ccc3c(c2)C2(CCC2)OC3)nc1] | tert-butyl N-[(1R)-1-[(2-spiro[1H-isobenzofuran-3,1'-cyclobutane]-5-yloxypyrimidin-5-yl)carbamoyl]propyl]carbamate | 2-(3H-spiro[2-benzofuran-1,1'-cyclobutan]-6-yloxy)pyrimidin-5-amine (Intermediate 50 | LC/MS: QC_3_MIN: Rt = 2.373 min; m/z 455 [M + H]+. |

Intermediate 61

(2R)-2-amino-N-[6-[(3,3-dimethyl-1H-isobenzofuran-5-yl)oxy]-3-pyridyl]butanamide

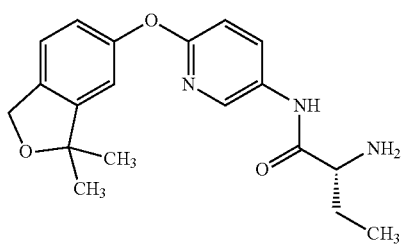 [SMILES: CC[C@@H](N)C(=O)Nc1ccc(Oc2ccc3c(c2)C(C)(C(F)(F)F)OC3)nc1]

To a solution of tert-butyl N-[(1R)-1-[[6-[(3,3-dimethyl-1H-isobenzofuran-5-yl)oxy]-3-pyridyl]carbamoyl]propyl]carbamate (Intermediate 53, 25 mg, 0.0566 mmol) in DCM (2 mL) 2,2,2-trifluoroacetic acid (0.5 ml, 6.53 mmol) was added and the reaction mixture was stirred for 3 hours at 0° C. The reaction was diluted with DCM (10 ml) and an aqueous saturated solution of NaHCO₃ was added while the pH was allowed to reach ~8. Two phases were separated and the organic layer was dried (Na₂SO₄), filtered and evaporated to afford the title compound (18 mg) as white solid.

LC/MS: QC_3_MIN: Rt=1.970 min; m/z 342 [M+H]+.

The following compounds were prepared using the foregoing methodology, replacing tert-butyl N-[(1R)-1-[[6-[(3,3-dimethyl-1H-isobenzofuran-5-yl)oxy]-3-pyridyl]carbamoyl]propyl]carbamate (Intermediate 49) with the appropriate Boc protected amine.

| Int. | Structure | Name | Boc protected amine | LCMS |
|---|---|---|---|---|
| 62 | 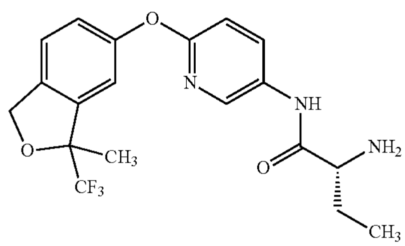 | (2R)-2-amino-N-(6-{[3-methyl-3-(trifluoromethyl)-1,3-dihydro-2-benzofuran-5-yl]oxy}pyridin-3-yl)butanamide (diastereoisomer 1) | tert-butyl N-[(1R)-1-[[6-[[3-methyl-3-(trifluoromethyl)-1H-isobenzofuran-5-yl]oxy]-3-pyridyl]carbamoyl]propyl]carbamate (diastereoisomer 1) (Intermediate 54) | LC/MS: QC_3_MIN: Rt = 1.976 min; m/z 396 [M + H]+. |
| 63 | 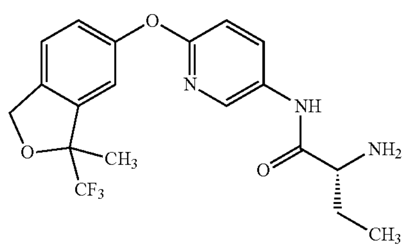 | (2R)-2-amino-N-(6-{[3-methyl-3-(trifluoromethyl)-1,3-dihydro-2-benzofuran-5-yl]oxy}pyridin-3-yl)butanamide (diastereoisomer 2) | tert-butyl N-[(1R)-1-[[6-[[3-methyl-3-(trifluoromethyl)-1H-isobenzofuran-5-yl]oxy]-3-pyridyl]carbamoyl]propyl]carbamate (diastereoisomer 2) (Intermediate 55) | LC/MS: QC_3_MIN: Rt = 1.999 min; m/z 396 [M + H]+. |
| 64 | 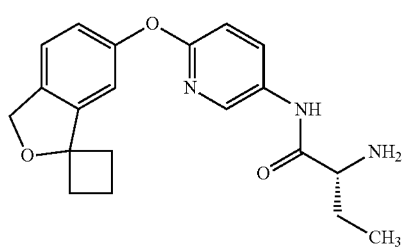 | (2R)-2-amino-N-[6-(3H-spiro[2-benzofuran-1,1'-cyclobutan]-6-yloxy)pyridin-3-yl]butanamide | tert-butyl N-[(1R)-1-[(6-spiro[1H-isobenzofuran-3,1'-cyclobutane]-5-yloxy-3-pyridyl)carbamoyl]propyl]carbamate (Intermediate 56) | LC/MS: QC_3_MIN: Rt = 1.893 min; m/z 354 [M + H]+. |
| 65 | 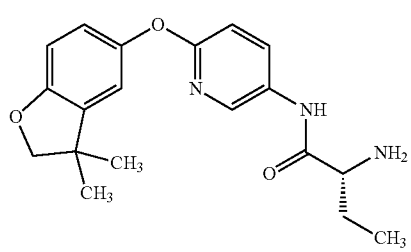 [SMILES: CC[C@@H](N)C(=O)Nc1ccc(Oc2ccc3c(c2)C(C)(C)CO3)nc1] | (2R)-2-amino-N-{6-[(3,3-dimethyl-2,3-dihydro-1-benzofuran-5-yl)oxy]pyridin-3-yl}butanamide | tert-butyl N-[(1R)-1-[[6-[(3,3-dimethyl-1H-isobenzofuran-5-yl)oxy]-3-pyrimidin-5-yl]carbamoyl]propyl]carbamate (Intermediate 57) | LC/MS: QC_3_MIN: Rt = 1.897 min; m/z 342 [M + H]+. |
| 66 | 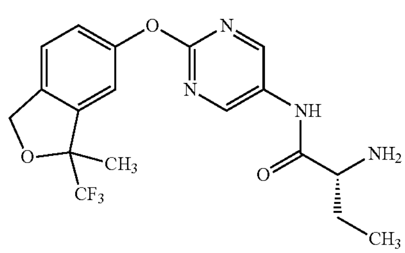 [SMILES: CC[C@@H](N)C(=O)Nc1cnc(Oc2ccc3c(c2)C(C)(C(F)(F)F)OC3)nc1] | (2R)-2-amino-N-(2-{[3-methyl-3-(trifluoromethyl)-1,3-dihydro-2-benzofuran-5-yl]oxy}pyrimidin-5-yl)butanamide (diastereoisomer 1) | tert-butyl N-[(1R)-1-[[2-[[3-methyl-3-(trifluoromethyl)-1H-isobenzofuran-5-yl]oxy]pyrimidin-5-yl]carbamoyl]propyl]carbamate (diastereoisomer 1) (Intermediate 58) | LC/MS: QC_3_MIN: Rt = 2.003 min; m/z 397 [M + H]+. |
| 67 | 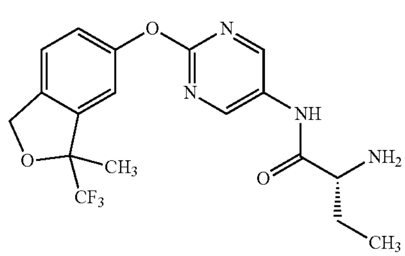 | (2R)-2-amino-N-(2-{[3-methyl-3-(trifluoromethyl)-1,3-dihydro-2-benzofuran-5-yl]oxy}pyrimidin-5-yl)butanamide (diastereoisomer 2) | tert-butyl N-[(1R)-1-[[2-[[3-methyl-3-(trifluoromethyl)-1H-isobenzofuran-5-yl]oxy]pyrimidin-5-yl]carbamoyl]propyl]carbamate (diastereoisomer 2) (Intermediate 59) | LC/MS: QC_3_MIN: Rt = 1.880 min; m/z 397 [M + H]+. |

| Int. | Structure | Name | Boc protected amine | LCMS |
|---|---|---|---|---|
| 68 | 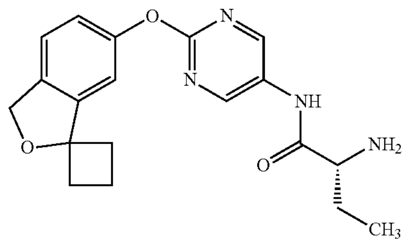 [SMILES: CC[C@@H](N)C(=O)Nc1cnc(Oc2ccc3c(c2)C2(CCC2)OC3)nc1] | (2R)-2-amino-N-[2-(3H-spiro[2-benzofuran-1,1'-cyclobutan]-6-yloxy)pyrimidin-5-yl]butanamide | tert-butyl N-[(1R)-1-[(2-spiro[1H-isobenzofuran-3,1'-cyclobutane]-5-yloxypyrimidin-5-yl)carbamoyl]propyl]carbamate (Intermediate 60) | LC/MS: QC_3_MIN: Rt = 1.890 min; m/z 355 [M + H]+. |

Intermediate 69

1,1-dimethyl-6-(4-nitrophenoxy)-1,3-dihydro-2-benzofuran

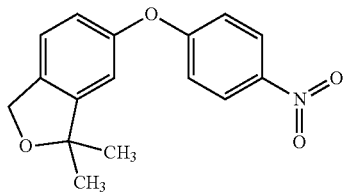

3,3-Dimethyl-1,3-dihydro-2-benzofuran-5-ol (Intermediate 18, 500 mg, 3.04 mmol) and potassium carbonate (1.05 g, 7.6 mmol) were suspended in acetonitrile (7.5 mL). 1-Fluoro-4-nitrobenzene (386 mg, 2.74 mmol) was added and the mixture was stirred under nitrogen at 70° C. overnight and then for 4 hours at 80° C. Further 1-fluoro-4-nitrobenzene (86 mg, 0.6 mmol) was added and the mixture heated to reflux until achieving reaction completion. After cooling water and ethyl acetate were added and the two layers were separated. The organic phase was washed three times with brine, then it was dried over anhydrous Na$_2$SO$_4$ and concentrated to dryness. The residue was triturated in isopropanol and the solid washed with further isopropanol to give the title compound (500 mg).

$^1$H-NMR (400 MHz, DMSO-d$_6$): δ ppm 8.27-8.23 (m, 2H), 7.34 (d, 1H), 7.16 (d, 1H), 7.13-7.09 (m, 2H), 7.07 (dd, 1H), 4.97 (s, 2H), 1.42 (s, 6H). $^{13}$C-NMR (200 MHz, DMSO-d$_6$): δ ppm 163.1, 153.8, 149.7, 142.1, 135.5, 126.2, 123.0, 119.6, 117.1, 113.3, 85.0, 69.6, 28.0.

Intermediate 70

4-[(3,3-dimethyl-1,3-dihydro-2-benzofuran-5-yl)oxy]aniline

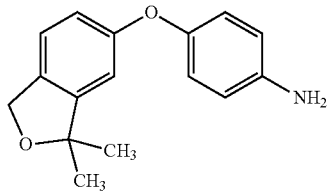 [SMILES: CC1(C)OCc2ccc(Oc3ccc(N)cc3)cc21]

1,1-Dimethyl-6-(4-nitrophenoxy)-1,3-dihydro-2-benzofuran (Intermediate 69, 280 mg, 0.98 mmol) was dissolved in ethanol (5 ml), 5% w/w Pd/C was added and the reaction mixture was stirred for 4 hours under hydrogen atmosphere (2 bar). The catalyst was filtered off and the solvent evaporated to dryness to afford a pale yellow solid, which was purified by re-slurry in Et$_2$O, to afford the title compound (80 mg) as off-white solid.

UPLC_A: Rt=0.67 min, m/z 256 [M+H]+.

$^1$H-NMR (400 MHz, DMSO-d$_6$): δ ppm 7.14 (d, 1H), 6.78-6.73 (m, 3H), 6.70 (dd, 1H), 6.60-6.56 (m, 2H), 4.96 (s, 2H), 4.88 (s, 2H), 1.37 (s, 6H). $^{13}$C-NMR (200 MHz, DMSO-d6): δ ppm 158.6, 148.8, 145.9, 145.3, 131.5, 122.0, 120.6, 115.6, 114.8, 109.1, 84.8, 69.4, 28.0.

Intermediate 71

(2R)-2-amino-N-[4-[(3,3-dimethyl-1H-isobenzofuran-5-yl)oxy]phenyl]-2-methyl-butanamide

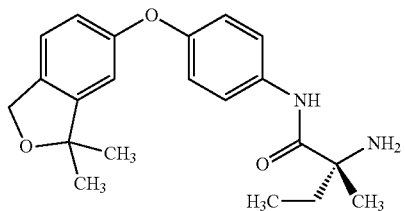 [SMILES: CC[C@@](C)(N)C(=O)Nc1ccc(Oc2ccc3c(c2)C(C)(C)OC3)cc1]

4-[(3,3-dimethyl-1,3-dihydro-2-benzofuran-5-yl)oxy]aniline (Intermediate 70, 120 mg, 0.47 mmol) and methyl-D-isovalinic acid hydrochloride (80 mg, 0.52 mmol) were suspended in a mixture of acetonitrile (1.5 mL) and ethyl acetate (0.5 mL). A 50% w/w solution of T3P in ethyl acetate (1.1 equiv) was added drop wise. The reaction mixture was stirred for 30 minutes at room temperature and then at 80° C. for 4 hours. The reaction mixture was cooled to room temperature and treated with ethyl acetate and saturated Na$_2$CO$_3$ solution and stirred vigorously for 10 min. Two layers were separated and the organic layer was washed twice with brine, dried over Na$_2$SO$_4$ and evaporated to dryness. The residue was purified by flash chromatography on silica gel using dichloromethane/Methanol from 100:0 to 90:10 as eluent to afford the title compound (140 mg).

UPLC_A: Rt=0.72 min, m/z 355 [M+H]+.

Intermediate 72

2-[(2-propyn-1-yloxy)methyl]furan

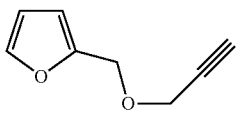

To a suspension of sodium hydride (1.570 g, 39.2 mmol) in DMF (46 ml) stirred under argon at 0° C. a solution of 2-furanylmethanol (3.5 g, 35.7 mmol) in DMF (4 ml) was added dropwise over 20 minutes. The reaction mixture was stirred at 0° C. for 15 minutes. 3-bromo-1-propyne (4.24 g, 35.7 mmol) 80% in toluene was dropped in 10 minutes at 0° C., then the mixture was left stirring at room temperature overnight. Water was added and then the mixture was extracted with ethyl ether 3 times. The organic phase was dried over sodium sulphate and concentrated under vacuum. The residue was purified by flash chromatography on silica gel (Biotage SP1 instrument), eluting with a gradient cyclohexane/ethyl acetate 95/5 to 85/15. Evaporation afforded the title compound (1.63 g, 35% yield).

$^1$H NMR (400 MHz, DMSO-$d_6$): δ ppm 7.66 (1H, d), 6.41-6.49 (2H, m), 4.46 (2H, s), 4.12 (2H, d), 3.48 (1H, t).

Intermediate 73

1,3-dihydro-2-benzofuran-5-ol

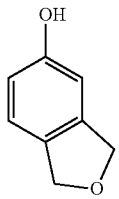

To a solution of [2-[(2-propyn-1-yloxy)methyl]furan] (Intermediate 72, 1.63 g, 11.97 mmol), in acetonitrile (60 ml) stirred under argon at room temperature was added neat gold trichloride (0.182 g, 0.599 mmol). The reaction mixture was stirred overnight at room temperature. Gold trichloride was then added (120 mg) and after 2 hours another gold trichloride addition was carried out (226 mg). After 1 hour the mixture was concentrated and the crude was purified by flash chromatography on silica gel (Biotage SP1), eluting with cyclohexane/ethyl acetate 90/10. Evaporation afforded the title compound 1,3-dihydro-2-benzofuran-5-ol (356 mg) and 1,3-dihydro-2-benzofuran-4-ol (100 mg).

$^1$H NMR (400 MHz, DMSO-$d_6$): δ ppm 9.36 (1H, s), 7.11-7.02 (1H, m), 6.70-6.61 (2H, m), 4.89 (4H, m).

Intermediate 74

5[(4-nitrophenyl)oxy]-1,3-dihydro-2-benzofuran

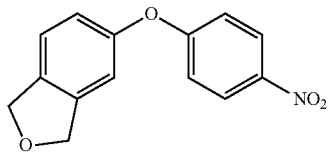 [SMILES: O=[N+]([O-])c1ccc(Oc2ccc3c(c2)COC3)cc1]

A solution of 1,3-dihydro-2-benzofuran-5-ol (Intermediate 73, 100 mg, 0.734 mmol), 1-fluoro-4-nitrobenzene (109 mg, 0.771 mmol) and potassium carbonate (508 mg, 3.67 mmol) in acetonitrile (10 ml) was stirred under argon at 100° C. in a closed vial for 2 hours. The solid was filtered and washed with dichloromethane. The organic phase was concentrated under vacuum to afford title compound (184 mg, 96% yield)

$^1$H NMR (400 MHz, DMSO-$d_6$): δ ppm 8.29-8.21 (2H, m), 7.42 (1H, d), 7.21-7.06 (4H, m), 5.01 (4H, d).

Intermediate 75

4-(1,3-dihydro-2-benzofuran-5-yloxy)aniline

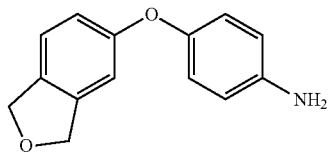

A solution of 5-[(4-nitrophenyl)oxy]-1,3-dihydro-2-benzofuran (Intermediate 74, 190 mg, 0.739 mmol), hydrazine hydrate (0.046 ml, 1.477 mmol) and Pd/C (157 mg, 0.148 mmol) in ethanol (6 ml) was stirred under argon at 90° C. After 4.5 hours 0.2 equivalents of Pd/C and 2 equivalents of hydrazine hydrate were added. After 1 more hour, the reaction mixture was cooled to room temperature and then filtered over celite and washed with methanol. The organic phase was concentrated and the residue was purified by SCX to afford the title compound (152 mg).

$^1$H NMR (400 MHz, DMSO-$d_6$): δ ppm 7.21 (1H, m), 6.81-6.71 (4H, m), 6.61-6.55 (2H, m), 5.02-4.95 (2H, m), 4.94-4.89 (4H, m).

Intermediate 76

1,1-dimethylethyl((1R)-2-{[4-(1,3-dihydro-2-benzofuran-5-yloxy)phenyl]amino}-1-methyl-2-oxoethyl)carbamate

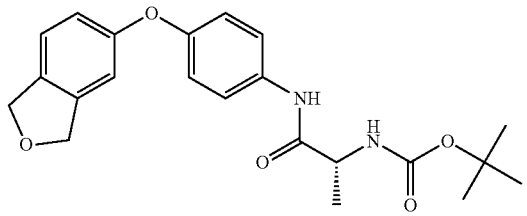 [SMILES: C[C@@H](NC(=O)OC(C)(C)C)C(=O)Nc1ccc(Oc2ccc3c(c2)COC3)cc1]

A suspension of N-{[(1,1-dimethylethyl)oxy]carbonyl}-D-alanine (97 mg, 0.515 mmol), DIPEA (0.138 ml, 0.792 mmol) and TBTU (191 mg, 0.594 mmol) in 1,2-dichloroethane (3 ml) was stirred under argon at room temperature for 45 min. 4-(1,3-dihydro-2-benzofuran-5-yloxy)aniline (Intermediate 75, 81 mg, 0.356 mmol) was added and the mixture was left under stirring at room temperature overnight. Brine was added and the mixture was separated in a separator tube. The aqueous phase was extracted twice with dichloromethane. The organic phase was dried over sodium sulphate and concentrated under vacuum. The residue was purified by chromatography on silica gel (Biotage SP1), using as eluents a gradient cyclohexane/ethyl acetate from 100:0 to 85:15 to afford the title compound (130 mg).

¹H NMR (400 MHz, DMSO-d6): δ ppm 9.99-9.92 (1H, m), 7.61 (2H, d), 7.32-7.26 (1H, m), 7.11-7.05 (1H, m), 6.99 (2H, d), 6.93-6.86 (2H, m), 4.96 (4H, d), 4.15-4.05 (1H, m), 1.39 (9H, s), 1.26 (3H, d).

Intermediate 77

N¹-[4-(1,3-dihydro-2-benzofuran-5-yloxy)phenyl]-D-alaninamide

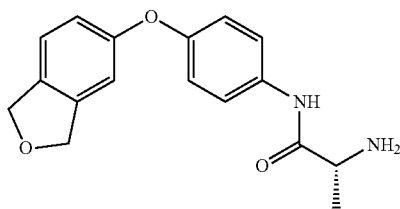 [SMILES: C[C@@H](N)C(=O)Nc1ccc(Oc2ccc3c(c2)COC3)cc1]

A solution of 1,1-dimethylethyl((1R)-2-{[4-(1,3-dihydro-2-benzofuran-5-yloxy)phenyl]amino}-1-methyl-2-oxoethyl)carbamate (Intermediate 76, 130 mg, 0.326 mmol) and TFA (1 ml) in dichloromethane (4 ml) was stirred under argon at room temperature. The reaction mixture was stirred at room temperature for 1 hour. The mixture was concentrated and the residue was purified by SCX to afford the title compound (94 mg), which was directly used in the next step.

UPLC_A: Rt=0.64 min; m/z 299 [M+H]+

Example 1

3-[2-[(3,3-dimethyl-1H-isobenzofuran-5-yl)oxy]pyrimidin-5-yl]-5,5-dimethyl-imidazolidine-2,4-dione

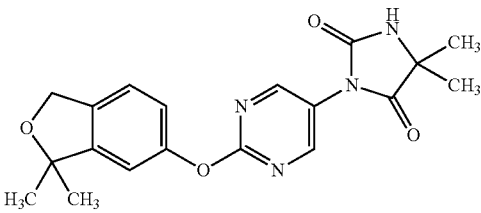

To a solution of 3,3-dimethyl-1H-isobenzofuran-5-ol (Intermediate 18, 15 mg, 0.0914 mmol) in DMF (1 ml) 3-(2-chloropyrimidin-5-yl)-5,5-dimethyl-imidazolidine-2,4-dione (Intermediate 1, 19.785 mg, 0.0822 mmol) and dipotassium carbonate (25.252 mg, 0.1827 mmol) were added. The reaction mixture was stirred at 80° C. for 1 hour. The reaction was quenched with saturated ammonium chloride (5 ml) and extracted with ethyl acetate 10 ml. The organic layer was washed with brine (3×10 ml) dried over sodium sulphate and concentrated under vacuum. The residue was purified by flash chromatography on silica gel (Biotage system) using a SNAP 10 g as column and cyclohexane/ethyl acetate from 75:25 to 30:70 as eluent to afford the title compound (6 mg).

LC/MS: QC_3_MIN: Rt=2.277 min; m/z 369 [M+H]+, 759 [2M+Na]+.

¹H-NMR (400 MHz, DMSO-d₆): δ ppm 8.73 (br.s, 1H), 8.71 (s, 2H), 7.31 (d, 1H), 7.19 (d, 1H), 7.12 (dd, 1H), 4.97 (s, 2H), 1.40-1.44 (m, 12H).

The following compounds were prepared using the foregoing methodology, replacing 3,3-dimethyl-1H-isobenzofuran-5-ol (Intermediate 18) with the appropriate Phenol. Final products were purified by flash-chromatography (Silica cartridge; cyclohexane/EtOAc or other appropriate solvent system).

| Ex. | Structure | Name | Phenol | LCMS | NMR |
|---|---|---|---|---|---|
| 2 | 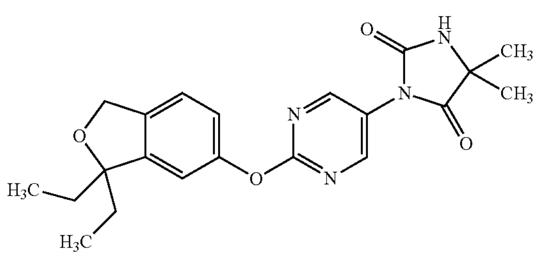 [SMILES: CCC1(CC)OCc2ccc(Oc3ncc(N4C(=O)NC(C)(C)C4=O)cn3)cc21] | 3-[2-[(3,3-diethyl-1H-isobenzofuran-5-yl)oxy]pyrimidin-5-yl]-5,5-dimethyl-imidazolidine-2,4-dione | 3,3-diethyl-1,3-dihydro-2-benzofuran-5-ol (Intermediate 19) | LC/MS: QC_3_MIN: Rt = 2.397 min; m/z 397 [M + H]+, 815 [2M + Na]+. | ¹H-NMR (400 MHz, DMSO-d₆): δ ppm 8.73 (br. s, 1H), 8.70 (s, 2H), 7.31 (d, 1H), 7.13 (dd, 1H), 7.08 (d, 1H), 5.01 (s, 2H), 1.74 (q, 4H), 1.42 (s, 6H), 0.69 (t, 6H). |
| 3 | 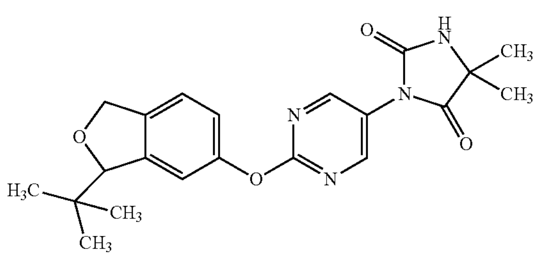 | 3-[2-[(3-tert-butyl-1,3-dihydroisobenzofuran-5-yl)oxy]pyrimidin-5-yl]-5,5-dimethyl-imidazolidine-2,4-dione (enantiomer 1) | 3-tert-butyl-1,3-dihydro-2-benzofuran-5-ol (Intermediate 30 enantiomer 1) | LC/MS: QC_3_MIN: Rt = 2.144 min; m/z 397 [M + H]+, 815 [2M + Na]+. | ¹H-NMR (400 MHz, DMSO-d₆): δ ppm 8.73 (br. s, 1H), 8.70 (s, 2H), 7.33-7.38 (m, 1H), 7.15-7.20 (m, 2H), 4.94-5.09 (m, 2H), 4.83-4.87 (m, 1H), 1.42 (s, 6H), 0.91 (s, 9H). |

-continued

| Ex. | Structure | Name | Phenol | LCMS | NMR |
|---|---|---|---|---|---|
| 4 | 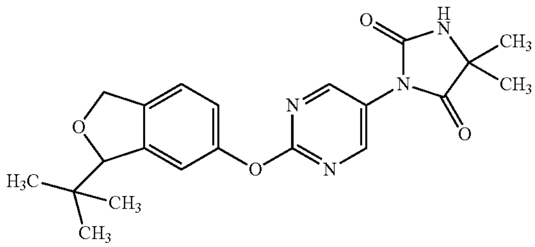 | 3-[2-[(3-tert-butyl-1,3-dihydroisobenzofuran-5-yl)oxy]pyrimidin-5-yl-5,5-dimethylimidazolidine-2,4-dione (enantiomer 2) | 3-tert-butyl-1,3-dihydro-2-benzofuran-5-ol (Intermediate 31 enantiomer 2) | LC/MS: QC_3_MIN: Rt = 2.197 min; m/z 397 [M + H]+, 815 [2M + Na]+ | $^1$H-NMR (400 MHz, DMSO-$d_6$): δ ppm 8.73 (br. s, 1H), 8.70 (s, 2H), 7.33-7.38 (m, 1H), 7.15-7.20 (m, 2H), 4.94-5.09 (m, 2H), 4.83-4.87 (m, 1H), 1.42 (s, 6H), 0.91 (s, 9H). |
| 5 | 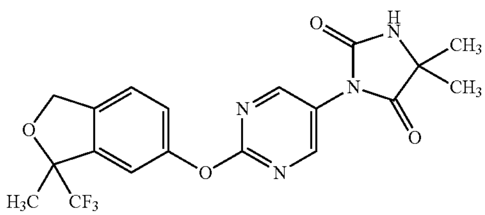 [SMILES: CC1(C)NC(=O)N(c2cnc(Oc3ccc4c(c3)C(C)(C(F)(F)F)OC4)nc2)C1=O] | 5,5-dimethyl-3-[2-[[3-methyl-3-(trifluoromethyl)-1H-isobenzofuran-5-yl]oxy]pyrimidin-5-yl]imidazolidine-2,4-dione (enantiomer 1) | 3-methyl-3-(trifluoromethyl)-1,3-dihydro-2-benzofuran-5-ol (Intermediate 32 enantiomer 1) | LC/MS: QC_3_MIN: Rt = 2.228 min; m/z 423 [M + H]+. | $^1$H-NMR (400 MHz, DMSO-$d_6$): δ ppm 8.74 (s, 1H), 8.72 (s, 2H), 7.47 (d, 1H), 7.38-7.42 (m, 1H), 7.35 (dd, 1H), 5.12-5.23 (m, 2H), 1.66 (s, 3H), 1.42 (s, 6H). |
| 6 | 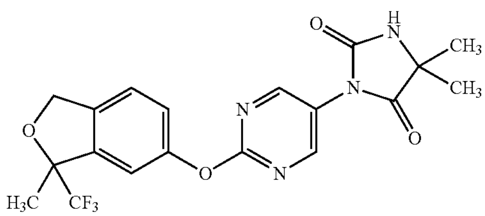 | 5,5-dimethyl-3-[2-[[3-methyl-3-(trifluoromethyl)-1H-isobenzofuran-5-yl]oxy]pyrimidin-5-yl]imidazolidine-2,4-dione (enantiomer 2) | 3-methyl-3-(trifluoromethyl)-1,3-dihydro-2-benzofuran-5-ol (Intermediate 33 enantiomer 2) | LC/MS: QC_3_MIN: Rt = 2.249 min; m/z 423 [M + H]+. | $^1$H-NMR (400 MHz, DMSO-$d_6$): δ ppm 8.74 (s, 1H), 8.72 (s, 2H), 7.47 (d, 1H), 7.38-7.42 (m, 1H), 7.35 (dd, 1H), 5.12-5.23 (m, 2H), 1.66 (s, 3H), 1.42 (s, 6H). |
| 7 | 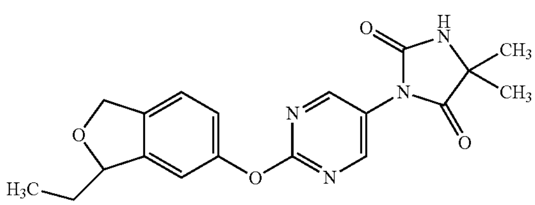 [SMILES: CCC1OCc2ccc(Oc3ncc(N4C(=O)NC(C)(C)C4=O)cn3)cc21] | 3-[2-[(3-ethyl-1,3-dihydroisobenzofuran-5-yl)oxy]pyrimidin-5-yl]-5,5-dimethylimidazolidine-2,4-dione (enantiomer 1) | 3-ethyl-1,3-dihydro-2-benzofuran-5-ol (Intermediate 34 enantiomer 1) | LC/MS: QC_3_MIN: Rt = 1.885 min; m/z 369 [M + H]+. | $^1$H-NMR (400 MHz, DMSO-$d_6$): δ ppm 8.73 (br. s, 1H), 8.70 (s, 2H), 7.34 (d, 1H), 7.12-7.18 (m, 2H), 5.09-5.14 (m, 1H), 4.93-5.06 (m, 2H), 1.81-1.92 (m, 1H), 1.59-1.70 (m, 1H), 1.42 (s, 6H), 0.89 (t, 3H) |
| 8 | 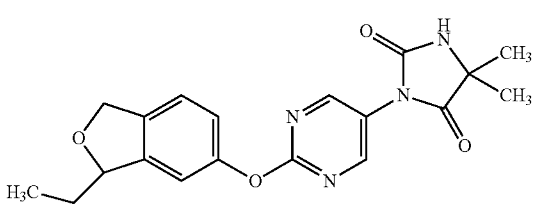 [SMILES: CCC1OCc2ccc(Oc3ncc(N4C(=O)NC(C)(C)C4=O)cn3)cc21] | 3-[2-[(3-ethyl-1,3-dihydroisobenzofuran-5-yl)oxy]pyrimidin-5-yl]-5,5-dimethylimidazolidine-2,4-dione (enantiomer 2) | 3-ethyl-1,3-dihydro-2-benzofuran-5-ol (Intermediate 35 enantiomer 2) | LC/MS: QC_3_MIN: Rt = 2.040 min; m/z 369 [M + H]+. | $^1$H-NMR (400 MHz, DMSO-$d_6$): δ ppm 8.73 (br. s, 1H), 8.70 (s, 2H), 7.34 (d, 1H), 7.12-7.18 (m, 2H), 5.09-5.14 (m, 1H), 4.93-5.06 (m, 2H), 1.81-1.92 (m, 1H), 1.59-1.70 (m, 1H), 1.42 (s, 6H), 0.89 (t, 3H). |
| 9 | 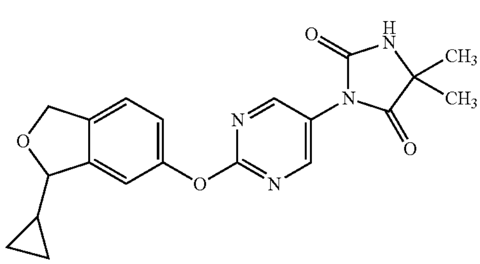 [SMILES: CC1(C)NC(=O)N(c2cnc(Oc3ccc4c(c3)C(C3CC3)OC4)nc2)C1=O] | 3-[2-[(3-cyclopropyl-1,3-dihydroisobenzofuran-5-yl)oxy]pyrimidin-5-yl]-5,5-dimethylimidazolidine-2,4-dione (enantiomer 1) | 3-cyclopropyl-1,3-dihydro-2-benzofuran-5-ol (Intermediate 36 enantiomer 1) | LC/MS: QC_3_MIN: Rt = 2.051 min; m/z 381 [M + H]+, 783 [2M + Na]+ | $^1$H-NMR (400 MHz, DMSO-$d_6$): δ ppm 8.73 (br. s, 1H), 8.70 (s, 2H), 7.35 (d, 1H), 7.19-7.22 (m, 1H), 7.16 (dd, 1H), 5.01-5.08 (m, 1H), 4.90-4.96 (m, 1H), 4.54-4.59 (m, 1H), 1.42 (s, 6H), 1.02-1.12 (m, 1H), 0.44-0.58 (m, 3H), 0.32-0.39 (m, 1H). |

| Ex. | Structure | Name | Phenol | LCMS | NMR |
|---|---|---|---|---|---|
| 10 | 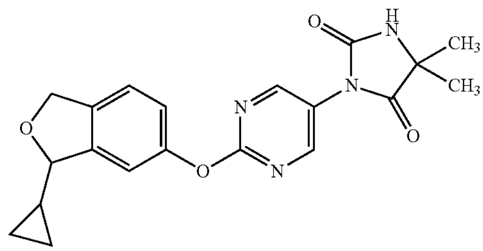 [SMILES: CC1(C)NC(=O)N(c2cnc(Oc3ccc4c(c3)C(C3CC3)OC4)nc2)C1=O] | 3-[2-[(3-cyclopropyl-1,3-dihydroisobenzofuran-5-yl)oxy]pyrimidin-5-yl]-5,5-dimethyl-imidazolidine-2,4-dione (enantiomer 2) | 3-cyclopropyl-1,3-dihydro-2-benzofuran-5-ol (Intermediate 37 enantiomer 2) | LC/MS: QC_3_MIN: Rt = 1.938 min; m/z 381 [M + H]+. | $^1$H-NMR (400 MHz, DMSO-d$_6$): δ ppm 8.73 (br. s, 1H), 8.70 (s, 2H), 7.35 (d, 1H), 7.19-7.22 (m, 1H), 7.16 (dd, 1H), 5.01-5.08 (m, 1H), 4.90-4.96 (m, 1H), 4.54-4.59 (m, 1H), 1.42 (s, 6H), 1.02-1.12 (m, 1H), 0.44-0.58 (m, 3H), 0.32-0.39 (m, 1H). |
| 11 | 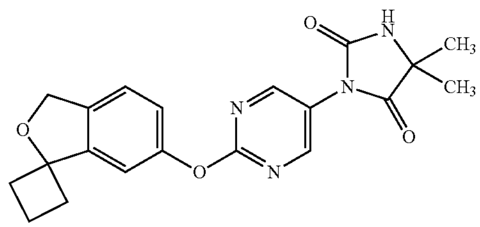 [SMILES: CC1(C)NC(=O)N(c2cnc(Oc3ccc4c(c3)C3(CCC3)OC4)nc2)C1=O] | 5,5-dimethyl-3-(2-spiro[1H-isobenzofuran-3,1'-cyclobutane]-5-yloxypyrimidin-5-yl)imidazolidine-2,4-dione | 3H-spiro[2-benzofuran-1,1'-cyclobutan]-6-ol (Intermediate 24) | LC/MS: QC_3_MIN: Rt = 2.188 min; m/z 381 [M + H]+. | $^1$H-NMR (400 MHz, DMSO-d$_6$): δ ppm 8.73 (br. s, 1H), 8.71 (s, 2H), 7.45 (d, 1H), 7.31 (d, 1H), 7.15 (dd, 1H), 4.97 (s, 2H), 2.42-2.52 (m, 2H), 2.28-2.38 (m, 2H), 1.77-1.99 (m, 2H), 1.42 (s, 6H). |
| 12 | 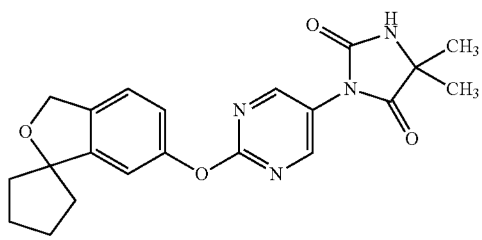 [SMILES: CC1(C)NC(=O)N(c2cnc(Oc3ccc4c(c3)C3(CCCC3)OC4)nc2)C1=O] | 5,5-dimethyl-3-(2-spiro[1H-isobenzofuran-3,1'-cyclopentane]-5-yloxypyrimidin-5-yl)imidazolidine-2,4-dione | 3H-spiro[2-benzofuran-1,1'-cyclopentan]-6-ol (Intermediate 25) | LC/MS: QC_3_MIN: Rt = 1.904 min; m/z 395 [M + H]+, 811 [2M + Na]+. | $^1$H-NMR (400 MHz, DMSO-d$_6$): δ ppm 8.73 (br. s, 1H), 8.70 (s, 2H), 7.31 (d, 1H), 7.18 (d, 1H), 7.11 (dd, 1H), 4.93 (s, 2H), 1.72-1.98 (m, 8H), 1.42 (s, 6H). |
| 13 | 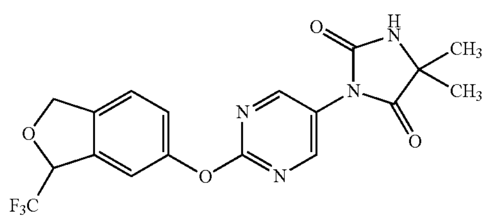 | 5,5-dimethyl-3-[2-[[3-(trifluoromethyl)-1,3-dihydroisobenzofuran-5-yl]oxy]pyrimidin-5-yl]imidazolidine-2,4-dione (enantiomer 1) | 3-(trifluoromethyl)-1,3-dihydroisobenzofuran-5-ol (Intermediate 28 enantiomer 1) | LC/MS: QC_3_MIN: Rt = 2.174 min; m/z 409 [M + H]+. | $^1$H-NMR (400 MHz, DMSO-d$_6$): δ ppm 8.74 (br. s, 1H), 8.72 (s, 2H), 7.51 (d, 1H), 7.37 (dd, 1H), 7.30-7.33 (m, 1H), 5.82-5.90 (m, 1H), 5.17-5.26 (m, 2H), 1.42 (s, 6H). |
| 14 | 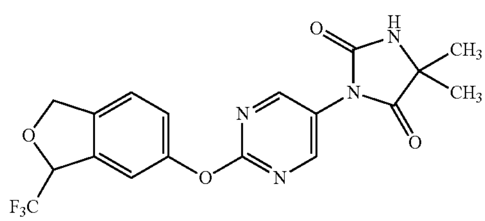 | 5,5-dimethyl-3-[2-[[3-(trifluoromethyl)-1,3-dihydroisobenzofuran-5-yl]oxy]pyrimidin-5-yl]imidazolidine-2,4-dione (enantiomer 2) | 3-(trifluoromethyl)-1,3-dihydroisobenzofuran-5-ol (Intermediate 29 enantiomer 2) | LC/MS: QC_3_MIN: Rt = 2.249 min; m/z 409 [M + H]+. | $^1$H-NMR (400 MHz, DMSO-d$_6$): δ ppm 8.74 (br. s, 1H), 8.72 (s, 2H), 7.51 (d, 1H), 7.37 (dd, 1H), 7.30-7.33 (m, 1H), 5.82-5.90 (m, 1H), 5.17-5.26 (m, 2H), 1.42 (s, 6H). |
| 15 | 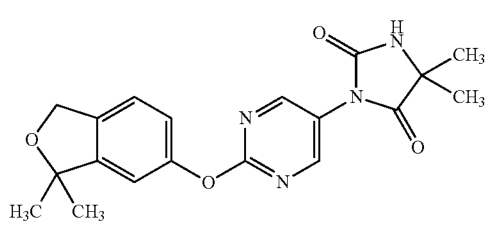 [SMILES: CC1(C)NC(=O)N(c2cnc(Oc3ccc4c(c3)C(C)(C)OC4)nc2)C1=O] | 3-[2-[(3,3-dimethyl-2H-benzofuran-5-yl)oxy]pyrimidin-5-yl]-5,5-dimethyl-imidazolidine-2,4-dione | 3,3-dimethyl-2H-benzofuran-5-ol (Intermediate 44) | LC/MS: QC_3_MIN: Rt = 2.172 min; m/z 369 [M + H]+, 759 [2M + Na]+. | $^1$H-NMR (400 MHz, DMSO-d$_6$): δ ppm 8.72 (br. s, 1H), 8.68 (s, 2H), 7.11 (d, 1H), 6.94 (dd, 1H), 6.79 (d, 1H), 4.25 (s, 2H), 1.42 (s, 6H), 1.29 (s, 6H). |

| Ex. | Structure | Name | Phenol | LCMS | NMR |
|---|---|---|---|---|---|
| 16 | 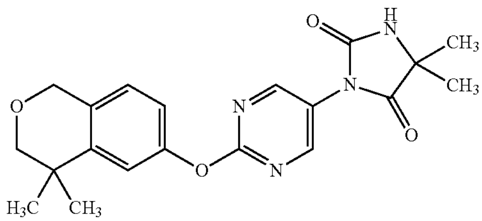 [SMILES: CC1(C)NC(=O)N(c2cnc(Oc3ccc4c(c3)C(C)(C)COC4)nc2)C1=O] | 3-[2-(4,4-dimethyliso-chroman-6-yl)oxypyrimidin-5-yl]-5,5-dimethyl-imidazolidine-2,4-dione | 4,4-dimethyl-3,4-dihydro-1H-isochromen-6-ol (Intermediate 42) | LC/MS: QC_3_MIN: Rt = 1.766 min; m/z 383 [M + H]+, 787 [2M + Na]+. | $^1$H-NMR (400 MHz, DMSO-d$_6$): δ ppm 8.73 (br. s, 1H), 8.70 (s, 2H), 7.27 (d, 1H), 7.07 (d, 1H), 7.01 (dd, 1H), 4.73 (s, 2H), 3.55 (s, 2H), 1.42 (s, 6H), 1.20 (s, 6H). |

Example 17

(5R)-3-[2-[(3,3-dimethyl-1H-isobenzofuran-5-yl)oxy]pyrimidin-5-yl]-5-ethyl-5-methyl-imidazolidine-2,4-dione

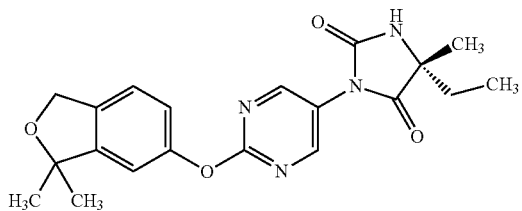

To a solution of 3,3-dimethyl-1H-isobenzofuran-5-ol (Intermediate 18, 15 mg, 0.0914 mmol) in DMF (1 ml) (5R)-3-(2-chloropyrimidin-5-yl)-5-ethyl-5-methyl-imidazolidine-2,4-dione (Intermediate 2, 20.938 mg, 0.0822 mmol) and dipotassium carbonate (25.252 mg, 0.1827 mmol) were added. The reaction mixture was stirred at 80° C. for 1 hour. The reaction was quenched with an aqueous saturated solution of ammonium chloride (5 ml) and extracted with ethyl acetate 10 ml. The organic layer was washed with brine (3×10 ml) dried over sodium sulphate and concentrated under vacuum. The residue was purified by flash chromatography on silica gel (Biotage system) using a SNAP 10 g as column and cyclohexane/ethyl acetate from 75:25 to 30:70 as eluent to afford the title compound (20 mg).

LC/MS: QC_3_MIN: Rt=2.184 min; m/z 383 [M+H]+, 787 [2M+Na]+.

$^1$H-NMR (400 MHz, DMSO-d$_6$): δ ppm 8.70 (s, 3H), 7.31 (d, 1H), 7.19 (d, 1H), 7.12 (dd, 1H), 4.97 (s, 2H), 1.74-1.83 (m, 1H), 1.62-1.71 (m, 1H), 1.42 (s, 6H), 1.40 (s, 3H), 0.88 (t, 3H).

The following compounds were prepared using the foregoing methodology, replacing 3,3-dimethyl-1H-isobenzofuran-5-ol (Intermediate 18) with the appropriate phenol. Final products were purified by flash-chromatography (Silica cartridge; cyclohexane/EtOAc or other appropriate solvent system).

| Ex. | Structure | Name | Phenol | LCMS | NMR |
|---|---|---|---|---|---|
| 18 | 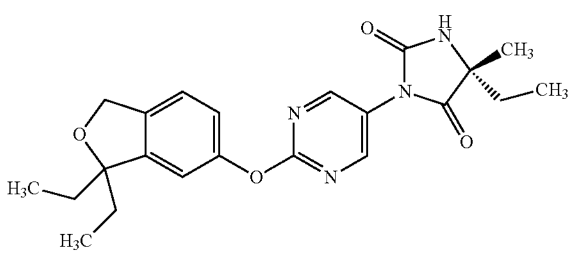 [SMILES: CCC1(CC)OCc2ccc(Oc3ncc(N4C(=O)N[C@](C)(CC)C4=O)cn3)cc21] | (5R)-3-[2-[(3,3-diethyl-1H-isobenzofuran-5-yl)oxy]pyrimidin-5-yl]-5-ethyl-5-methyl-imidazolidine-2,4-dione | 3,3-diethyl-1,3-dihydro-2-benzofuran-5-ol (Intermediate 19) | LC/MS: QC_3_MIN: Rt = 2.241 min; m/z 411 [M + H]+, 843 [2M + Na]+. | $^1$H-NMR (400 MHz, DMSO-d$_6$): δ ppm 8.70 (s, 3H), 7.31 (d, 1H), 7.13 (dd, 1H), 7.08 (d, 1H), 5.01 (s, 2H), 1.61-1.83 (m, 6H), 1.40 (s, 3H), 0.87 (t, 3H), 0.69 (t, 6H). |
| 19 | 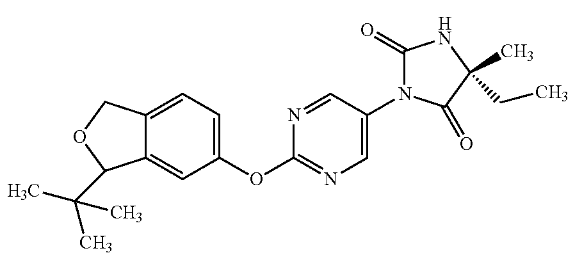 [SMILES: CC[C@@]1(C)NC(=O)N(c2cnc(Oc3ccc4c(c3)C(C(C)(C)C)OC4)nc2)C1=O] | (5R)-3-[2-[(3-tert-butyl-1,3-dihydroiso-benzofuran-5-yl)oxy]pyrimidin-5-yl]-5-ethyl-5-methyl-imidazolidine-2,4-dione (diastereoisomer 1) | 3-tert-butyl-1,3-dihydro-2-benzofuran-5-ol (Intermediate 30 enantiomer 1) | LC/MS: QC_3_MIN: Rt = 2.185 min; m/z 411 [M + H]+, 843 [2M + Na]+. | $^1$H-NMR (400 MHz, DMSO-d$_6$): δ ppm 8.68-8.73 (m, 3H), 7.34-7.38 (m, 1H), 7.15-7.20 (m, 2H), 5.03-5.09 (m, 1H), 4.94-4.99 (m, 1H), 4.84-4.88 (m, 1H), 1.72-1.82 (m, 1H), 1.61-1.71 (m, 1H), 1.40 (s, 3H), 0.91 (s, 9H), 0.87 (t, 3H). |

-continued

| Ex. | Structure | Name | Phenol | LCMS | NMR |
|---|---|---|---|---|---|
| 20 | 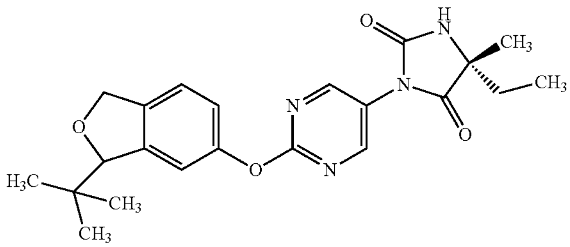 [SMILES: CC[C@@]1(C)NC(=O)N(c2cnc(Oc3ccc4c(c3)C(C(C)(C)C)OC4)nc2)C1=O] | (5R)-3-[2-[(3-tert-butyl-1,3-dihydroisobenzofuran-5-yl)oxy]pyrimidin-5-yl]-5-ethyl-5-methyl-imidazolidine-2,4-dione (diastereoisomer 2) | 3-tert-butyl-1,3-dihydro-2-benzofuran-5-ol (Intermediate 31 enantiomer 2) | LC/MS: QC_3_MIN: Rt = 2.217 min; m/z 411 [M + H]+. | $^1$H-NMR (400 MHz, DMSO-$d_6$): δ ppm 8.68-8.73 (m, 3H), 7.34-7.38 (m, 1H), 7.15-7.20 (m, 2H), 5.03-5.09 (m, 1H), 4.94-4.99 (m, 1H), 4.84-4.88 (m, 1H), 1.72-1.82 (m, 1H), 1.61-1.71 (m, 1H), 1.40 (s, 3H), 0.91 (s, 9H), 0.87 (t, 3H). |
| 21 | 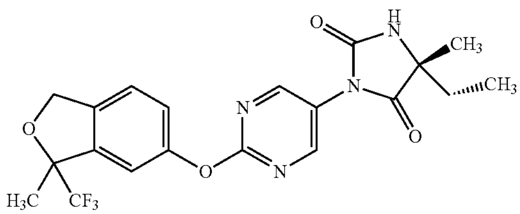 | (5R)-5-ethyl-5-methyl-3-[2-[[3-methyl-3-(trifluoromethyl)-1H-isobenzofuran-5-yl]oxy]pyrimidin-5-yl]imidazolidine-2,4-dione (diastereoisomer 1) | 3-methyl-3-(trifluoromethyl)-1,3-dihydro-2-benzofuran-5-ol (Intermediate 32 enantiomer 1) | LC/MS: QC_3_MIN: Rt = 2.309 min; m/z 437 [M + H]+, 895 [2M + Na]+. | $^1$H-NMR (400 MHz, DMSO-$d_6$): δ ppm 8.69-8.74 (m, 3H), 7.47 (d, 1H), 7.38-7.41 (m, 1H), 7.35 (dd, 1H), 5.12-5.23 (m, 1H), 1.73-1.83 (m, 1H), 1.62-1.72 (m, 4H), 1.40 (s, 3H), 0.87 (t, 3H). |
| 22 | 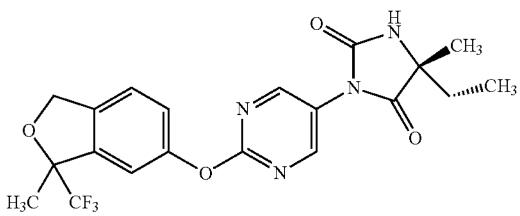 | (5R)-5-ethyl-5-methyl-3-[2-[[3-methyl-3-(trifluoromethyl)-1H-isobenzofuran-5-yl]oxy]pyrimidin-5-yl]imidazolidine-2,4-dione (diastereoisomer 2) | 3-methyl-3-(trifluoromethyl)-1,3-dihydro-2-benzofuran-5-ol (Intermediate 33 enantiomer 2) | LC/MS: QC_3_MIN: Rt = 2.313 min; m/z 437 [M + H]+, 895 [2M + Na]+. | $^1$H-NMR (400 MHz, DMSO-$d_6$): δ ppm 8.69-8.74 (m, 3H), 7.47 (d, 1H), 7.38-7.41 (m, 1H), 7.35 (dd, 1H), 5.12-5.23 (m, 1H), 1.73-1.83 (m, 1H), 1.62-1.72 (m, 4H), 1.40 (s, 3H), 0.87 (t, 3H). |
| 23 | 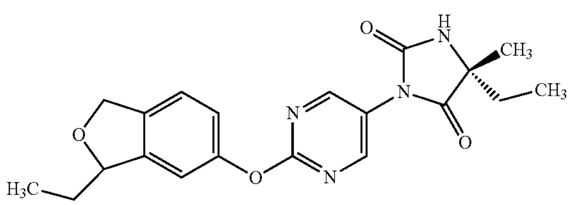 [SMILES: CCC1OCc2ccc(Oc3ncc(N4C(=O)N[C@](C)(CC)C4=O)cn3)cc21] | (5R)-5-ethyl-3-[2-[(3-ethyl-1,3-dihydroisobenzofuran-5-yl)oxy]pyrimidin-5-yl]-5-methyl-imidazolidine-2,4-dione (diastereoisomer 1) | 3-ethyl-1,3-dihydro-2-benzofuran-5-ol (Intermediate 34 enantiomer 1) | LC/MS: QC_3_MIN: Rt = 2.201 min; m/z 383 [M + H]+. | $^1$H-NMR (400 MHz, DMSO-$d_6$): δ ppm 8.68-8.73 (m, 3H), 7.34 (d, 1H), 7.12-7.18 (m, 2H), 5.09-5.14 (m, 1H), 5.00-5.06 (m, 1H), 4.93-4.99 (m, 1H), 1.72-1.93 (m, 2H), 1.58-1.71 (m, 2H), 1.40 (s, 3H), 0.83-0.93 (m, 6H). |
| 24 | 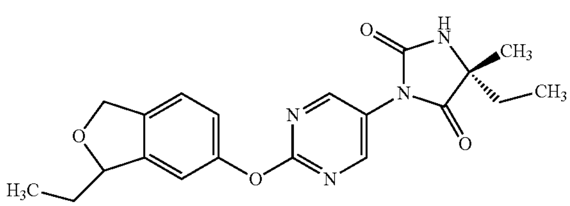 [SMILES: CCC1OCc2ccc(Oc3ncc(N4C(=O)N[C@](C)(CC)C4=O)cn3)cc21] | (5R)-5-ethyl-3-[2-[(3-ethyl-1,3-dihydroisobenzofuran-5-yl)oxy]pyrimidin-5-yl]-5-methyl-imidazolidine-2,4-dione (diastereoisomer 2) | 3-ethyl-1,3-dihydro-2-benzofuran-5-ol (Intermediate 35 enantiomer 2) | LC/MS: QC_3_MIN: Rt = 1.782 min; m/z 383 [M + H]+. | $^1$H-NMR (400 MHz, DMSO-$d_6$): δ ppm 8.68-8.73 (m, 3H), 7.34 (d, 1H), 7.12-7.18 (m, 2H), 5.09-5.14 (m, 1H), 5.00-5.06 (m, 1H), 4.93-4.99 (m, 1H), 1.72-1.93 (m, 2H), 1.58-1.71 (m, 2H), 1.40 (s, 3H), 0.83-0.93 (m, 6H). |

| Ex. | Structure | Name | Phenol | LCMS | NMR |
|---|---|---|---|---|---|
| 25 | 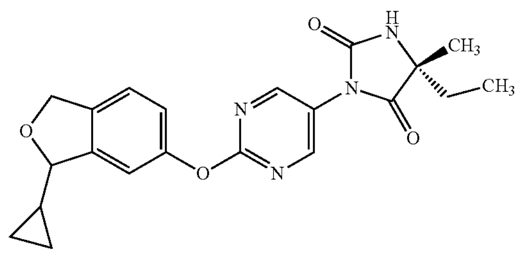 [SMILES: CC[C@@]1(C)NC(=O)N(c2cnc(Oc3ccc4c(c3)C(C3CC3)OC4)nc2)C1=O] | (5R)-3-[2-[(3-cyclopropyl-1,3-dihydroisobenzofuran-5-yl)oxy]pyrimidin-5-yl]-5-ethyl-5-methyl-imidazolidine-2,4-dione (diastereoisomer 1) | 3-cyclopropyl-1,3-dihydro-2-benzofuran-5-ol (Intermediate 36 enantiomer 1) | LC/MS: QC_3_MIN: Rt = 2.109 min; m/z 395 [M + H]+, 811 [2M + Na]+. | $^1$H-NMR (400 MHz, DMSO-d$_6$): δ ppm 8.68-8.73 (m, 3H), 7.35 (d, 1H), 7.19-7.23 (m, 1H), 7.15 (dd, 1H), 5.01-5.08 (m, 1H), 4.90-4.96 (m, 1H), 4.53-4.58 (m, 1H), 1.73-1.84 (m, 1H), 1.61-1.72 (m, 1H), 1.40 (s, 3H), 1.02-1.12 (m, 1H), 0.87 (t, 3H), 0.44-0.58 (m, 3H), 0.32-0.39 (m, 1H). |
| 26 | 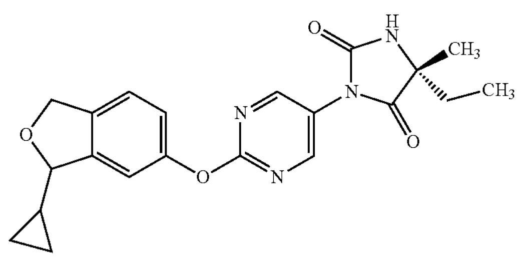 [SMILES: CC[C@@]1(C)NC(=O)N(c2cnc(Oc3ccc4c(c3)C(C3CC3)OC4)nc2)C1=O] | (5R)-3-[2-[(3-cyclopropyl-1,3-dihydroisobenzofuran-5-yl)oxy]pyrimidin-5-yl]-5-ethyl-5-methyl-imidazolidine-2,4-dione (diastereoisomer 2) | 3-cyclopropyl-1,3-dihydro-2-benzofuran-5-ol (Intermediate 37 enantiomer 2) | LC/MS: QC_3_MIN: Rt = 2.054 min; m/z 395 [M + H]+. | $^1$H-NMR (400 MHz, DMSO-d$_6$): δ ppm 8.68-8.73 (m, 3H), 7.35 (d, 1H), 7.19-7.23 (m, 1H), 7.15 (dd, 1H), 5.01-5.08 (m, 1H), 4.90-4.96 (m, 1H), 4.53-4.58 (m, 1H), 1.73-1.84 (m, 1H), 1.61-1.72 (m, 1H), 1.40 (s, 3H), 1.02-1.12 (m, 1H), 0.87 (t, 3H), 0.44-0.58 (m, 3H), 0.32-0.39 (m, 1H). |
| 27 | 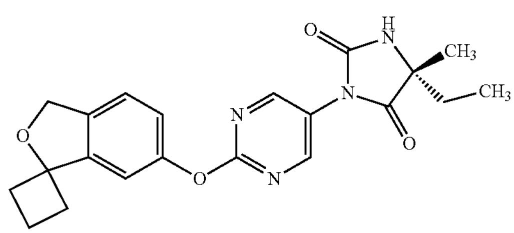 [SMILES: CC[C@@]1(C)NC(=O)N(c2cnc(Oc3ccc4c(c3)C3(CCC3)OC4)nc2)C1=O] | (5R)-5-ethyl-5-methyl-3-(2-spiro[1H-isobenzofuran-3,1'-cyclobutane]-5-yloxypyrimidin-5-yl)imidazolidine-2,4-dione | 3H-spiro[2-benzofuran-1,1'-cyclobutan]-6-ol (Intermediate 24) | LC/MS: QC_3_MIN: Rt = 1.905 min; m/z 395 [M + H]+, 811 [2M + Na]+. | $^1$H-NMR (400 MHz, DMSO-d$_6$): δ ppm 8.68-8.73 (m, 3H), 7.45 (d, 1H), 7.31 (d, 1H), 7.15 (dd, 1H), 4.97 (s, 2H), 2.42-2.52 (m, 2H), 2.28-2.38 (m, 2H), 1.61-1.98 (m, 4H), 1.40 (s, 3H), 0.87 (t, 3H). |
| 28 | 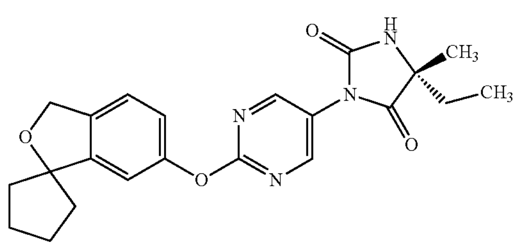 [SMILES: CC[C@@]1(C)NC(=O)N(c2cnc(Oc3ccc4c(c3)C3(CCCC3)OC4)nc2)C1=O] | (5R)-5-ethyl-5-methyl-3-(2-spiro[1H-isobenzofuran-3,1'-cyclopentane]-5-yloxypyrimidin-5-yl)imidazolidine-2,4-dione | 3H-spiro[2-benzofuran-1,1'-cyclopentan]-6-ol (Intermediate 25) | LC/MS: QC_3_MIN: Rt = 1.957 min; m/z 409 [M + H]+, 839 [2M + Na]+. | $^1$H-NMR (400 MHz, DMSO-d$_6$): δ ppm 8.68-8.73 (m, 3H), 7.31 (d, 1H), 7.18 (d, 1H), 7.12 (dd, 1H), 4.93 (s, 2H), 1.61-1.99 (m, 10H), 1.40 (s, 3H), 0.87 (t, 3H). |

| Ex. | Structure | Name | Phenol | LCMS | NMR |
|---|---|---|---|---|---|
| 29 | 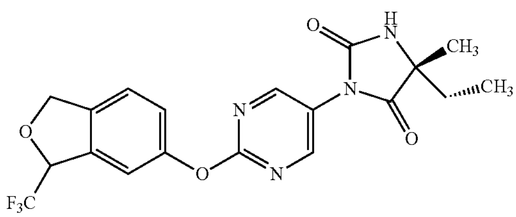 | (5R)-5-ethyl-5-methyl-3-[2-[[3-(trifluoromethyl)-1,3-dihydroisobenzofuran-5-yl]oxy]pyrimidin-5-yl]imidazolidine-2,4-dione (diastereoisomer 1) | 3-(trifluoromethyl)-1,3-dihydroisobenzofuran-5-ol (Intermediate 28 enantiomer 1) | LC/MS: QC_3_MIN: Rt = 2.280 min; m/z 423 [M + H]+. | $^1$H-NMR (400 MHz, DMSO-d$_6$): δ ppm 8.68-8.73 (m, 3H), 7.51 (d, 1H), 7.37 (dd, 1H), 7.30-7.33 (m, 1H), 5.82-5.90 (m, 1H), 5.16-5.26 (m, 2H), 1.73-1.84 (m, 1H), 1.61-1.72 (m, 1H), 1.40 (s, 3H), 0.87 (t, 3H). |
| 30 | 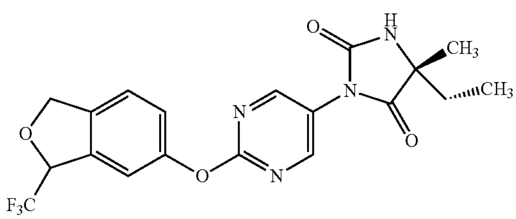 | (5R)-5-ethyl-5-methyl-3-[2-[[3-(trifluoromethyl)-1,3-dihydroisobenzofuran-5-yl]oxy]pyrimidin-5-yl]imidazolidine-2,4-dione (diastereoisomer 2) | 3-(trifluoromethyl)-1,3-dihydroisobenzofuran-5-ol (Intermediate 29 enantiomer 2) | LC/MS: QC_3_MIN: Rt = 2.266 min; m/z 423 [M + H]+. | $^1$H-NMR (400 MHz, DMSO-d$_6$): δ ppm 8.68-8.73 (m, 3H), 7.51 (d, 1H), 7.37 (dd, 1H), 7.30-7.33 (m, 1H), 5.82-5.90 (m, 1H), 5.16-5.26 (m, 2H), 1.73-1.84 (m, 1H), 1.61-1.72 (m, 1H), 1.40 (s, 3H), 0.87 (t, 3H). |
| 31 | 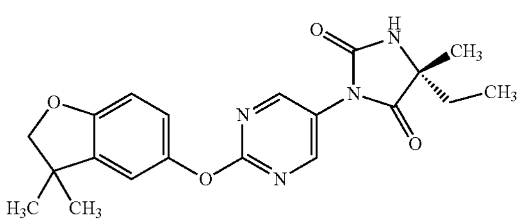 | (5R)-3-[2-[(3,3-dimethyl-2H-benzofuran-5-yl)oxy]pyrimidin-5-yl]-5-ethyl-5-methyl-imidazolidine-2,4-dione | 3,3-dimethyl-2H-benzofuran-5-ol (Intermediate 44) | LC/MS: QC_3_MIN: Rt = 2.258 min; m/z 383 [M + H]+. | $^1$H-NMR (400 MHz, DMSO-d$_6$): δ ppm 8.67-8.72 (m, 3H), 7.11 (d, 1H), 6.95 (dd, 1H), 6.79 (d, 1H), 4.25 (s, 2H), 1.73-1.83 (m, 1H), 1.61-1.71 (m, 1H), 1.40 (s, 3H), 1.30 (s, 6H), 0.87 (t, 3H). |
| 32 | 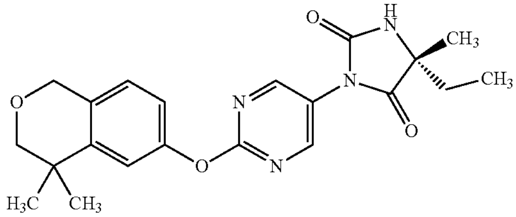 [SMILES: CC[C@@]1(C)NC(=O)N(c2cnc(Oc3ccc4c(c3)C(C)(C)COC4)nc2)C1=O] | (5R)-3-[2-(4,4-dimethylisochroman-6-yl)oxypyrimidin-5-yl]-5-ethyl-5-methyl-imidazolidine-2,4-dione N200001-65-1 | 4,4-dimethyl-3,4-dihydro-1H-isochromen-6-ol (Intermediate 42) | LC/MS: QC_3_MIN: Rt = 2.247 min; m/z 397 [M + H]+. | $^1$H-NMR (400 MHz, DMSO-d$_6$): δ ppm 8.68-8.74 (m, 3H), 7.28 (d, 1H), 7.07 (d, 1H), 7.01 (dd, 1H), 4.73 (s, 2H), 3.55 (s, 1H), 1.72-1.83 (m, 1H), 1.61-1.72 (m, 1H), 1.40 (s, 3H), 1.20 (s, 6H), 0.87 (t, 3H). |

Example 33

(5R)-3-[6-[(3,3-dimethyl-1H-isobenzofuran-5-yl)oxy]-3-pyridyl]-5-ethyl-5-methyl-imidazolidine-2,4-dione

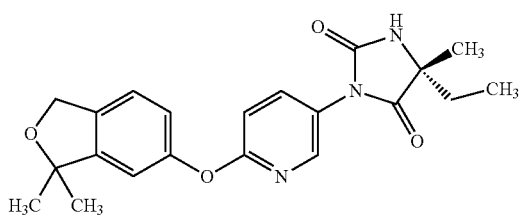 [SMILES: CC[C@@]1(C)NC(=O)N(c2ccc(Oc3ccc4c(c3)C(C)(C)OC4)nc2)C1=O]

To a solution of 3,3-dimethyl-1H-isobenzofuran-5-ol (Intermediate 18, 45 mg, 0.2741 mmol) in DMF (1 ml) (5R)-5-ethyl-3-(6-fluoro-3-pyridyl)-5-methyl-imidazolidine-2,4-dione (Intermediate 4, 45.51 mg, 0.1918 mmol) and dipotassium carbonate (75.755 mg, 0.5481 mmol) were added. The reaction mixture was stirred at 100° C. for 12 hours. The reaction was quenched with an aqueous saturated solution of ammonium chloride (5 ml) and extracted with ethyl acetate (10 ml). The organic layer was washed with brine (3×10 ml) dried over sodium sulphate and concentrated under vacuum. The residue was purified by flash chromatography on silica gel (Biotage system) using a SNAP 10 g as column and cyclohexane/ethyl acetate from 75:25 to 30:70 as eluent to afford the title compound (25 mg).

LC/MS: QC_3_MIN: Rt=1.857 min; m/z 382 [M+H]+.

$^1$H-NMR (400 MHz, DMSO-d$_6$): δ ppm 8.58 (s, 1H), 7.85 (dd, 1H), 7.29 (d, 1H), 7.09-7.15 (m, 2H), 7.04 (dd, 1H), 4.96 (s, 2H), 1.72-1.83 (m, 1H), 1.59-1.70 (m, 1H), 1.42 (s, 6H), 1.39 (s, 3H), 0.86 (t, 3H).

The following compounds were prepared using the foregoing methodology, replacing 3,3-dimethyl-1H-isobenzofuran-5-ol (Intermediate 18) with the appropriate phenol. Final products were purified by flash-chromatography (Silica cartridge using cyclohexane/EtOAc as eluents or reverse phase C18 column using water/acetonitrile as eluents).

| Ex. | Structure | Name | Phenol | LCMS | NMR |
|---|---|---|---|---|---|
| 34 | 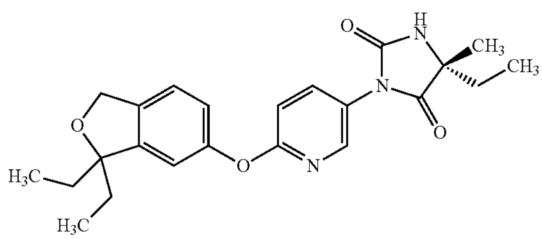 [SMILES: CCC1(CC)OCc2ccc(Oc3ccc(N4C(=O)N[C@](C)(CC)C4=O)cn3)cc21] | (5R)-3-[6-[(3,3-diethyl-1H-isobenzofuran-5-yl)oxy]-3-pyridyl]-5-ethyl-5-methyl-imidazolidine-2,4-dione | 3,3-diethyl-1,3-dihydro-2-benzofuran-5-ol (Intermediate 19) | LC/MS: QC_3_MIN: Rt = 2.495 min; m/z 410 [M + H]+. | $^1$H-NMR (400 MHz, DMSO-d$_6$): δ ppm 8.58 (s, 1H), 8.13 (d, 1H), 7.85 (dd, 1H), 7.30 (d, 1H), 7.09 (d, 1H), 7.06 (dd, 1H), 7.00 (d, 1H), 5.00 (s, 2H), 1.59-1.82 (m, 6H), 1.39 (s, 3H), 0.86 (t, 3H), 0.69 (t, 6H). |
| 35 | 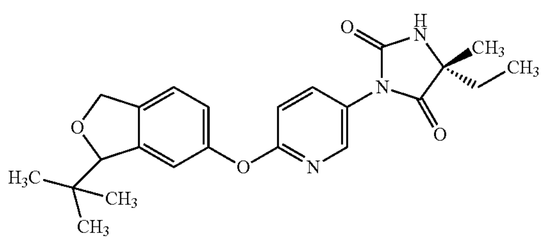 [SMILES: CC[C@@]1(C)NC(=O)N(c2ccc(Oc3ccc4c(c3)C(C(C)(C)C)OC4)nc2)C1=O] | (5R)-3-[6-[(3-tert-butyl-1,3-dihydroisobenzofuran-5-yl)oxy]-3-pyridyl]-5-ethyl-5-methyl-imidazolidine-2,4-dione (diastereoisomer 1) | 3-tert-butyl-1,3-dihydro-2-benzofuran-5-ol (Intermediate 30 enantiomer 1) | LC/MS: QC_3_MIN: Rt = 2.028 min; m/z 410 [M + H]+. | $^1$H-NMR (400 MHz, DMSO-d$_6$): δ ppm 8.58 (s, 1H), 8.13 (d, 1H), 7.85 (dd, 1H), 7.34 (d, 1H), 7.06-7.15 (m, 3H), 5.02-5.09 (m, 1H), 4.93-4.99 (m, 1H), 4.82-4.86 (m, 1H), 1.72-1.83 (m, 1H), 1.60-1.70 (m, 1H), 1.39 (s, 3H), 0.91 (s, 9H), 0.86 (t, 3H). |
| 36 | 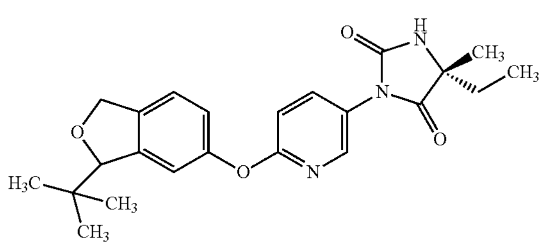 [SMILES: CC[C@@]1(C)NC(=O)N(c2ccc(Oc3ccc4c(c3)C(C(C)(C)C)OC4)nc2)C1=O] | (5R)-3-[6-[(3-tert-butyl-1,3-dihydroisobenzofuran-5-yl)oxy]-3-pyridyl]-5-ethyl-5-methyl-imidazolidine-2,4-dione (diastereoisomer 2) | 3-tert-butyl-1,3-dihydro-2-benzofuran-5-ol (Intermediate 31 enantiomer 2) | LC/MS: QC_3_MIN: Rt = 2.107 min; m/z 410 [M + H]+. | $^1$H-NMR (400 MHz, DMSO-d$_6$): δ ppm 8.58 (s, 1H), 8.13 (d, 1H), 7.85 (dd, 1H), 7.34 (d, 1H), 7.06-7.15 (m, 3H), 5.02-5.09 (m, 1H), 4.93-4.99 (m, 1H), 4.82-4.86 (m, 1H), 1.72-1.83 (m, 1H), 1.60-1.70 (m, 1H), 1.39 (s, 3H), 0.91 (s, 9H), 0.86 (t, 3H). |

-continued

| Ex. | Structure | Name | Phenol | LCMS | NMR |
|---|---|---|---|---|---|
| 37 | 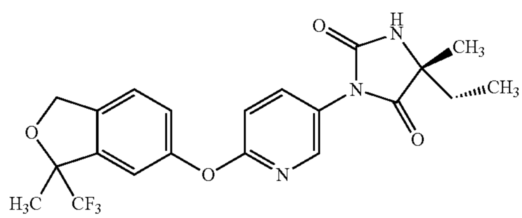 | (5R)-5-ethyl-5-methyl-3-[6-[[3-methyl-3-(trifluoro-methyl)-1H-isobenzofuran-5-yl]oxy]-3-pyridyl]imidazolidine-2,4-dione (diastereoisomer 1) | 3-methyl-3-(trifluoro-methyl)-1,3-dihydro-2-benzofuran-5-ol (Intermediate 32 enantiomer 1) | LC/MS: QC_3_MIN: Rt = 2.450 min; m/z 436 [M + H]+. | ¹H-NMR (400 MHz, DMSO-d₆): δ ppm 8.58 (br.s, 1H), 8.14 (d, 1H), 7.88 (dd, 1H), 7.45 (d, 1H), 7.24-7.30 (m, 2H), 7.18 (d, 1H), 5.11-5.22 (m, 2H), 1.72-1.83 (m, 1H), 1.60-1.71 (m, 4H), 1.39 (s, 3H), 0.86 (t, 3H). |
| 38 | 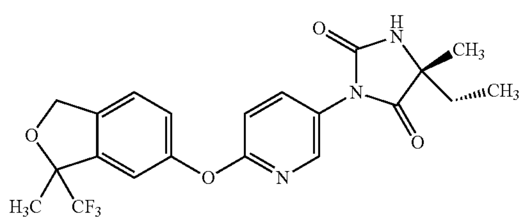 | (5R)-5-ethyl-5-methyl-3-[6-[[3-methyl-3-(trifluoro-methyl)-1H-isobenzofuran-5-yl]oxy]-3-pyridyl]imidazolidine-2,4-dione (diastereoisomer 2) | 3-methyl-3-(trifluoro-methyl)-1,3-dihydro-2-benzofuran-5-ol (Intermediate 33 enantiomer 2) | LC/MS: QC_3_MIN: Rt = 2.429 min; m/z 436 [M + H]+. | ¹H-NMR (400 MHz, DMSO-d₆): δ ppm 8.58 (br.s, 1H), 8.14 (d, 1H), 7.88 (dd, 1H), 7.45 (d, 1H), 7.24-7.30 (m, 2H), 7.18 (d, 1H), 5.11-5.22 (m, 2H), 1.72-1.83 (m, 1H), 1.60-1.71 (m, 4H), 1.39 (s, 3H), 0.86 (t, 3H). |
| 39 | 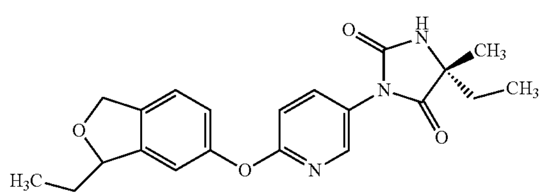 [SMILES: CCC1OCc2ccc(Oc3ccc(N4C(=O)N[C@](C)(CC)C4=O)cn3)cc21] | (5R)-5-ethyl-3-[6-[(3-ethyl-1,3-dihydroiso-benzofuran-5-yl)oxy]-3-pyridyl]-5-methyl-imidazolidine-2,4-dione (diastereoisomer 1) | 3-ethyl-1,3-dihydro-2-benzofuran-5-ol (Intermediate 34 enantiomer 1) | LC/MS: QC_3_MIN: Rt = 1.863 min; m/z 382 [M + H]+. | ¹H-NMR (400 MHz, DMSO-d₆): δ ppm 8.58 (s, 1H), 8.13 (d, 1H), 7.85 (dd, 1H), 7.33 (d, 1H), 7.13 (d, 1H), 7.04-7.09 (m, 2H), 5.08-5.14 (m, 1H), 4.92-5.05 (m, 2H), 1.59-1.91 (m, 4H), 1.39 (s, 3H), 0.82-0.92 (m, 6H). |
| 40 | 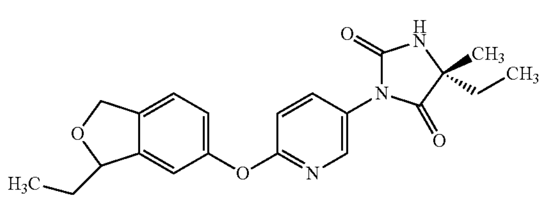 [SMILES: CCC1OCc2ccc(Oc3ccc(N4C(=O)N[C@](C)(CC)C4=O)cn3)cc21] | (5R)-5-ethyl-3-[6-[(3-ethyl-1,3-dihydroiso-benzofuran-5-yl)oxy]-3-pyridyl]-5-methyl-imidazolidine-2,4-dione (diastereoisomer 2) | 3-ethyl-1,3-dihydro-2-benzofuran-5-ol (Intermediate 35 enantiomer 2) | LC/MS: QC_3_MIN: Rt = 1.959 min; m/z 382 [M + H]+. | ¹H-NMR (400 MHz, DMSO-d₆): δ ppm 8.58 (s, 1H), 8.13 (d, 1H), 7.85 (dd, 1H), 7.33 (d, 1H), 7.13 (d, 1H), 7.04-7.09 (m, 2H), 5.08-5.14 (m, 1H), 4.92-5.05 (m, 2H), 1.59-1.91 (m, 4H), 1.39 (s, 3H), 0.82-0.92 (m, 6H). |

| Ex. | Structure | Name | Phenol | LCMS | NMR |
| --- | --- | --- | --- | --- | --- |
| 41 | 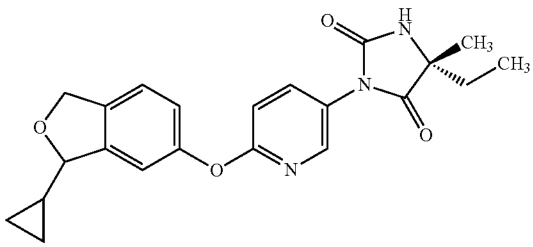 [SMILES: CC[C@@]1(C)NC(=O)N(c2ccc(Oc3ccc4c(c3)C(C3CC3)OC4)nc2)C1=O] | (5R)-3-[6-[(3-cyclopropyl-1,3-dihydroiso-benzofuran-5-yl)oxy]-3-pyridyl]-5-ethyl-5-methyl-imidazolidine-2,4-dione (diastereoisomer 1) | 3-cyclopropyl-1,3-dihydro-2-benzofuran-5-ol (Intermediate 36 enantiomer 1) | LC/MS: QC_3_MIN: Rt = 2.162 min; m/z 394 [M + H]+. | ¹H-NMR (400 MHz, DMSO-d₆): δ ppm 8.58 (s, 1H), 8.13 (d, 1H), 7.85 (dd, 1H), 7.34 (d, 1H), 7.14 (d, 1H), 7.06-7.13 (m, 2H), 5.00-5.07 (m, 1H), 4.89-4.95 (m, 1H), 4.52-4.58 (m, 1H), 1.72-1.83 (m, 1H), 1.59-1.70 (m, 1H), 1.39 (s, 3H), 1.01-1.11 (m, 1H), 0.86 (t, 3H), 0.43-0.58 (m, 3H), 0.31-0.38 (m, 1H). |
| 42 | 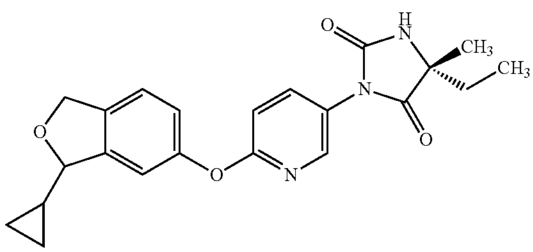 [SMILES: CC[C@@]1(C)NC(=O)N(c2ccc(Oc3ccc4c(c3)C(C3CC3)OC4)nc2)C1=O] | (5R)-3-[6-[(3-cyclopropyl-1,3-dihydroiso-benzofuran-5-yl]oxy]-3-pyridyl]-5-ethyl-5-methyl-imidazolidine-2,4-dione (diastereoisomer 2) | 3-cyclopropyl-1,3-dihydro-2-benzofuran-5-ol (Intermediate 37 enantiomer 2) | LC/MS: QC_3_MIN: Rt = 2.215 min; m/z 394 [M + H]+. | ¹H-NMR (400 MHz, DMSO-d₆): δ ppm 8.58 (s, 1H), 8.13 (d, 1H), 7.85 (dd, 1H), 7.34 (d, 1H), 7.14 (d, 1H), 7.06-7.13 (m, 2H), 5.00-5.07 (m, 1H), 4.89-4.95 (m, 1H), 4.52-4.58 (m, 1H), 1.72-1.83 (m, 1H), 1.59-1.70 (m, 1H), 1.39 (s, 3H), 1.01-1.11 (m, 1H), 0.86 (t, 3H), 0.43-0.58 (m, 3H), 0.31-0.38 (m, 1H). |
| 43 | 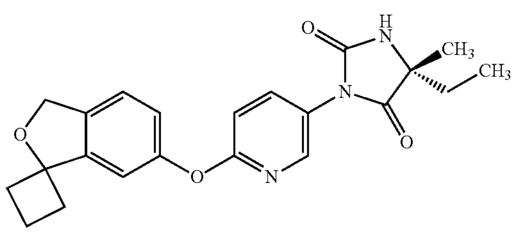 [SMILES: CC[C@@]1(C)NC(=O)N(c2ccc(Oc3ccc4c(c3)C3(CCC3)OC4)nc2)C1=O] | (5R)-5-ethyl-5-methyl-3-(6-spiro[1H-isobenzofuran-3,1'-cyclobutane]-5-yloxy-3-pyridyl] imidazolidine-2,4-dione | 3H-spiro[2-benzofuran-1,1'-cyclobutan]-6-ol (Intermediate 24) | LC/MS: QC_3_MIN: Rt = 1.963 min; m/z 394 [M + H]+, 809 [2M + Na]+. | ¹H-NMR (400 MHz, DMSO-d₆): δ ppm 8.58 (s, 1H), 8.13 (d, 1H), 7.85 (dd, 1H), 7.36 (d, 1H), 7.29 (d, 1H), 7.14 (d, 1H), 7.07 (dd, 1H), 4.96 (s, 2H), 2.42-2.52 (m, 2H), 2.28-2.38 (m, 2H), 1.61-1.93 (m, 4H), 1.39 (s, 3H), 0.86 (t, 3H). |
| 44 | 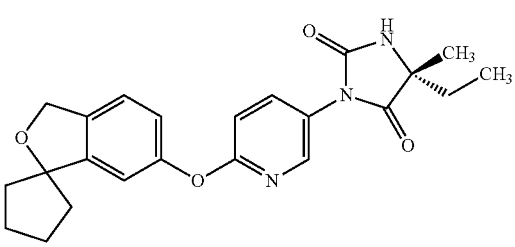 [SMILES: CC[C@@]1(C)NC(=O)N(c2ccc(Oc3ccc4c(c3)C3(CCCC3)OC4)nc2)C1=O] | (5R)-5-ethyl-5-methyl-3-(6-spiro[1H-isobenzofuran-3,1'-cyclopentane]-5-yloxy-3-pyridyl) imidazolidine-2,4-dione | 3H-spiro[2-benzofuran-1,1'-cyclopentan]-6-ol (Intermediate 25) | LC/MS: QC_3_MIN: Rt = 1.997 min; m/z 408 [M + H]+, 837 [2M + Na]+. | ¹H-NMR (400 MHz, DMSO-d₆): δ ppm 8.58 (s, 1H), 8.13 (d, 1H), 7.85 (dd, 1H), 7.29 (d, 1H), 7.12 (d, 1H), 7.09 (d, 1H), 7.04 (dd, 1H), 4.93 (s, 2H), 1.60-1.97 (m, 10H), 1.39 (s, 3H), 0.85 (t, 3H). |

| Ex. | Structure | Name | Phenol | LCMS | NMR |
|---|---|---|---|---|---|
| 45 | 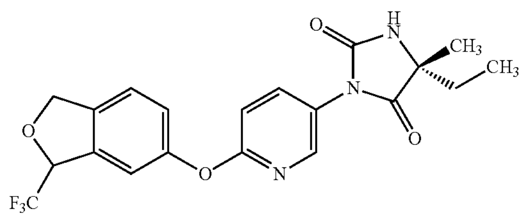 [SMILES: CC[C@@]1(C)NC(=O)N(c2ccc(Oc3ccc4c(c3)C(C(F)(F)F)OC4)nc2)C1=O] | (5R)-5-ethyl-5-methyl-3-[6-[[3-(trifluoromethyl)-1,3-dihydroisobenzofuran-5-yl]oxy]-3-pyridyl]imidazolidine-2,4-dione (diastereoisomer 1) | 3-(trifluoromethyl)-1,3-dihydroisobenzofuran-5-ol (Intermediate 28 enantiomer 1) | LC/MS: QC_3_MIN: Rt = 2.381 min; m/z 422 [M + H]+. | $^1$H-NMR (400 MHz, DMSO-d$_6$): δ ppm 8.58 (s, 1H), 8.14 (d, 1H), 7.88 (dd, 1H), 7.48 (d, 1H), 7.27 (dd, 1H), 7.17-7.22 (m, 2H), 5.81-5.89 (m, 1H), 5.13-5.24 (m, 2H), 1.72-1.83 (m, 1H), 1.60-1.71 (m, 1H), 1.39 (s, 3H), 0.86 (t, 3H). |
| 46 | 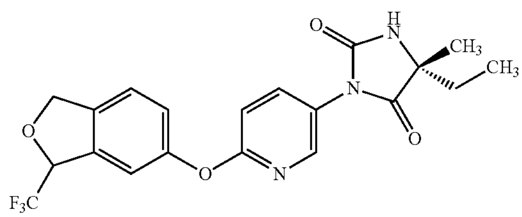 [SMILES: CC[C@@]1(C)NC(=O)N(c2ccc(Oc3ccc4c(c3)C(C(F)(F)F)OC4)nc2)C1=O] | (5R)-5-ethyl-5-methyl-3-[6-[[3-(trifluoromethyl)-1,3-dihydroisobenzofuran-5-yl]oxy]-3-pyridyl]imidazolidine-2,4-dione (diastereoisomer 2) | 3-(trifluoromethyl)-1,3-dihydroiso benzofuran-5-ol (Intermediate 29 enantiomer 2) | LC/MS: QC_3_MIN: Rt = 2.416 min; m/z 422 [M + H]+. | $^1$H-NMR (400 MHz, DMSO-d$_6$): δ ppm 8.58 (s, 1H), 8.14 (d, 1H), 7.88 (dd, 1H), 7.48 (d, 1H), 7.27 (dd, 1H), 7.17-7.22 (m, 2H), 5.81-5.89 (m, 1H), 5.13-5.24 (m, 2H), 1.72-1.83 (m, 1H), 1.60-1.71 (m, 1H), 1.39 (s, 3H), 0.86 (t, 3H). |
| 47 | 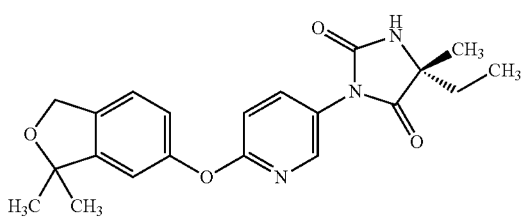 [SMILES: CC[C@@]1(C)NC(=O)N(c2ccc(Oc3ccc4c(c3)C(C)(C)OC4)nc2)C1=O] | (5R)-3-[6-[(3,3-dimethyl-2H-benzofuran-5-yl)oxy]-3-pyridyl]-5-ethyl-5-methyl-imidazolidine-2,4-dione | 3,3-dimethyl-2H-benzofuran-5-ol (Intermediate 44) | LC/MS: QC_3_MIN: Rt = 2.321 min; m/z 382 [M + H]+, 785 [2M + Na]+. | $^1$H-NMR (400 MHz, DMSO-d$_6$): δ ppm 8.56 (br.s, 1H), 8.11 (d, 1H), 7.81 (dd, 1H), 7.02-7.07 (m, 2H), 6.88 (dd, 1H), 6.78 (d, 1H), 4.25 (s, 2H), 1.72-1.83 (m, 1H), 1.59-1.70 (m, 1H), 1.39 (s, 3H), 1.29 (s, 6H), 0.86 (t, 3H). |
| 48 | 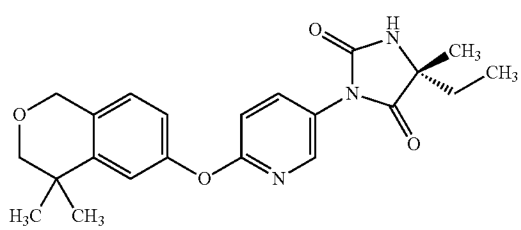 [SMILES: CC[C@@]1(C)NC(=O)N(c2ccc(Oc3ccc4c(c3)C(C)(C)COC4)nc2)C1=O] | (5R)-3-[6-(4,4-dimethylisochroman-6-yl)oxy-3-pyridyl]-5-ethyl-5-methyl-imidazolidine-2,4-dione | 4,4-dimethyl-3,4-dihydro-1H-isochromen-6-ol (Intermediate 42) | LC/MS: QC_3_MIN: Rt = 1.954 min; m/z 396 [M + H]+. | $^1$H-NMR (400 MHz, DMSO-d$_6$): δ ppm 8.59 (br.s, 1H), 8.12 (d, 1H), 7.84 (dd, 1H), 7.20 (d, 1H), 7.10 (d, 1H), 7.06 (d, 1H), 6.94 (dd, 1H), 4.73 (s, 2H), 3.56 (s, 2H), 1.72-1.83 (m, 1H), 1.61-1.72 (m, 1H), 1.39 (s, 3H), 1.21 (s, 6H), 0.86 (t, 3H). |

Example 49

3-[6-[(3,3-diethyl-1H-isobenzofuran-5-yl)oxy]-3-pyridyl]-5,5-dimethyl-imidazolidine-2,4-dione

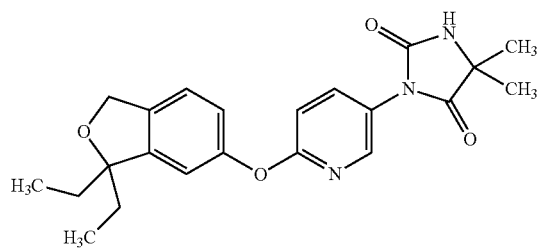

To a solution of 3,3-diethyl-1H-isobenzofuran-5-ol (Intermediate 19, 20 mg, 0.1040 mmol) in DMF (1 ml) 3-(6-fluoro-3-pyridyl)-5,5-dimethyl-imidazolidine-2,4-dione (Intermediate 3, 23.22 mg, 0.1040 mmol) and dipotassium carbonate (28.756 mg, 0.2081 mmol) were added. The reaction mixture was stirred at 100° C. for 12 hours. The reaction was quenched with an aqueous saturated solution of ammonium chloride (5 ml) and extracted with ethyl acetate 10 ml. The organic layer was washed with brine (3×10 ml) dried over sodium sulphate and concentrated under vacuum. The residue was purified by flash chromatography on silica gel (Biotage system) using a SNAP 10 g as column and cyclohexane/ethyl acetate from 85:15 to 20:80 as eluent to afford the title compound (19 mg) as white solid.

LC/MS: QC_3_MIN: Rt=2.405 min; m/z 396 [M+H]+.

$^1$H-NMR (400 MHz, DMSO-$d_6$): δ ppm 8.61 (s, 1H), 8.15 (d, 1H), 7.87 (dd, 1H), 7.30 (d, 1H), 7.10 (d, 1H), 7.05 (dd, 1H), 7.00 (d, 1H), 5.00 (s, 2H), 1.74 (q, 4H), 1.41 (s, 6H), 0.69 (t, 6H).

The following compounds were prepared using the foregoing methodology, replacing 3,3-diethyl-1H-isobenzofuran-5-ol (Intermediate 19) with the appropriate phenol. Final products were purified by flash-chromatography (Silica cartridge using cyclohexane/EtOAc as eluents or reverse phase C18 column using water/acetonitrile as eluents).

| Ex. | Structure | Name | Phenol | LCMS | NMR |
|---|---|---|---|---|---|
| 50 | 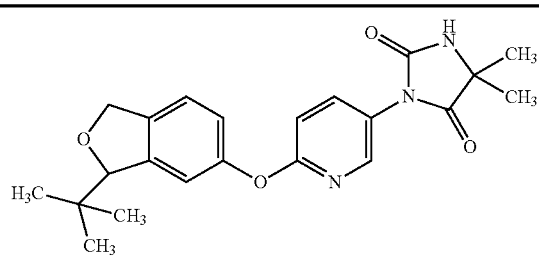 | 3-[6-[(3-tert-butyl-1,3-dihydroisobenzofuran-5-yl)oxy]-3-pyridyl]-5,5-dimethyl-imidazolidine-2,4-dione (enantiomer 1) | 3-tert-butyl-1,3-dihydro-2-benzofuran-5-ol (Intermediate 30 enantiomer 1) | LC/MS: QC_3_MIN: Rt = 2.054 min; m/z 396 [M + H]+. | $^1$H-NMR (400 MHz, DMSO-$d_6$): δ ppm 8.61 (s, 1H), 8.15 (d, 1H), 7.88 (dd, 1H), 7.34 (d, 1H), 7.05-7.15 (m, 3H), 5.02-5.09 (m, 1H), 4.93-4.99 (m, 1H), 4.93-4.97 (m, 1H), 1.40 (s, 6H), 0.90 (s, 9H). |
| 51 | 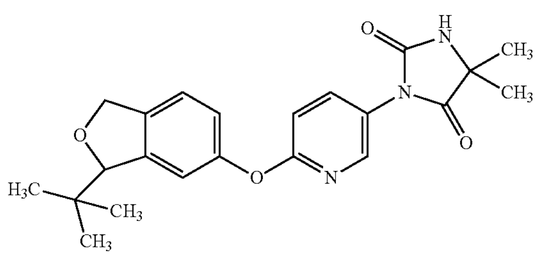 [SMILES: CC1(C)NC(=O)N(c2ccc(Oc3ccc4c(c3)C(C(C)(C)C)OC4)nc2)C1=O] | 3-[6-[(3-tert-butyl-1,3-dihydroisobenzofuran-5-yl)oxy]-3-pyridyl]-5,5-dimethyl-imidazolidine-2,4-dione (enantiomer 2) | 3-tert-butyl-1,3-dihydro-2-benzofuran-5-ol (Intermediate 31 enantiomer 2) | LC/MS: QC_3_MIN: Rt = 2.147 min; m/z 396 [M + H]+, 813 [2M + Na]+. | $^1$H-NMR(400 MHz, DMSO-$d_6$): δ ppm 8.61 (s, 1H), 8.15 (d, 1H), 7.88 (dd, 1H), 7.34 (d, 1H), 7.05-7.15 (m, 3H), 5.02-5.09 (m, 1H), 4.93-4.99 (m, 1H), 4.93-4.97 (m, 1H), 1.40 (s, 6H), 0.90 (s, 9H). |
| 52 | 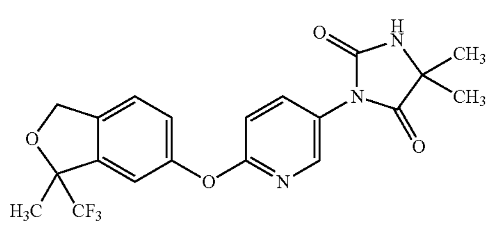 [SMILES: CC1(C)NC(=O)N(c2ccc(Oc3ccc4c(c3)C(C)(C(F)(F)F)OC4)nc2)C1=O] | 5,5-dimethyl-3-[6-[[3-methyl-3-(trifluoromethyl)-1H-isobenzofuran-5-yl]oxy]-3-pyridyl] imidazolidine-2,4-dione (enantiomer 1) | 3-methyl-3-(trifluoromethyl)-1,3-dihydro-2-benzofuran-5-ol (Intermediate 32 enantiomer i) | LC/MS: QC_3_MIN: Rt = 2.388 min; m/z 422 [M + H]+. | $^1$H-NMR (400 MHz, DMSO-$d_6$): δ ppm 8.62 (br.s, 1H), 8.16 (d, 1H), 7.91 (dd, 1H), 7.45 (d, 1H), 7.23-7.29 (m, 2H), 7.18 (d, 1H), 5.11-5.22 (m, 2H), 1.65 (s, 3H), 1.40 (s, 6H). |
| 53 | 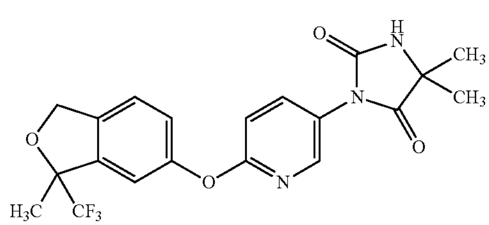 [SMILES: CC1(C)NC(=O)N(c2ccc(Oc3ccc4c(c3)C(C)(C(F)(F)F)OC4)nc2)C1=O] | 5,5-dimethyl-3-[6-[[3-methyl-3-(trifluoromethyl)-1H-isobenzofuran-5-yl]oxy]-3-pyridyl] imidazolidine-2,4-dione (enantiomer 2) | 3-methyl-3-(trifluoromethyl)-1,3-dihydro-2-benzofuran-5-ol (Intermediate 33 enantiomer 2) | LC/MS: QC_3_MIN: Rt = 2.378 min; m/z 422 [M + H]+. | $^1$H-NMR (400 MHz, DMSO-$d_6$): δ ppm 8.62 (br.s, 1H), 8.16 (d, 1H), 7.91 (dd, 1H), 7.45 (d, 1H), 7.23-7.29 (m, 2H), 7.18 (d, 1H), 5.11-5.22 (m, 2H), 1.65 (s, 3H), 1.40 (s, 6H). |

| Ex. | Structure | Name | Phenol | LCMS | NMR |
|---|---|---|---|---|---|
| 54 | 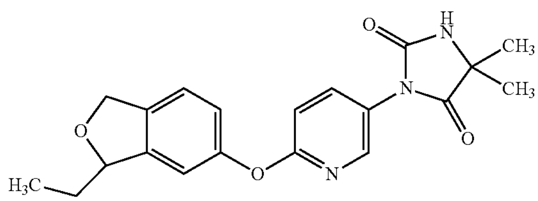 [SMILES: CCC1OCc2ccc(Oc3ccc(N4C(=O)NC(C)(C)C4=O)cn3)cc21] | 3-[6-[(3-ethyl-1,3-dihydroiso-benzofuran-5-yl)oxy]-3-pyridyl]-5,5-dimethyl-imidazolidine-2,4-dione (enantiomer 1) | 3-ethyl-1,3-dihydro-2-benzofuran-5-ol (Intermediate 34 enantiomer 1) | LC/MS: QC_3_MIN: Rt = 1.798 min; m/z 368 [M + H]+. | $^1$H-NMR (400 MHz, DMSO-d$_6$): δ ppm 8.62 (s, 1H), 8.14 (d, 1H), 7.87 (dd, 1H), 7.33 (d, 1H), 7.13 (d, 1H), 7.04-7.09 (m, 2H), 5.08-5.14 (m, 1H), 4.92-5.05 (m, 2H), 1.81-1.92 (m, 1H), 1.58-1.69 (m, 1H), 1.41 (s, 6H), 0.89 (t, 3H). |
| 55 | 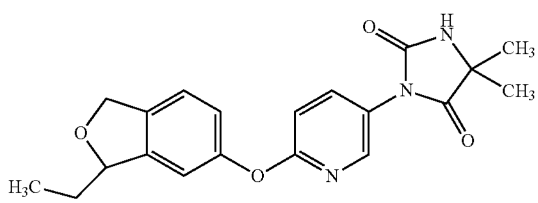 [SMILES: CCC1OCc2ccc(Oc3ccc(N4C(=O)NC(C)(C)C4=O)cn3)cc21] | 3-[6-[(3-ethyl-1,3-dihydroiso-benzofuran-5-yl)oxy]-3-pyridyl]-5,5-dimethyl-imidazolidine-2,4-dione (enantiomer 2) | 3-ethyl-1,3-dihydro-2-benzofuran-5-ol (Intermediate 35 enantiomer 2) | LC/MS: QC_3_MIN: Rt = 1.840 min; m/z 368 [M + H]+. | $^1$H-NMR (400 MHz, DMSO-d$_6$): δ ppm 8.62 (s, 1H), 8.14 (d, 1H), 7.87 (dd, 1H), 7.33 (d, 1H), 7.13 (d, 1H), 7.04-7.09 (m, 2H), 5.08-5.14 (m, 1H), 4.92-5.05 (m, 2H), 1.81-1.92 (m, 1H), 1.58-1.69 (m, 1H), 1.41 (s, 6H), 0.89 (t, 3H). |
| 56 | 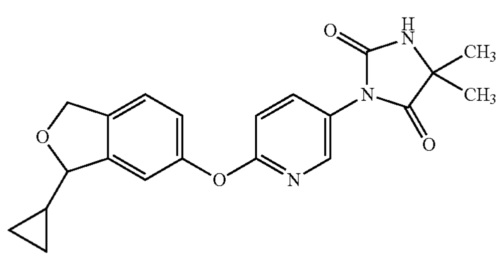 [SMILES: CC1(C)NC(=O)N(c2ccc(Oc3ccc4c(c3)C(C3CC3)OC4)nc2)C1=O] | 3-[6-[(3-cyclopropyl-1,3-dihydroiso-benzofuran-5-yl)oxy]-3-pyridyl]-5,5-dimethyl-imidazolidine-2,4-dione (enantiomer 1) | 3-cyclopropyl-1,3-dihydro-2-benzofuran-5-ol (Intermediate 36 enantiomer 1) | LC/MS: QC_3_MIN: Rt = 2.097 min; m/z 380 [M + H]+. | $^1$H-NMR (400 MHz, DMSO-d$_6$): δ ppm 8.62 (s, 1H), 8.15 (d, 1H), 7.88 (dd, 1H), 7.34 (d, 1H), 7.14 (d, 1H), 7.06-7.13 (m, 2H), 5.00-5.07 (m, 1H), 4.89-4.95 (m, 1H), 4.52-4.58 (m, 1H), 1.41 (s, 6H), 1.02-1.11 (m, 1H), 0.43-0.58 (m, 3H), 0.31-0.39 (m, 1H). |
| 57 | 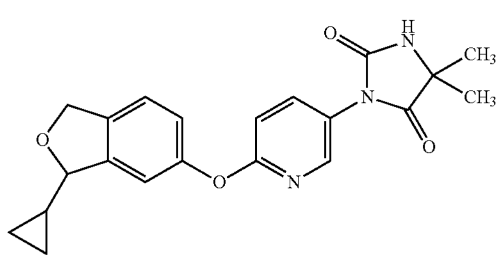 [SMILES: CC1(C)NC(=O)N(c2ccc(Oc3ccc4c(c3)C(C3CC3)OC4)nc2)C1=O] | 3-[6-[(3-cyclopropyl-1,3-dihydroiso-benzofuran-5-yl)oxy]-3-pyridyl]-5,5-dimethyl-imidazolidine-2,4-dione (enantiomer 2) | 3-cyclopropyl-1,3-dihydro-2-benzofuran-5-ol (Intermediate 37 enantiomer 2) | LC/MS: QC_3_MIN: Rt = 2.181 min; m/z 380 [M + H]+. | $^1$H-NMR (400 MHz, DMSO-d$_6$): δ ppm 8.62 (s, 1H), 8.15 (d, 1H), 7.88 (dd, 1H), 7.34 (d, 1H), 7.14 (d, 1H), 7.06-7.13 (m, 2H), 5.00-5.07 (m, 1H), 4.89-4.95 (m, 1H), 4.52-4.58 (m, 1H), 1.41 (s, 6H), 1.02-1.11 (m, 1H), 0.43-0.58 (m, 3H), 0.31-0.39 (m, 1H). |

-continued

| Ex. | Structure | Name | Phenol | LCMS | NMR |
|---|---|---|---|---|---|
| 58 | 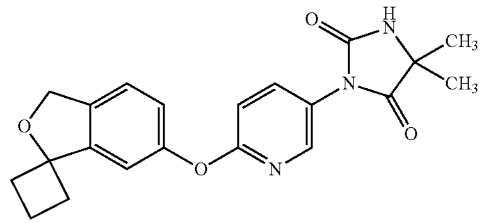 [SMILES: CC1(C)NC(=O)N(c2ccc(Oc3ccc4c(c3)C3(CCC3)OC4)nc2)C1=O] | 5,5-dimethyl-3-(6-spiro[1H-isobenzofuran-3,1'-cyclobutane]-5-yloxy-3-pyridyl]imidazolidine-2,4-dione | 3H-spiro[2-benzofuran-1,1'-cyclobutan]-6-ol (Intermediate 24) | LC/MS: QC_3_MIN: Rt = 1.888 min; m/z 380 [M + H]+, 781 [2M + Na]+. | $^1$H-NMR (400 MHz, DMSO-d$_6$): δ ppm 8.62 (s, 1H), 8.16 (d, 1H), 7.88 (dd, 1H), 7.36 (d, 1H), 7.29 (d, 1H), 7.15 (d, 1H), 7.06 (dd, 1H), 4.96 (s, 2H), 2.42-2.52 (m, 2H), 2.28-2.38 (m, 2H), 1.73-1.97 (m, 2H), 1.41 (s, 6H). |
| 59 | 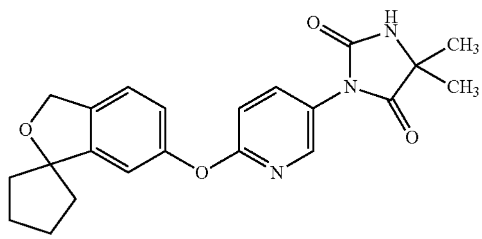 [SMILES: CC1(C)NC(=O)N(c2ccc(Oc3ccc4c(c3)C3(CCCC3)OC4)nc2)C1=O] | 5,5-dimethyl-3-(6-spiro[1H-isobenzofuran-3,1'-cyclopentane]-5-yloxy-3-pyridyl]imidazolidine-2,4-dione | 3H-spiro[2-benzofuran-1,1'-cyclopentan]-6-ol (Intermediate 25) | LC/MS: QC_3_MIN: Rt = 1.939 min; m/z 394 [M + H]+, 809 [2M + Na]+. | $^1$H-NMR (400 MHz, DMSO-d$_6$): δ ppm 8.61 (s, 1H), 8.14 (d, 1H), 7.87 (dd, 1H), 7.29 (d, 1H), 7.12 (d, 1H), 7.09 (d, 1H), 7.03 (dd, 1H), 4.92 (s, 2H), 1.72-1.97 (m, 8H), 1.40 (s, 6H). |
| 60 | 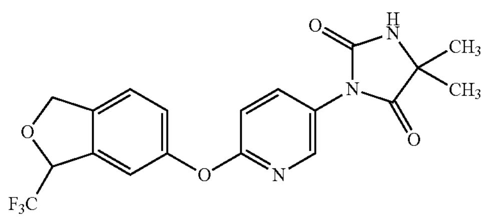 [SMILES: CC1(C)NC(=O)N(c2ccc(Oc3ccc4c(c3)C(C(F)(F)F)OC4)nc2)C1=O] | 5,5-dimethyl-3-[6-[[3-(trifluoro-methyl)-1,3-dihydroiso-benzofuran-5-yl]oxy]-3-pyridyl]imidazolidine-2,4-dione (enantiomer 1) | 3-(trifluoro-methyl)-1,3-dihydroiso-benzofuran-5-ol (Intermediate 28 enantiomer 1) | LC/MS: QC_3_MIN: Rt = 2.247 min; m/z 408 [M + H]+. | $^1$H-NMR (400 MHz, DMSO-d$_6$): δ ppm 8.62 (br.s, 1H), 8.15 (d, 1H), 7.91 (dd, 1H), 7.48 (d, 1H), 7.28 (dd, 1H), 7.17-7.22 (m, 2H), 5.81-5.89 (m, 1H), 5.12-5.25 (m, 2H), 1.41 (s, 6H). |
| 61 | 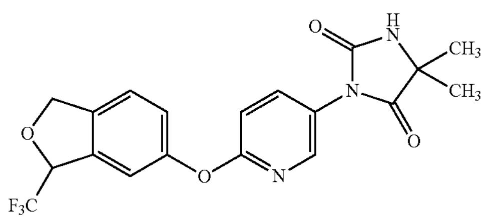 [SMILES: CC1(C)NC(=O)N(c2ccc(Oc3ccc4c(c3)C(C(F)(F)F)OC4)nc2)C1=O] | 5,5-dimethyl-3-[6-[[3-(trifluoro-methyl)-1,3-dihydroiso-benzofuran-5-yl]oxy]-3-pyridyl]imidazolidine-2,4-dione (enantiomer 2) | 3-(trifluoro-methyl)-1,3-dihydroiso-benzofuran-5-ol (Intermediate 29 enantiomer 2) | LC/MS: QC_3_MIN: Rt = 2.296 min; m/z 408 [M + H]+. | $^1$H-NMR (400 MHz, DMSO-d$_6$): δ ppm 8.62 (br.s, 1H), 8.15 (d, 1H), 7.91 (dd, 1H), 7.48 (d, 1H), 7.28 (dd, 1H), 7.17-7.22 (m, 2H), 5.81-5.89 (m, 1H), 5.12-5.25 (m, 2H), 1.41 (s, 6H). |
| 62 | 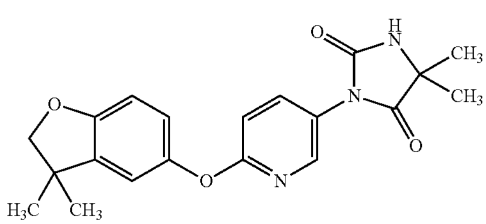 [SMILES: CC1(C)NC(=O)N(c2ccc(Oc3ccc4c(c3)C(C)(C)CO4)nc2)C1=O] | 3-[6-[(3,3-dimethyl-2H-benzofuran-5-yl)oxy]-3-pyridyl]-5,5-dimethyl-imidazolidine-2,4-dione | 3,3-dimethyl-2H-benzofuran-5-ol (Intermediate 44) | LC/MS: QC_3_MIN: Rt = 2.238 min; m/z 368 [M + H]+, 757 [2M + Na]+. | $^1$H-NMR (400 MHz, DMSO-d$_6$): δ ppm 8.60 (s, 1H), 8.13 (d, 1H), 7.83 (dd, 1H), 7.02-7.07 (m, 2H), 6.88 (dd, 1H), 6.78 (d, 1H), 4.25 (s, 2H), 1.40 (s, 6H), 1.29 (s, 6H). |
| 63 | 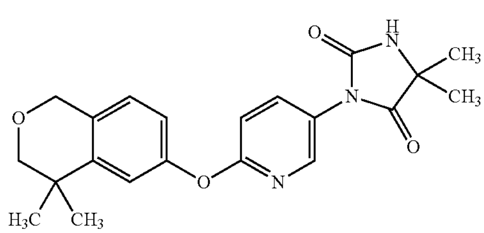 [SMILES: CC1(C)NC(=O)N(c2ccc(Oc3ccc4c(c3)C(C)(C)COC4)nc2)C1=O] | 3-[6-(4,4-dimethyliso-chroman-6-yl)oxy-3-pyridyl]-5,5-dimethyl-imidazolidine-2,4-dione | 4,4-dimethyl-3,4-dihydro-1H-isochromen-6-ol (Intermediate 42) | LC/MS: QC_3_MIN: Rt = 2.206 min; m/z 382 [M + H]+. | |

Example 64

(5R)-3-[6-[(3,3-dimethyl-1H-isobenzofuran-5-yl)oxy]-5-methyl-3-pyridyl]-5-ethyl-5-methyl-imidazolidine-2,4-dione

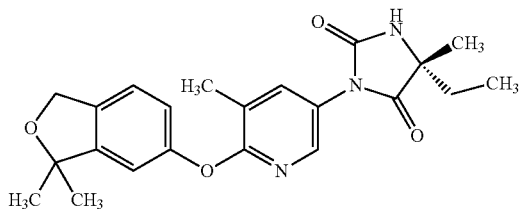 [SMILES: CC[C@@]1(C)NC(=O)N(c2cnc(Oc3ccc4c(c3)C(C)(C)OC4)c(C)c2)C1=O]

To a solution of (5R)-5-ethyl-3-(6-fluoro-5-methyl-3-pyridyl)-5-methyl-imidazolidine-2,4-dione (Intermediate 5, 48 mg, 0.19 mmol) in DMF (1 ml) 3,3-dimethyl-1H-isobenzofuran-5-ol (Intermediate 18, 45 mg, 0.27 mmol) and dipotassium carbonate (75.7 mg, 0.55 mmol) were added and the reaction mixture was stirred at 110° C. for 10 hours. The reaction was quenched with an aqueous saturated solution of ammonium chloride (5 ml) and extracted with ethyl acetate (10 ml). The organic layer was washed with brine (3×10 ml) dried over sodium sulphate and concentrated under vacuum. The residue was purified by flash chromatography on silica gel (Biotage system) using a SNAP 10 g as column and cyclohexane/ethyl acetate from 85:15 to 20:80 as eluent to afford the title compound (20 mg) as white solid.

LC/MS: QC_3_MIN: Rt=1.943 min; m/z 396 [M+H]+, 813 [2M+Na]+.

$^1$H-NMR (400 MHz, DMSO-d$_6$): δ ppm 8.55 (br.s, 1H), 7.90 (d, 1H), 7.73 (d, 1H), 7.27 (d, 1H), 7.07 (d, 1H), 7.00 (dd, 1H), 4.96 (s, 2H), 2.34 (s, 3H), 1.72-1.82 (m, 1H), 1.59-1.69 (m, 1H), 1.42 (s, 6H), 1.38 (s, 3H), 0.85 (t, 3H).

The following compounds were prepared using the foregoing methodology, replacing 3,3-dimethyl-1H-isobenzofuran-5-ol (Intermediate 18) with the appropriate phenol. Final products were purified by flash-chromatography (Silica cartridge using cyclohexane/EtOAc as eluents or reverse phase C18 column using water/acetonitrile as eluents).

| | Structure | Name | Phenol | LC/MS | $^1$H-NMR |
|---|---|---|---|---|---|
| 65 | 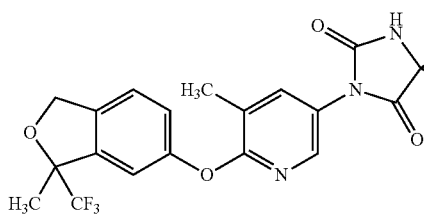 | (5R)-5-ethyl-5-methyl-3-[5-methyl-6-[[3-methyl-3-(trifluoromethyl)-1H-isobenzofuran-5-yl]oxy]-3-pyridyl]imidazolidine-2,4-dione (diastereoisomer 1) | 3-methyl-3-(trifluoromethyl)-1,3-dihydro-2-benzofuran-5-ol (Intermediate 32 enantiomer 1) | LC/MS: QC_3_MIN: Rt = 2.520 min; m/z 450 [M + H]+. | $^1$H-NMR (400 MHz, DMSO-d$_6$): δ ppm 8.55 (br.s, 1H), 7.91 (d, 1H), 7.75 (d, 1H), 7.43 (d, 1H), 7.21-7.28 (m, 2H), 5.11-5.22 (m, 2H), 2.36 (s, 3H), 1.71-1.81 (m, 1H), 1.58-1.69 (m, 4H), 1.38 (s, 3H), 0.86 (t, 3H). |
| 66 | 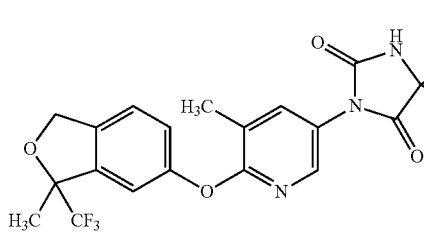 | (5R)-5-ethyl-5-methyl-3-[5-methyl-6-[[3-methyl-3-(trifluoromethyl)-1H-isobenzofuran-5-yl]oxy]-3-pyridyl]imidazolidine-2,4-dione (diastereoisomer 2) | 3-methyl-3-(trifluoromethyl)-1,3-dihydro-2-benzofuran-5-ol (Intermediate 33 enantiomer 2) | LC/MS: QC_3_MIN: Rt = 2.477 min; m/z 450 [M + H]+. | $^1$H-NMR (400 MHz, DMSO-d$_6$): δ ppm 8.55 (br.s, 1H), 7.91 (d, 1H), 7.75 (d, 1H), 7.43 (d, 1H), 7.21-7.28 (m, 2H), 5.11-5.22 (m, 2H), 2.36 (s, 3H), 1.71-1.81 (m, 1H), 1.58-1.69 (m, 4H), 1.38 (s, 3H), 0.86 (t, 3H). |
| 67 | 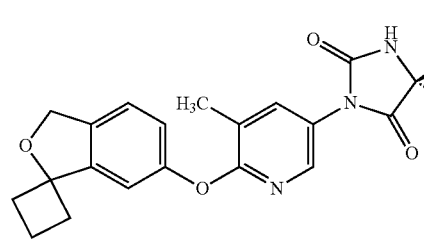 | (5R)-5-ethyl-5-methyl-3-(5-methyl-6-spiro[1H-isobenzofuran-3,1'-cyclobutane]-5-yloxy-3-pyridyl)imidazolidine-2,4-dione | 3H-spiro[2-benzofuran-1,1'-cyclobutan]-6-ol (Intermediate 24) | LC/MS: QC_3_MIN: Rt = 2.025 min; m/z 408 [M + H]+. | $^1$H-NMR (400 MHz, DMSO-d$_6$): δ ppm 8.55 (br.s, 1H), 7.90 (d, 1H), 7.74 (d, 1H), 7.33 (d, 1H), 7.27 (d, 1H), 7.03 (dd, 1H), 4.95 (s, 2H), 1.42-1.52 (m, 2H), 2.27-2.38 (m, 5H), 1.59-1.94 (m, 4H), 1.38 (s, 3H), 0.86 (t, 3H). |

| 68 | ![structure] | (5R)-5-ethyl-5-methyl-3-[5-methyl-6-[[3-(trifluoromethyl)-1,3-dihydroisobenzofuran-5-yl]oxy]-3-pyridyl]imidazolidine-2,4-dione (diastereoisomer 1) | 3-(trifluoromethyl)-1,3-dihydroisobenzofuran-5-ol (Intermediate 28 enantiomer 1) | LC/MS: QC_3_MIN: Rt = 2.449 min; m/z 436 [M + H]+. | $^1$H-NMR (400 MHz, DMSO-d$_6$): δ ppm 8.56 (br.s, 1H), 7.91 (d, 1H), 7.76 (d, 1H), 7.46 (d, 1H), 7.24 (dd, 1H), 7.15-7.19 (m, 1H), 5.80-5.88 (m, 1H), 5.15-5.25 (m, 2H), 2.35 (s, 3H), 1.72-1.82 (m, 1H), 1.59-1.69 (m, 1H), 1.38 (s, 3H), 0.85 (t, 3H). |
|---|---|---|---|---|---|
| 69 | ![structure] | (5R)-5-ethyl-5-methyl-3-[5-methyl-6-[[3-(trifluoromethyl)-1,3-dihydroisobenzofuran-5-yl]oxy]-3-pyridyl]imidazolidine-2,4-dione (diastereoisomer 2) | 3-(trifluoromethyl)-1,3-dihydroisobenzofuran-5-ol (Intermediate 29 enantiomer 2) | LC/MS: QC_3_MIN: Rt = 2.468 min; m/z 436 [M + H]+. | $^1$H-NMR (400 MHz, DMSO-d$_6$): δ ppm 8.56 (br.s, 1H), 7.91 (d, 1H), 7.76 (d, 1H), 7.46 (d, 1H), 7.24 (dd, 1H), 7.15-7.19 (m, 1H), 5.80-5.88 (m, 1H), 5.15-5.25 (m, 2H), 2.35 (s, 3H), 1.72-1.82 (m, 1H), 1.59-1.69 (m, 1H), 1.38 (s, 3H), 0.85 (t, 3H). |

Example 70

5,5-dimethyl-3-(5-methyl-6-{[3-(trifluoromethyl)-1,3-dihydro-2-benzofuran-5-yl]oxy}pyridin-3-yl)imidazolidine-2,4-dione (Enantiomer 1)

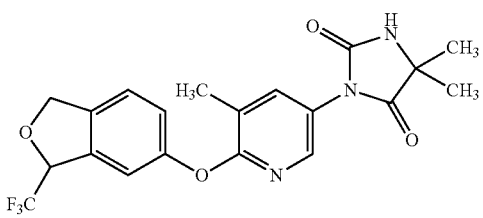 [SMILES: Cc1cc(N2C(=O)NC(C)(C)C2=O)cnc1Oc1ccc2c(c1)C(C(F)(F)F)OC2]

To a solution of 3-(trifluoromethyl)-1,3-dihydroisobenzofuran-5-ol (enantiomer 1) (Intermediate 28, 20 mg, 0.098 mmol) and 3-(6-fluoro-5-methyl-3-pyridyl)-5,5-dimethyl-imidazolidine-2,4-dione (Intermediate 6, 27.9 mg, 0.118 mmol) in DMF (1 mL) dipotassium carbonate (27.1 mg, 0.196 mmol) was added and the reaction mixture was stirred for 48 hours at 110° C. After cooling the mixture was diluted with water (5 ml) and extracted with ethyl acetate (2×10 ml). The organic layer was dried (Na$_2$SO$_4$), filtered and evaporated and the residue was purified by reverse phase flash chromatography on C18 column (MEGA BE Varian, 5 g) using water/acetonitrile from 100:0 to 0:100 as eluent affording the title compound (5 mg) as white solid.

LC/MS: QC_3_MIN: Rt=2.373 min; m/z 422 [M+H]+.

$^1$H-NMR (400 MHz, DMSO-d$_6$): δ ppm 8.61 (br.s, 1H), 7.93 (d, 1H), 7.78 (d, 1H), 7.46 (d, 1H), 7.24 (dd, 1H), 7.15-7.19 (m, 1H), 5.80-5.88 (m, 1H), 5.15-5.25 (m, 2H), 2.35 (s, 3H), 1.40 (s, 6H).

Example 71

5,5-dimethyl-3-(5-methyl-6-{[3-(trifluoromethyl)-1,3-dihydro-2-benzofuran-5-yl]oxy}pyridin-3-yl)imidazolidine-2,4-dione (Enantiomer 2)

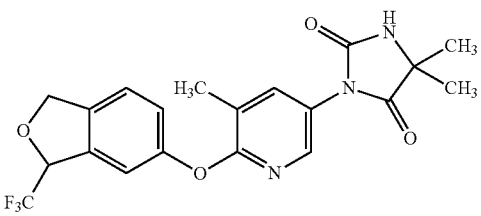 [SMILES: Cc1cc(N2C(=O)NC(C)(C)C2=O)cnc1Oc1ccc2c(c1)C(C(F)(F)F)OC2]

The title compound was prepared using the methodology described for Example 69, replacing 3-(trifluoromethyl)-1,3-dihydroisobenzofuran-5-ol (enantiomer 1) (Intermediate 28) with 3-(trifluoromethyl)-1,3-dihydroisobenzofuran-5-ol (enantiomer 2) (Intermediate 29). Final products was purified by flash-chromatography on C18 column (MEGA BE Varian, 5 g) using water/acetonitrile from 100:0 to 0:100 as eluent.

LC/MS: QC_3_MIN: Rt=2.335 min; m/z 422 [M+H]+, 865 [2M+Na]+.

¹H-NMR (400 MHz, DMSO-d₆): δ ppm 8.61 (br.s, 1H), 7.93 (d, 1H), 7.78 (d, 1H), 7.46 (d, 1H), 7.24 (dd, 1H), 7.15-7.19 (m, 1H), 5.80-5.88 (m, 1H), 5.15-5.25 (m, 2H), 2.35 (s, 3H), 1.40 (s, 6H).

Example 72

(5R)-3-[6-[(3,3-dimethyl-1H-isobenzofuran-5-yl)oxy]-3-pyridyl]-5-ethyl-imidazolidine-2,4-dione

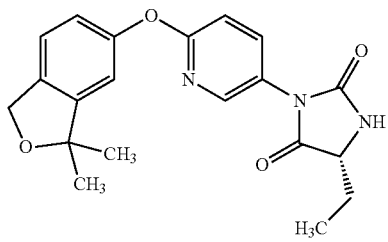 [SMILES: CC[C@H]1NC(=O)N(c2ccc(Oc3ccc4c(c3)C(C)(C)OC4)nc2)C1=O]

To a solution of (2R)-2-amino-N-[6-[(3,3-dimethyl-1H-isobenzofuran-5-yl)oxy]-3-pyridyl]butanamide (Intermediate 61, 18 mg, 0.0527 mmol) in DCM (4 mL) N,N-diethylethanamine (0.022 ml, 0.16 mmol) was added and the reaction mixture was cooled to 0° C. A solution of bis(trichloromethyl) carbonate (7.8 mg, 0.026 mmol) in DCM (1 mL) was slowly added and the reaction mixture was stirred for 30 minutes at the same temperature. The reaction was diluted with DCM (5 ml) and washed with an aqueous saturated solution of NH₄Cl (10 ml). The organic layer was dried (Na₂SO₄), filtered and evaporated and the residue was purified by flash chromatography (Biotage system) on silica gel using a SNAP 10 g as column and cyclohexane/ethyl acetate from 80:20 to 10:90 as eluent affording the title compound (16 mg) as white solid.

LC/MS: QC_3_MIN: Rt=2.159 min; m/z 368 [M+H]+.

¹H-NMR (400 MHz, DMSO-d₆): δ ppm 8.60 (br.s, 1H), 8.12 (d, 1H), 7.84 (dd, 1H), 7.29 (d, 1H), 7.13 (d, 1H), 7.11 (d, 1H), 7.04 (dd, 1H), 4.96 (s, 2H), 4.18-4.23 (m, 1H), 1.75-1.85 (m, 1H), 1.65-1.75 (m, 1H), 1.42 (s, 6H), 0.95 (t, 3H).

The following compounds were prepared using the foregoing methodology, replacing (2R)-2-amino-N-[6-[(3,3-dimethyl-1H-isobenzofuran-5-yl)oxy]-3-pyridyl]butanamide (Intermediate 61) with the appropriate amino amide. Final products were purified by flash-chromatography (Silica cartridge; cyclohexane/EtOAc, dichloromethane/methanol or other appropriate solvent system).

| Ex. | Structure | Name | Amino amide | LCMS | NMR |
|---|---|---|---|---|---|
| 73 | 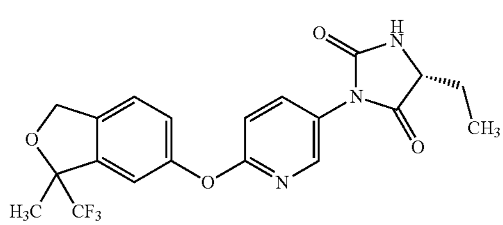 [SMILES: CC[C@H]1NC(=O)N(c2ccc(Oc3ccc4c(c3)C(C)(C(F)(F)F)OC4)nc2)C1=O] | (5R)-5-ethyl-3-[6-[[3-methyl-3-(trifluoromethyl)-1H-isobenzofuran-5-yl]oxy]-3-pyridyl]imidazolidine-2,4-dione (diastereoisomer 1) | (2R)-2-amino-N-(6-{[3-methyl-3-(trifluoromethyl)-1,3-dihydro-2-benzofuran-5-yl]oxy}pyridin-3-yl)butanamide (diastereoisomer 1) (Intermediate 62) | LC/MS: QC_3_MIN: Rt = 2.330 min; m/z 422 [M + H]+. | ¹H-NMR (400 MHz, DMSO-d₆): δ ppm 8.61 (br.s, 1H), 8.13 (d, 1H), 7.87 (dd, 1H), 7.44 (d, 1H), 7.24-7.30 (m, 2H), 7.18 (d, 1H), 5.11-5.21 (m, 2H), 4.18-4.23 (m, 1H), 1.76-1.86 (m, 1H), 1.65-1.75 (m, 1H), 1.65 (s, 3H), 0.95 (t, 3H). |
| 74 | 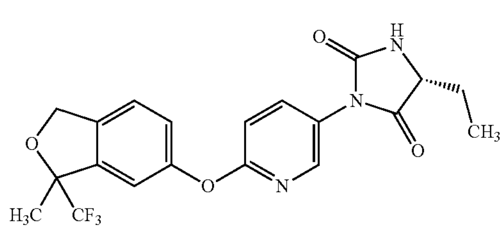 [SMILES: CC[C@H]1NC(=O)N(c2ccc(Oc3ccc4c(c3)C(C)(C(F)(F)F)OC4)nc2)C1=O] | (5R)-5-ethyl-3-[6-[[3-methyl-3-(trifluoromethyl)-1H-isobenzofuran-5-yl]oxy]-3-pyridyl]imidazolidine-2,4-dione (diastereoisomer 2) | (2R)-2-amino-N-(6-{[3-methyl-3-(trifluoromethyl)-1,3-dihydro-2-benzofuran-5-yl]oxy}pyridin-3-yl)butanamide (diastereoisomer 2) (Intermediate 63) | LC/MS: QC_3_MIN: Rt = 2.266 min; m/z 422 [M + H]+. | ¹H-NMR(400 MHz, DMSO-d₆): δ ppm 8.61 (br.s, 1H), 8.13 (d, 1H), 7.87 (dd, 1H), 7.44 (d, 1H), 7.24-7.30 (m, 2H), 7.18 (d, 1H), 5.11-5.21 (m, 2H), 4.18-4.23 (m, 1H), 1.76-1.86 (m, 1H), 1.65-1.75 (m, 1H), 1.65 (s, 3H), 0.95 (t, 3H). |

-continued

| Ex. | Structure | Name | Amino amide | LCMS | NMR |
|---|---|---|---|---|---|
| 75 | 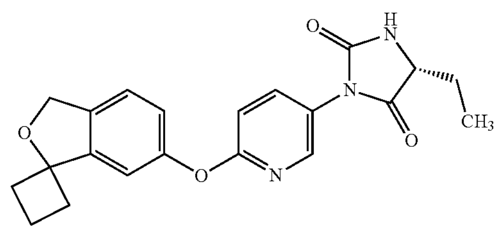 [SMILES: CC[C@H]1NC(=O)N(c2ccc(Oc3ccc4c(c3)C3(CCC3)OC4)nc2)C1=O] | (5R)-5-ethyl-3-(6-spiro[1H-isobenzofuran-3,1'-cyclobutane]-5-yloxy-3-pyridyl)imidazolidine-2,4-dione | (2R)-2-amino-N-[6-(3H-spiro[2-benzofuran-1,1'-cyclobutan]-6-yloxy)pyridin-3-yl]butanamide (Intermediate 64) | LC/MS: QC_3_MIN: Rt = 2.254 min; m/z 380 [M + H]+. | $^1$H-NMR(400 MHz, DMSO-d$_6$): δ ppm 8.60 (br.s, 1H), 8.12 (d, 1H), 7.85 (dd, 1H), 7.36 (d, 1H), 7.29 (d, 1H), 7.15 (d, 1H), 7.07 (dd, 1H), 4.96 (s, 2H), 4.18-4.23 (m, 1H), 2.43-2.53 (m, 2H), 2.28-2.38 (m, 2H), 1.76-1.96 (m, 3H), 1.64-1.74 (m, 1H), 0.95 (t, 3H). |
| 76 | 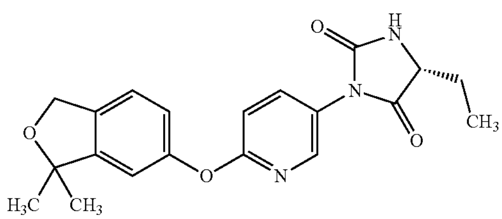 | (5R)-3-[6-[(3,3-dimethyl-2H-benzofuran-5-yl)oxy]-3-pyridyl]-5-ethyl-imidazolidine-2,4-dione | (2R)-2-amino-N-{6-[(3,3-dimethyl-2,3-dihydro-1-benzofuran-5-yl)oxy]pyridin-3-yl}butanamide (Intermediate 65) | LC/MS: QC_3_MIN: Rt = 2.238 min; m/z 368 [M + H]+. | $^1$H-NMR(400 MHz, DMSO-d$_6$): δ ppm 8.59 (br.s, 1H), 8.10 (d, 1H), 7.80 (dd, 1H), 7.02-7.07 (m, 2H), 6.88 (dd, 1H), 6.78 (d, 1H), 4.25 (s, 2H), 4.18-4.23 (m, 1H), 1.75-1.86 (m, 1H), 1.63-1.74 (m, 1H), 1.29 (s, 6H), 0.95 (t, 3H). |
| 77 | 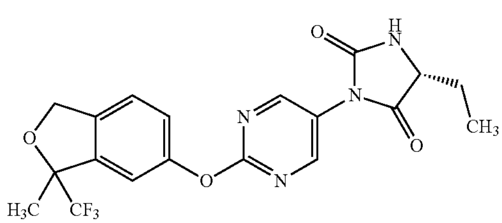 | (5R)-5-ethyl-3-[2-[[3-methyl-3-(trifluoromethyl)-1H-isobenzofuran-5-yl]oxy]pyrimidin-5-yl]imidazolidine-2,4-dione (diastereoisomer 1) | (2R)-2-amino-N-(2-{[3-methyl-3-(trifluoromethyl)-1,3-dihydro-2-benzofuran-5-yl]oxy}pyrimidin-5-yl)butanamide (diastereoisomer 1) (Intermediate 66) | LC/MS: QC_3_MIN: Rt = 2.303 min; m/z 423 [M + H]+. | $^1$H-NMR (400 MHz, DMSO-d$_6$): δ ppm 8.74 (br.s, 1H), 8.70 (s, 2H), 7.47 (d, 1H), 7.38-7.41 (m, 1H), 7.35 (dd, 1H), 5.12-5.22 (m, 2H), 4.20-4.26 (m, 1H), 1.77-1.88 (m, 1H), 1.66-1.77 (m, 1H), 1.65 (s, 3H), 0.96 (t, 3H). |
| 78 | 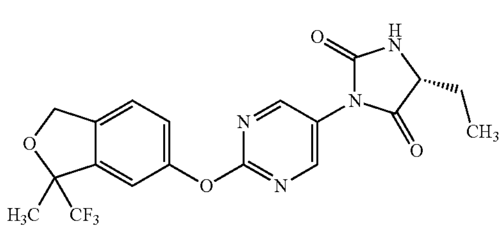 | (5R)-5-ethyl-3-[2-[[3-methyl-3-(trifluoromethyl)-1H-isobenzofuran-5-yl]oxy]pyrimidin-5-yl]imidazolidine-2,4-dione (diastereoisomer 2) | (2R)-2-amino-N-(2-{[3-methyl-3-(trifluoromethyl)-1,3-dihydro-2-benzofuran-5-yl]oxy}pyrimidin-5-yl)butanamide (diastereoisomer 2) (Intermediate 67) | LC/MS: QC_3_MIN: Rt = 2.199 min; m/z 423 [M + H]+. | $^1$H-NMR (400 MHz, DMSO-d$_6$): δ ppm 8.74 (br.s, 1H), 8.70 (s, 2H), 7.47 (d, 1H), 7.38-7.41 (m, 1H), 7.35 (dd, 1H), 5.12-5.22 (m, 2H), 4.20-4.26 (m, 1H), 1.77-1.88 (m, 1H), 1.66-1.77 (m, 1H), 1.65 (s, 3H), 0.96 (t, 3H). |

| Ex. | Structure | Name | Amino amide | LCMS | NMR |
|---|---|---|---|---|---|
| 79 | 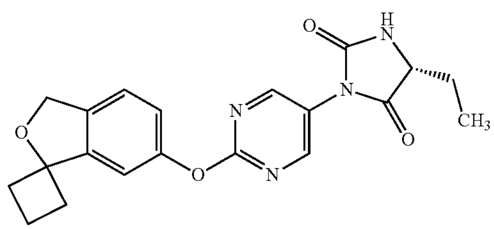 [SMILES: CC[C@H]1NC(=O)N(c2cnc(Oc3ccc4c(c3)C3(CCC3)OC4)nc2)C1=O] | (5R)-5-ethyl-3-(2-spiro[1H-isobenzofuran-3,1'-cyclobutane]-5-yloxypyrimidin-5-yl)imidazolidine-2,4-dione | (2R)-2-amino-N-[2-(3H-spiro[2-benzofuran-1,1'-cyclobutan]-6-yloxy)pyrimidin-5-yl]butanamide (Intermediate 68) | LC/MS: QC_3_MIN: Rt = 2.107 min; m/z 381[M + H]+. | ¹H-NMR (400 MHz, DMSO-d₆): δ ppm 8.73 (br.s, 1H), 8.69 (s, 2H), 7.45 (dd, 1H), 7.31 (d, 1H), 7.15 (dd, 1H), 4.97 (s, 2H), 4.21-4.26 (m, 1H), 2.43-2.53 (m, 2H), 2.28-2.38 (m, 2H), 1.63-1.98 (m, 4H), 0.97 (t, 3H). |

Example 80

(5R)-3-{4-[(3,3-dimethyl-1,3-dihydro-2-benzofuran-5-yl)oxy]phenyl}-5-ethyl-5-methyl-2,4-imidazolidinedione

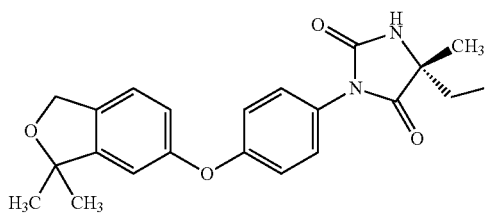

(2R)-2-amino-N-[4-[(3,3-dimethyl-1H-isobenzofuran-5-yl)oxy]phenyl]-2-methyl-butanamide (Intermediate 71, 140 mg, 0.39 mmol) was dissolved in ethyl acetate (2 mL) and the resulting solution was added drop wise to a suspension of CDI (1.4 equiv) in ethyl acetate (0.5 mL). The resulting suspension was stirred overnight. A new solution of CDI was freshly prepared (60 mg in 0.5 mL of ethyl acetate) and added drop wise to the mixture. A third portion of CDI (50 mg) was added and the reaction mixture was left stirring over week-end at room temperature. The mixture was treated with 10% w/w aqueous citric acid solution, two layers were separated and the organic layer washed with water and brine, then dried over Na₂SO₄ and evaporated to dryness. The residue was purified by flash chromatography on silica gel using cyclohexane/ethyl acetate from 80:20 to 60:40 as eluent. The fractions containing the product were combined, evaporated to dryness and further purified by crystallization from ethyl acetate/n-heptane. The slurry was stirred for 2 hours, and then the solid collected, washed with n-heptane and dried under vacuum. The residue was re-purified by flash chromatography on silica gel using dichloromethane/methanol from 100:0 to 90:10. The fractions containing the product were combined, evaporated to dryness and the residue further purified by crystallization from methyl tertbutyl ether/n-heptane to afford the title compound (47 mg) as white solid.

UPLC_A: Rt=1.02 min, m/z 381 [M+H]+, 761 [2M+H]+.

¹H-NMR (400 MHz, DMSO-d₆): δ ppm 8.47 (s, 1H), 7.34-7.30 (m, 2H), 7.28 (d, 1H), 7.07-7.03 (m, 3H), 6.94 (dd, 1H), 4.94 (s, 2H), 1.81-1.72 (m, 1H), 1.69-1.59 (m, 1H), 1.41 (s, 6H), 1.37 (s, 3H), 0.85 (t, 3H). ¹³C-NMR (200 MHz, DMSO-d6): δ ppm 175.9, 156.7, 155.5, 154.8, 149.3, 134.0, 128.5, 126.8, 122.6, 118.4, 117.8, 112.1, 85.0, 69.5, 61.3, 30.5, 28.0, 23.2, 7.7.

Example 81

(5R)-3-[4-(1,3-dihydro-2-benzofuran-5-yloxy)phenyl]-5-methyl-2,4-imidazolidinedione

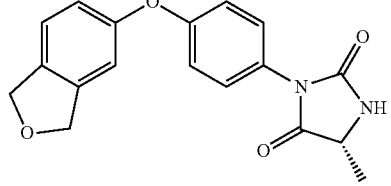

A solution of N¹-[4-(1,3-dihydro-2-benzofuran-5-yloxy)phenyl]-D-alaninamide (Intermediate 77, 100 mg, 0.335 mmol) and TEA (0.234 ml, 1.676 mmol) in dichloromethane (10 ml) was stirred under argon at 0° C. Triphosgene (49.7 mg, 0.168 mmol) in dichloromethane (4 ml) was added and the mixture was left stirring at 0° C. for 15 minutes. After 30 min an aqueous saturated solution of NaHCO₃ was added. The phases were separated and the aqueous phase was extracted 3 times with dichloromethane. The gathered organic phases were dried over sodium sulphate and concentrated under vacuum. The residue obtained was purified by flash chromatography (Biotage SP1), using as eluents a gradient cyclohexane/ethyl acetate 90:10 to 65:45 to 20:80. This afforded the title compound (20 mg).

¹H NMR (400 MHz, DMSO-d₆): δ ppm 8.37-8.53 (1H, m), 7.42-7.26 (3H, m), 7.10-7.04 (m, 2H), 7.04-6.94 (2H, m), 4.98 (4H, s) 4.21-4.28 (1H, m) 1.35 (3H, d); UPLC_A: Rt=0.67 min, m/z 325 [M+1]+

Biological Example 1

The ability of the compounds of the invention to modulate the voltage-gated potassium channel subtypes Kv3.2/3.1 may be determined using the following assay. Analogous methods may be used to investigate the ability of the compounds of the invention to modulate other channel subtypes, including Kv3.3 and Kv3.4.

Cell Biology

To assess compound effects on human Kv3.2 channels (hKv3.2), a stable cell line expressing human Kv3.2 channels (hKv3.2) was created by transfecting Chinese Hamster Ovary (CHO)—K1 cells with a pCIH5-hKv3.2 vector. Cells were cultured in DMEM/F12 medium supplemented by 10% Foetal Bovine Serum, 1× non-essential amino acids (Invitrogen) and 500 ug/ml of Hygromycin-B (Invitrogen). Cells were grown and maintained at 37° C. in a humidified environment containing 5% $CO_2$ in air.

To assess compound effects on human Kv3.1 channels (hKv3.1), CHO/Gam/E1A-clone22 alias CGE22 cells were transduced using a hKv3.1 BacMam reagent. This cell line was designed to be an improved CHO-K1-based host for enhanced recombinant protein expression as compared to wild type CHO-K1. The cell line was generated following the transduction of CHO-K1 cells with a BacMam virus expressing the Adenovirus-Gam1 protein and selection with Geneticin-G418, to generate a stable cell line, CHO/Gam-A3. CHO/Gam-A3 cells were transfected with pCDNA3-E1A-Hygro, followed by hygromycin-B selection and FACS sorting to obtain single-cell clones. BacMam-Luciferase and BacMam-GFP viruses were then used in transient transduction studies to select the clone based on highest BacMam transduction and recombinant protein expression. CGE22 cells were cultured in the same medium used for the hKv3.2 CHO-K1 stable cell line with the addition of 300 ug/ml hygromycin-B and 300 ug/ml G418. All other conditions were identical to those for hKv3.2 CHO-K1 cells. The day before an experiment 10 million CGE22 cells were plated in a T175 culture flask and the hKv3.1 BacMam reagent (pFBM/human Kv3.1) was added (MOI of 50). Transduced cells were used 24 hours later.

Cell Preparation for IonWorks Quattro™ Experiments

The day of the experiment, cells were removed from the incubator and the culture medium removed. Cells were washed with 5 ml of Dulbecco's PBS (DPBS) calcium and magnesium free and detached by the addition of 3 ml Versene (Invitrogen, Italy) followed by a brief incubation at 37° C. for 5 minutes. The flask was tapped to dislodge cells and 10 ml of DPBS containing calcium and magnesium was added to prepare a cell suspension. The cell suspension was then placed into a 15 ml centrifuge tube and centrifuged for 2 min at 1200 rpm. After centrifugation, the supernatant was removed and the cell pellet re-suspended in 4 ml of DPBS containing calcium and magnesium using a 5 ml pipette to break up the pellet. Cell suspension volume was then corrected to give a cell concentration for the assay of approximately 3 million cells per ml.

All the solutions added to the cells were pre-warmed to 37° C.

Electrophysiology

Experiments were conducted at room temperature using IonWorks Quattro™ planar array electrophysiology technology (Molecular Devices Corp.) with PatchPlate™ PPC. Stimulation protocols and data acquisition were carried out using a microcomputer (Dell Pentium 4). Planar electrode hole resistances(Rp) were determined by applying a 10 mV voltage step across each well. These measurements were performed before cell addition. After cell addition and seal formation, a seal test was performed by applying a voltage step from −80 mV to −70 mV for 160 ms. Following this, amphotericin-B solution was added to the intracellular face of the electrode to achieve intracellular access. Cells were held at −70 mV. Leak subtraction was conducted in all experiments by applying 50 ms hyperpolarizing (10 mV) prepulses to evoke leak currents followed by a 20 ms period at the holding potential before test pulses. From the holding potential of −70 mV, a first test pulse to −15 mV was applied for 100 ms and following a further 100 ms at −70 mV, a second pulse to 40 mV was applied for 50 ms. Cells were then maintained for a further 100 ms at −100 mV and then a voltage ramp from −100 mV to 40 mV was applied over 200 ms. Test pulses protocol may be performed in the absence (pre-read) and presence (post-read) of the test compound. Pre- and post-reads may be separated by the compound addition followed by a 3 minute incubation.

Solutions and Drugs

The intracellular solution contained the following (in mM): K-gluconate 100, KCl 54, MgCl2 3.2, HEPES 5, adjusted to pH 7.3 with KOH. Amphotericin-B solution was prepared as 50 mg/ml stock solution in DMSO and diluted to a final working concentration of 0.1 mg/ml in intracellular solution. The external solution was Dulbecco's Phosphate Buffered Saline (DPBS) and contained the following (in mM): CaCl2 0.90, KCl 2.67, KH2PO4 1.47, MgCl.6H2O 0.493, NaCl 136.9, $Na_3PO_4$ 8.06, with a pH of 7.4.

Compounds of the invention (or reference compounds such as N-cyclohexyl-N-[(7,8-dimethyl-2-oxo-1,2-dihydro-3-quinolinyl)methyl]-N'-phenylurea were dissolved in dimethylsulfoxide (DMSO) at a stock concentration of 10 mM. These solutions were further diluted with DMSO using a Biomek FX (Beckman Coulter) in a 384 compound plate. Each dilution (1 μL) was transferred to another compound plate and external solution containing 0.05% pluronic acid (66 μL) was added. 3.5 μL from each plate containing a compound of the invention was added and incubated with the cells during the IonWorks Quattro™ experiment. The final assay dilution was 200 and the final compound concentrations were in the range 50 μM to 50 nM.

Data Analysis

The recordings were analysed and filtered using both seal resistance (>20 MΩ) and peak current amplitude (>500 pA at the voltage step of 40 mV) in the absence of compound to eliminate unsuitable cells from further analysis. Paired comparisons between pre- and post-drug additions measured for the −15 mV voltage step were used to determine the positive modulation effect of each compound. Kv3 channel-mediated outward currents were determined from the mean amplitude of the current over the final 10 ms of the −15 mV voltage pulse minus the mean baseline current at −70 mV over a 10 ms period just prior to the −15 mV step. These Kv3 channel currents following addition of the test compound were then compared with the currents recorded prior to compound addition. Data were normalised to the maximum effect of the reference compound (50 microM of N-cyclohexyl-N-[(7,8-dimethyl-2-oxo-1,2-dihydro-3-quinolinyl)methyl]-N'-phenylurea) and to the effect of a vehicle control (0.5% DMSO). The normalised data were analysed using ActivityBase or Excel software. The concentration of compound required to increase currents by 50% of the maximum increase produced by the reference compound (EC50) was determined by fitting of the concentration-response data using a four parameter logistic function in ActivityBase.

N-cyclohexyl-N-[(7,8-dimethyl-2-oxo-1,2-dihydro-3-quinolinyl)methyl]-N'-phenylurea was obtained from ASINEX (Registry Number: 552311-06-5).

All of the Example compounds were tested in the above assay measuring potentiation of Kv3.1 or Kv3.2 or Kv3.1 and Kv3.2 (herein after "Kv3.1 and/or Kv3.2"). Kv3.1 and/or Kv3.2 positive modulators produce in the above assay an increase of whole-cell currents of, on average, at least 20% of the increase observed with 50 microM N-cyclohexyl-N-[(7,8-dimethyl-2-oxo-1,2-dihydro-3-quinolinyl)methyl]-N'- phenylurea. Thus, in the recombinant cell assays of Biological Example 1, all of the Example compounds act as positive modulators. As used herein, a Kv3.1 and/or Kv3.2 positive modulator is a compound which has been shown to produce at least 20% potentiation of whole-cell currents mediated by human Kv3.1 and/or human Kv3.2 channels recombinantly expressed in mammalian cells, as determined using the assays described in Biological Example 1 (Biological Assays).

Furthermore, all Examples were found to demonstrate a more balanced activity between Kv3.1 and Kv3.2 channels as compared to similar compounds of the prior art such as (5R)-5-ethyl-3-[6-(spiro[1-benzofuran-3,1'-cyclopropan]-4-yloxy)-3-pyridinyl]-2,4-imidazolidinedione (Reference Example 87 of WO2011069951A1) and 5,5-dimethyl-3-[6-(spiro[1-benzofuran-3,1'-cyclopropan]-4-yloxy)-3-pyridinyl]-2,4-imidazolidinedione (Reference Example 88 of WO2011069951A1). (5R)-5-ethyl-3-[6-(spiro[1-benzofuran-3,1'-cyclopropan]-4-yloxy)-3-pyridinyl]-2,4-imidazolidinedione and 5,5-dimethyl-3-[6-(spiro[1-benzofuran-3,1'-cyclopropan]-4-yloxy)-3-pyridinyl]-2,4-imidazolidinedione both demonstrate a 0.7 log unit difference in $pEC_{50}$ values between the two channels, whereas all example compounds demonstrate more comparable activities between channels and with a maximum difference in average $pEC_{50}$ values of only 0.42 log units. Locating the A ring in the meta/para position, which is a feature of all compounds of the present invention, therefore helps ensure comparable activities between Kv3.1 and Kv3.2 channels.

A secondary analysis of the data from the assays described in Biological Example 1 may be used to investigate the effect of the compounds on rate of rise of the current from the start of the depolarising voltage pulses. The magnitude of the effect of a compound can be determined from the time constant ($Tau_{act}$) obtained from a non-linear fit, using the equation given below, of the rise in Kv3.1 or Kv3.2 currents following the start of the −15 mV depolarising voltage pulse.

$$Y=(Y0-Ymax)*\exp(-K*X)+Ymax$$

where:
Y0 is the current value at the start of the depolarising voltage pulse;
Ymax is the plateau current;
K is the rate constant, and $Tau_{act}$ is the activation time constant, which is the reciprocal of K.

Similarly, the effect of the compounds on the time taken for Kv3.1 and Kv3.2 currents to decay on closing of the channels at the end of the −15 mV depolarising voltage pulses can also be investigated. In this latter case, the magnitude of the effect of a compound on channel closing can be determined from the time constant ($Tau_{deact}$) of a non-linear fit of the decay of the current ("tail current") immediately following the end of the depolarising voltage pulse.

Kv3.1 and Kv3.2 channels must activate and deactivate very rapidly in order to allow neurons to fire actions potentials at high frequency (Rudy and McBain, 2001, Trends in Neurosciences 24, 517-526). Slowing of activation is likely to delay the onset of action potential repolarisation; slowing of deactivation could lead to hyperpolarising currents that reduce the excitability of the neuron and delay the time before the neuron can fire a further action potential. Together these two slowing effects on channel activation and deactivation are likely to lead to a reduction rather than a facilitation of the neurons ability to fire at high frequencies. Thus compounds that have this slowing effect on the Kv3.1 and/or Kv3.2 channels will effectively behave as negative modulators of the channels, leading to a slowing of neuronal firing. This latter effect has been shown on "fast-firing" interneurons in the cortex of rat brain, using electrophysiological techniques, in vitro, for certain compounds disclosed in WO2011/069951, which produced a marked increases in $Tau_{act}$ in the Kv3.1 and Kv3.2 assays described above. The addition of the relevant compounds reduces the ability of the neurons to fire in response to trains of depolarising pulses at 300 Hz.

Therefore, although compounds of the invention may be identified act as positive modulators in the recombinant cell assay of Biological Example 1, those compounds which markedly increase the value of $Tau_{act}$ reduce the ability of neurons in native tissues to fire at high frequency.

Biological Example 2

Determination of Blood and Brain Tissue Binding

Materials and Methods

Rat whole blood, collected on the week of the experiment using K3-EDTA as an anti-coagulant, was diluted with isotonic phosphate buffer 1:1 (v/v). Rat whole brain, stored frozen at −20° C., was thawed and homogenised in artificial cerebrospinal fluid (CSF) 1:2 (w/v).

An appropriate amount of test compound was dissolved in DMSO to give a 5 millimolar solution. Further dilutions, to obtain a 166.7 micromolar working solution was then prepared using 50% acetonitrile in MilliQ water. This working solution was used to spike the blood to obtain a final concentration of 0.5 micromolar in whole blood. Similarly, the working solution was used to spike brain samples to obtain a final concentration of 5 micromolar in whole brain. From these spiked blood and brain preparations, control samples (n=3), were immediately extracted and used to calculate the initial recovery of the test items.

150 microL of compound-free buffer (isotonic phosphate buffer for blood or artificial CSF buffer for brain) was dispensed in one half-well and 150 microL of spiked matrix (blood or brain) was loaded in the other half-well, with the two halves separated by a semi-permeable membrane. After an equilibration period of 5 hours at 37° C., 50 microL of dialysed matrix (blood or brain) was added to 50 microL of corresponding compound-free buffer, and vice-versa for buffer, such that the volume of buffer to matrix (blood or brain) remained the same. Samples were then extracted by protein precipitation with 300 microL of acetonitrile containing rolipram (control for positive ionization mode) or diclofenac (control for negative ionization mode) as internal standards and centrifuged for 10 min at 2800 rpm. Supernatants were collected (100 microL), diluted with 18% ACN in MilliQ water (200 microL) and then injected into an HPLC-MS/MS or UPLC-MS/MS system to determine the concentration of test compound present.

Analysis

Blood and brain tissue binding were then determined using the following formulas:

Afu=Buffer/Blood or Afu=CSF/Brain

Where Afu=apparent fraction unbound; Buffer=analyte/internal standard ratio determined in the buffer compartment; Blood=analyte/internal standard ratio determined in the blood compartment; Brain=analyte/internal standard ratio determined in the brain compartment.

$$Fucr = \frac{1/D}{[(1/Afu - 1) + 1/D]}$$

where: fucr=Fraction unbound corrected; D=matrix dilution factor (D=2 for blood and D=3 for brain).
Then:

% Binding=(1−fucr)×100

% Unbound=100−% Bound

Brain/Blood Partition Ratio (Kbb) Determination

For compounds freely permeable across the blood/brain barrier (BBB), the unbound concentrations in blood and brain would be equivalent under steady-state distribution conditions. Therefore, the Kbb value could be calculated as:

Fu(blood)/Fu(brain)

which is expected to be equivalent to the brain-to-blood concentration ratio (Ct(brain)/Ct(blood)) if efflux pump transporters are not involved.

Determination of In Vivo Pharmacokinetic Parameters
Materials and Methods

Adult male rats (Charles River, Italy) were dosed with test compound orally at 1 mg/kg (5 ml/kg, in 5% v/v DMSO, 0.5% w/v HPMC in water) and intravenously at 0.5 mg/kg (2 ml/kg, in 5% v/v DMSO 40% w/v PEG400 in saline). After oral administration, blood samples were collected under deep Isofluorane anesthesia from the portal vein and heart of each rat (1 rat per time point). After intravenous administration, serial blood samples were collected from the lateral tail vein of each rat. A further group of rats (n=1 per test compound) received a single intravenous administration of the PgP transport inhibitor, Elacridar (3 mg/kg) shortly before the oral administration of the test compound at 1 mg/kg, as above. Blood and brain samples were collected at a single timepoint of 0.5 h after dose administration for these animals. In all cases, blood samples were collected into potassium EDTA tubes.

Blood and brain samples were assayed for test compound concentration using a method based on protein precipitation with acetonitrile followed by HPLC/MS-MS analysis with an optimized analytical method.

Analysis

The concentrations of test compound in blood (expressed as ng/ml) and brain (expressed as ng/g) at the different time points following either oral or intravenous dosing were analysed using a non-compartmental pharmacokinetic model using WinNonLin Professional version 4.1. The following parameters were derived:

Intravenous dosing: Maximum concentration over time (Cmax), integrated concentration over time (AUC), clearance (Clb), volume of distribution (Vss) and half-life (t½).

Oral dosing: Cmax, time of maximum concentration (Tmax), AUC, bioavailability (F %), fraction absorbed (Fa %), blood to brain ratio (AUC BB), and Fold-change in AUC BB in the presence of Elacridar.

In the above in vivo pharmacokinetic assay, Examples 12, 33, 50, 52 and 58 were each found to demonstrate AUC BB values of at least 1.7 fold that of (5R)-5-ethyl-3-[6-(spiro[1-benzofuran-3,1'-cyclopropan]-4-yloxy)-3-pyridinyl]-2,4-imidazolidinedione (Reference Example 87 of WO2011/069951A1) and 5,5-dimethyl-3-[6-(spiro[1-benzofuran-3,1'-cyclopropan]-4-yloxy)-3-pyridinyl]-2,4-imidazolidinedione (Reference Example 88 of WO2011/069951A1).

Examples 12, 33, 50, 52 and 58 show limited change in AUC BB in the presence of Elacridar, indicating an absence of notable p-glycoprotein interactions.

Consequently, compounds of the invention, especially those having an oxygen atom located in the benzylic position of the ring A, may be expected to demonstrate good availability in brain tissue.

Biological Example 3

Activity of Modulators of Kv3 in a Mouse Model of Amphetamine Induced Hyperlocomotion Example 33 was tested in the mouse model of amphetamine induced hyperlocomotion described in Example 93 of WO2011/069951A1. At a dose of 60 mg/kg, Example 33 completely prevented ($P<0.01$) the increase in locomotor activity induced by amphetamine measured over a 60 minute period following the amphetamine administration.

Evaluation of the Efficacy of Modulators of Kv3 Channels in a Model of Noise-Induced Hearing Loss in the Chinchilla The otoprotective efficacy of an exemplary Kv3 modulator described within WO2011069951A1, referred to herein as "COMPOUND X", was investigated using a chinchilla model of noise-induced hearing loss, as follows:

Materials and Methods

Subjects comprised male, 3 year old chinchillas (Laniger), 10 animals per group. Chinchillas were housed in the study facility for a minimum of 5 days prior to noise exposure. Food and water were available ad libitum. Animals were maintained at 21° C. on a 12/12 light/dark cycle.

Vehicle and Drug Preparation and Administration

Vehicle (20% Captisol®, 0.5% w/v HPMC K15M and 0.5% w/v Tween 80™) was prepared using autoclaved deionized water not more than one week prior to use. A suspension of COMPOUND X in the vehicle at 10 mg/ml was prepared less than 24 hours prior to administration. COMPOUND X was administered at 60 mg/kg via the intraperitoneal route, with doses 12 hours apart. Five injections were given pre-noise exposure and five post-noise exposure. On the day of noise exposure, injections were given 1.5 hours before the start of noise exposure and one hour after completion of the noise exposure protocol.

Noise Exposure

Animals were placed in a sound-attenuated booth for 15 minutes prior to noise exposure. Noise exposure consisted of a 105 dB SPL octave-band noise centered at 4 kHz (TDT GNS 40× white noise generator) for 6 hours duration. The noise was routed through an attenuator (TDT PA3), a filter (Krohn-Hite 3384) and a power amplifier (Sony 55ES) to a custom-built acoustic exponential horn with a maximum output at 4 kHz using an Altec 209E driver. The loudspeaker was suspended directly above the cage. During noise exposure, animals had access to water, but not food.

Auditory Brainstem Response

Auditory brainstem responses (ABRs) were collected prior to noise exposure and 21 days after noise exposure. All animals were anesthetized throughout the ABR procedure and prior to sacrifice with a 0.3 ml/kg IM injection of 50 mg/mL ketamine, 5 mg/mL xylazine, and 1 mg/kg acepromazine. Thresholds were measured in response to tone-bursts with 1 ms rise/fall and a 0 ms plateau gated by a Blackman envelope and centred at the frequencies of 2, 4, 6 and 8 kHz, presented at 30/s. Two intensity series were obtained for each animal from 100 to 0 dB peak SPL in 10 dB decrements with 512 sweeps per average. The recording epoch was 15 ms following stimulus onset. Responses were analogue filtered with a 30-3000 Hz band pass. Threshold is defined as the lowest intensity capable of eliciting a replicable, visually detectable auditory brainstem response in both intensity series.

Further details of these methods can also be found in Campbell et al. (2011) Hearing Research 282, 138-144.

Data Analysis

The thresholds for ABRs at the four different sound frequencies at day 21 post-noise exposure were compared to the thresholds at baseline, prior to noise exposure in order to determine a threshold shift for each animal. The data were then analysed using a 2-way ANOVA, with treatment and frequency as main factors.

RESULTS

In this assay, COMPOUND X significantly reduced the permanent threshold shift in ABR observed 21 days after noise exposure (p<0.01). These results support the potential efficacy of COMPOUND X and of small molecule Kv3 channel modulators in general in the treatment of hearing disorders, in particular noise-induced hearing loss.

All publications, including but not limited to patents and patent applications, cited in this specification are herein incorporated by reference as if each individual publication were specifically and individually indicated to be incorporated by reference herein as though fully set forth.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The invention claimed is:

1. A compound of formula (IB);

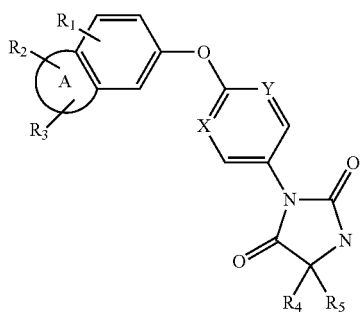

(IB)

wherein $R_1$ is H, or $C_{1-4}$alkyl, halo, halo$C_{1-4}$alkyl, CN, $C_{1-4}$alkoxy, halo$C_{1-4}$alkoxy;

A is a 5 or 6 membered saturated or unsaturated heterocycle, with at least one O atom; which heterocycle is optionally fused with a cyclopropyl group to form a tricycle when considered together with the phenyl;

$R_2$ is H, $C_{1-4}$alkyl, $C_{3-4}$ spiro carbocycly, halo$C_{1-4}$alkyl or halo;

$R_3$ is H, $C_{1-4}$alkyl, halo$C_{1-4}$alkyl, halo;

X is CH or N;

Y is CH or N;

$R_4$ is $C_{1-4}$ alkyl;

$R_5$ is H, Deuterium, $C_{1-4}$ alkyl;

or $R_4$ and $R_5$ can be fused to form $C_{3-4}$ spiro carbocyclyl;

wherein $R_2$ and $R_3$ may be attached to the same or a different ring atom;

and wherein $R_2$ may be attached to a fused ring atom;

or a pharmaceutically acceptable salt thereof.

2. A compound according to claim 1, wherein $R_1$ is H or methyl.

3. A compound according to claim 1, wherein $R_2$ is H, $C_{1-4}$alkyl or $C_3$ spiro.

4. A compound according to claim 1, wherein $R_3$ is H or $C_{1-4}$alkyl.

5. A compound according to claim 1, wherein X is CH.

6. A compound according to claim 1, wherein X is N.

7. A compound according to claim 1, wherein Y is N.

8. A compound according to claim 1, wherein $R_4$ is methyl or ethyl.

9. A compound according to claim 1, wherein $R_5$ is H or methyl.

10. A compound of the following formula:

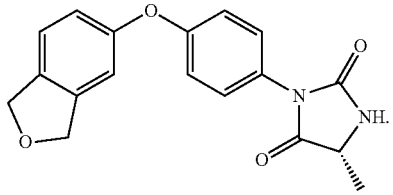 [SMILES: C[C@H]1NC(=O)N(c2ccc(Oc3ccc4c(c3)COC4)cc2)C1=O]

11. A pharmaceutical composition comprising a compound according to claim 1 and a pharmaceutically acceptable carrier or excipient.

* * * * *